US012270040B2

(12) United States Patent
Meksem et al.

(10) Patent No.: US 12,270,040 B2
(45) Date of Patent: Apr. 8, 2025

(54) SOYBEAN LINES WITH LOW SATURATED FATTY ACID AND HIGH OLEIC ACID CONTENTS

(71) Applicant: Board of Trustees of Southern Illinois University, Carbondale, IL (US)

(72) Inventors: Khalid Meksem, Carbondale, IL (US); Naoufal Lakhssassi, Carbondale, IL (US); Dounya Knizia, Carbondale, IL (US); Zhou Zhou, Carbondale, IL (US)

(73) Assignee: Board of Trustees of Southern Illinois University, Carbondale, IL (US)

( * ) Notice: Subject to any disclaimer, the term of this patent is extended or adjusted under 35 U.S.C. 154(b) by 167 days.

(21) Appl. No.: 17/827,259

(22) Filed: May 27, 2022

(65) Prior Publication Data

US 2022/0380789 A1    Dec. 1, 2022

Related U.S. Application Data

(60) Provisional application No. 63/193,705, filed on May 27, 2021.

(51) Int. Cl.
*C12N 15/82* (2006.01)
*A01H 5/10* (2018.01)
*A01H 6/54* (2018.01)

(52) U.S. Cl.
CPC ........... *C12N 15/8247* (2013.01); *A01H 5/10* (2013.01); *A01H 6/542* (2018.05)

(58) Field of Classification Search
None
See application file for complete search history.

(56) References Cited

U.S. PATENT DOCUMENTS

| 2004/0034888 | A1* | 2/2004 | Liu | C07H 21/04 |
| | | | | 536/23.6 |
| 2016/0186195 | A1* | 6/2016 | Damude | C12N 9/0083 |
| | | | | 800/312 |
| 2017/0367383 | A1* | 12/2017 | Esquivel | A23L 13/60 |
| 2018/0028512 | A1* | 2/2018 | Lee | C08K 5/0016 |
| 2018/0094234 | A1* | 4/2018 | Lyte | C12N 1/20 |

FOREIGN PATENT DOCUMENTS

WO    2021155376 A1    8/2021

OTHER PUBLICATIONS

Zrimec et al Nature communications 13.1 (2022): 5099 (Year: 2022).*
Buhr et al., The Plant Journal 30.2 (2002): 155-163 (Year: 2002).*
Jing et al., Nature communications 9.1 (2018): 860 (Year: 2018).*
Cardinal et al., Crop Science 47.1 (2007): 304-310 (Year: 2007).*
Park et al., Plant biotechnology journal 12.8 (2014): 1035-1043 (Year: 2014).*
Zhou et al., Theoretical and Applied Genetics 134 (2021): 3611-3623 (Year: 2021).*
Vogel et al., Plant biotechnology journal 17.7 (2019): 1369-1379 (Year: 2019).*
Benfey and Chua, 1990, The Cauliflower Mosaic Virus 35S Promoter: Combinatorial Regulation of Transcription in Plants, Science 250: 959-966. (Year: 1990).*
Morton et al., 2014, Paired-End Analysis of Transcription Start Sites in *Arabidopsis* Reveals Plant-Specific Promoter Signatures, The Plant Cell 26: 2746-2760 . (Year: 2014).*
Dutt et al., 2014, Temporal and Spatial Control of Gene Expression in Horticultural Crops, Horticulture Research 1, 14047: 1-17. (Year: 2014).*
Till, B., et al., "Induced Plant Mutations in the Genomics Era: Global Tilling Projects," 2009, Q.Y. Shu (Ed.), Food and Agriculture Organization of the United Nations, Rome, pp. 237-239, 4 pages.
Voelker, T.A., "Plant Acyl-ACP Thioesterases: Chain-Length Determining Enzymes in Plant Fatty Acid Biosynthesis," 1996, Genetic Engineering, J.K. Setlow (Ed.), Plenum Press, 18:111-133.
Voelker, T.A., et al., "Broad-Range and Binary-Range Acyl-Acylcarrier-Protein Thioesterases Suggest an Alternative Mechanism for Medium-Chain Production in Seeds," 1997, Plant Physiology, 114:669-677, 9 pages.
Wilson, R., et al., "Metabolic Mechanisms Associated with Alleles Governing the 16:0 Concentration of Soybean Oil," 2001, JAOCS, 78:335-340, 6 pages.
Young, N.D., et al., "Genome-Enabled Insights into Legume Biology," 2012, Ann Rev of Plant Biol, 63:283-305, 25 pages.
Zhou, Z., et al., "Assessment of Phenotypic Variations and Correlation Among Seed Composition Traits in Mutagenized Soybean Populations," 2019, Genes, 10:975, 14 pages.
Zhou, Z., et al., "Genome-wide Identification and Analysis of Soybean acyl-ACP Thioesterase Gene Family Reveals the Role of GmFT to Improve Fatty Acid Composition in Soybean Seed," Published Online Jul. 28, 2021, Theoretical and Applied Genetics, https://doi.org/10.1007/s00122-021-03917-9, 13 pages.
Babicki, S., et al., "Heatmapper: Webenabled Heat Mapping for All," 2016, Nucl Acids Res, Web Server Issue, 44: W147-W153, 7 pages.
Bachleda, N., et al., "Identifying FATB1a Deletion that Causes Reduced Palmitic Acid Content in Soybean N87-2122-4 to Develop a Functional Marker for Marker-Assisted Selection," 2016, Mol Breeding, 36:45, 9 pages.
Bonaventure, G., et al., "Disruption of the FATB Gene in Arabidopsis Demonstrates an Essential Role of Saturated Fatty Acids in Plant Growth," 2003, Plant Cell, 15:1020-1033, 15 pages.

(Continued)

*Primary Examiner* — Bratislav Stankovic
(74) *Attorney, Agent, or Firm* — Stinson LLP

(57) ABSTRACT

The present invention is directed to a transgenic soybean plant having increased oleic acid content comprising a polynucleotide comprising a fatty acid thioesterase (FAT) related promoter that functions in the soybean plant operably linked to a polynucleotide encoding a polypeptide having FAT activity. The invention is further directed to a method of increasing oleic acid content of a soybean plant comprising transforming a soybean plant with a polynucleotide comprising a fatty acid thioesterase (FAT) related promoter that functions in the soybean plant operably linked to a polynucleotide encoding a polypeptide having FAT activity.

5 Claims, 13 Drawing Sheets

Specification includes a Sequence Listing.

(56) References Cited

OTHER PUBLICATIONS

Bowers, J.E., et al., "Unravelling Angiosperm Genome Evolution by Phylogenetic Analysis of Chromosomal Duplication Events," 2003, Nature, 422:433-438, 6 pages.

Buhr, T., et al., "Ribozyme Termination of RNA Transcripts Down-Regulate Seed Fatty Acid Genes in Transgenic Soybean," 2002, The Plant Journal, 30:155-163, 9 pages.

Burton, J., et al., "Registration of N79-2077-12 and N87-2122-4, Two sSoybean Germplasm Lines with Reduced Palmitic Acid in Seed Oil," 1994, Crop Sci, 34:313, 1 page.

Byfield, G.E., et al., "Effect of Temperature on Delta-9 Stearoyl-ACP and Microsomal Omega-6 Desaturase Gene Expression and Fatty Acid Content in Developing Soybean Seeds," 2007, Crop Science, 47:1698-1704, 7 pages.

Cantu, D.C., et al., "ThYme: A Database for Thioester-Active Enzymes." 2010, Nucl Acids Res, Database Issue, 39: D342-D346, 5 pages.

Cardinal, A.J., et al., "Molecular Analysis of Soybean Lines with Low Palmitic Acid Content in the Seed Oil," 2007, Crop Science, 47:304-310, 8 pages.

Cardinal, A.J., et al., "Mapping the Low Palmitate FAP1 Mutation and Validation of its Effects in Soybean Oil and Agronomic Traits in Three Soybean Populations," 2014, Theor Appl Genet, 127:97-111, 15 pages.

Chen, X., et al., "Genome-Wide Analysis of Soybean HD-Zip Gene Family and Expression Profiling Under Salinity and Drought Treatments," 2014, PloS one 9/2:e87156, 17 pages.

Cooper, J.L., et al., "Tilling to Detect Induced Mutations in Soybean," 2008, BMC Plant Biology 8:9, 10 pages.

De Vries, B.D., et al., "Molecular Characterization of the Mutant FAP3(A22) Allele for Reduced Palmitate Concentration in Soybean," 2011, Crop Science, 51:1611-1616, 6 pages.

Dierking, E.C., et al., "New Sources of Soybean Seed Meal and Oil Composition Traits Identified Through Tilling," 2009, BMC Plant Biol 9:89, 11 pages.

Dormann, P., et al., "Cloning and Expression in *Escherichia coli* of a Novel Thioesterase from *Arabidopsis thaliana* Specific for Long-Chain Acyl-Acyl Carrier Proteins," 1995, Archives of Biochemistry and Biophysics, 316:612-618, 7 pages.

Eckardt, N.A., "Two Genomes are Better Than One: Widespread Paleopolyploidy in Plants and Evolutionary Effects," 2004, Plant Cell, 16:1647-1649, 3 pages.

Fehr, W.R., "Breeding for Modified Fatty Acid Composition in Soybean," 2007, Crop Science, 47:S-72-S-87, 17 pages.

Goettel, W., et al., "Identification and Characterization of Large DNA Deletions Affecting Oil Quality Traits in Soybean Seeds Through Transcriptome Sequencing Analysis," 2016, Theor Appld Genet, 129:1577-1593, 17 pages.

Hall, B.G., "Building Phylogenetic Trees from Molecular Data with MEGA," 2013, Molecular Biology and Evolution, 30:1229-1235, 7 pages.

Hills, M.J., "Improving Oil Functionality by Tuning Catalysis of Thioesterase," 1999, Trends in Plant Science, 4/11:421-422, 2 pages.

Hu, B., et al., "Dietary Fat Intake and the Risk of Coronary Heart Disease in Women," 1997, New England Journal of Medicine, 337:1491-1499, 9 pages.

Hu, B., et al., "GSDS 2.0: An Upgraded Gene Feature Visualization Server," 2015, Bioinformatics 31/8:1296-1297, 2 pages.

Jing, F., et al., "Two Distinct Domains Contribute to the Substrate Acyl Chain Length Selectivity of Plant Acyl-ACP Thioesterase," 2018, Nature Communications, 9:1-10, 10 pages.

Juretic, N., et al., "The Evolutionary Fate of MULE-Mediated Duplications of Host Gene Fragments in Rice," 2005, Genome Research, 15:1292-1297, 6 pages.

Kong, H., et al., "Patterns of Gene Duplication in the Plant SKP1 Gene Family in Angiosperms: Evidence for Multiple Mechanisms of Rapid Gene Birth," 2007, The Plant Journal, 50:873-885, 13 pages.

Koornneef, M., et al., "Chapter 5: EMS- and Relation-Induced Mutation Frequencies at Individual loci in *Arabidopsis thaliana* (L.) Heynh," 1982, Mutation Research/Fundamental and Molecular Mechanisms of Mutagenesis, 93:109-123, 15 pages.

Koressaar, T., et al., "Enhancements and Modifications of Primer Design Program Primer3," 2007, Bioinformatics, 23:1289-1291, 3 pages.

Kramer, J.K., et al., "Evaluating Acid and Base Catalysts in the Methylation of Milk and Rumen Fatty Acids with Special Emphasis on Conjugated Dienes and Total Trans Fatty Acids," 1997, Lipids, 32:1219-1228, 10 pages.

Krasileva, K.V., et al., "Uncovering Hidden Variation in Polyploid Wheat," 2017, PNAS, 114:E913-E921, 9 pages.

Kumar, S., et al., "Mega X: Molecular Evolutionary Genetics Analysis Across Computing Platforms," 2018, Mol Biol Evol, 35:1547-1549, 3 pages.

Lakhssassi, N., et al., "Characterization of the FAD2 Gene Family in Soybean Reveals the Limitations of Gel-Based Tilling in Genes with High Copy Number," 2017, Frontiers in Plant Science, 8:324, 15 pages.

Lee, T-H., et al., "PGDD: A Database of Gene and Genome Duplication in Plants," 2012, Nucl Acids Res, Database Issue, 41:D1152-D1158, 7 pages.

Li, W-H., et al., "Pseudogenes as a Paradigm of Neutral Evolution," 1981, Nature, 292:237-239, 3 pages.

Liu, S., et al., "A Soybean Cyst Nematode Resistance Gene Points to a New Mechanism of Plant Resistance to Pathogens," 2012, Nature, 492:256-260, 7 pages.

Mayer, K.M., et al., "A Structural Model of the Plant Acyl-Acyl Carrier Protein Thioesterase FatB Comprises Two Helix/4-Stranded Sheet Domains, the N-terminal Domain Containing Residues that Affect Specificity and the C-Terminal Domain Containing Catalytic Residues," 2005, Journal of Biological Chemistry, 280/5:3621-3627, 7 pages.

Mayer, K.M., et al., "Identification of Amino Acid Residues Involved in Substrate Specificity of Plant Acyl-ACP Thioesterases Using a Bioinformatics-Guided Approach," 2007, BMC Plant Biology, 7/1, 11 pages.

McCallum, C.M., et al., "Targeted Screening for Induced Mutations," 2000, Nature Biotechnology, 18:455-457, 3 pages.

Okonechnikov, K., et al., "Unipro Ugene: A Unified Bioinformatics Toolkit," 2012, Bioinformatics, 28/8:1166-1167, 2 pages.

Primomo, V., "Inheritance and Stability of Palmitic Acid Alleles in Soybeans," Master's Thesis, 2000, University of Guelph, Guelph, ON, Canada, 157 pages.

Rahman, S.M., et al., "Genetic Analysis of Palmitic Acid Contents Using Two Soybean Mutants, J3 and J10," 1996, Japanese Journal of Breeding Science, 46:343-347, 5 pages.

Rebetzke ,G.J., et al., "Genetic Variation for Modifiers Controlling Reduced Saturated Fatty Acid Content in Soybean," 1998, Crop Science, 38:303-308, 7 pages.

Salas, J.J., "Characterization of Substrate Specificity of Plant FatA and FatB Acyl-ACP Thioesterases," 2002, Archives of Biochemistry and Biophysics, 403:25-34, 10 pages.

Schmutz, J., et al., "Genome Sequence of the Palaeopolyploid Soybean," 2010, Nature, 463:178-183, 10 pages.

Schmutz, J., et al., "A Reference Genome for Common Bean and Genome-Wide Analysis of Dual Domestications," 2014, Nature Genetics, 46/7:707-716, 10 pages.

Schnebly, S.R., et al., "Inheritance of Reduced and Elevated Palmitate in Mutant Lines of Soybean," 1994, Crop Science, 34:829-833, 5 pages.

Soystats 2018, A Reference to Soybean Facts and Figures, American Soybean Association, 36 pages.

Stijšin, D., et al., "Use of Gene Substitution Values to Quantify Partial Dominance in Low Palmitic Acid Soybean," 1998, Crop Science, 38:1437-1441, 5 pages.

Stoltzfus, D.L.. et al., "Relationship of Elevated Palmitate to Soybean Seed Traits," 2000, Crop Science, 40:52-54, 4 pages.

Suyama, M., et al., "PAL2NAL: Robust Conversion of Protein Sequence Alignments into the Corresponding Codon Alignments," 2006, Nucl Acids Res, Web Server Issue, 34:W609-W612, 4 pages.

(56) References Cited

OTHER PUBLICATIONS

Thapa, R., et al., "New Alleles of FATB1A to Reduce Palmitic Acid Levels in Soybean," 2016, Crop Science 56:1076-1080, 6 pages.

* cited by examiner

FIG. 6

|  |  | Hotdog domain | | | | | | | | | | | | | | | |
|---|---|---|---|---|---|---|---|---|---|---|---|---|---|---|---|---|---|
|  |  |  | | | | | I | | | | | | | | II | | | |
|  | Residue Number | 150a | 163 | 178 | 194b | 208b | 212 | 213 | 236 | 246 | 276b | 340c | 342c | 347 | 362 | 372 | 377c |
| FATA | AT3G25110 AtFATA1 | K | N | V | A | T | H | I | R | K | D | N | H | T | D | D | C |
|  | AT4G13050 At FATA2 | K | N | V | A | T | H | I | R | K | D | N | H | T | D | D | C |
|  | Glyma.18G167300 GmFATA1A | K | N | V | A | T | H | I | R | K | D | N | H | T | D | D | C |
|  | Glyma.08G349200 GmFATA1B | K | N | V | A | T | H | I | R | K | D | N | H | T | D | D | C |
|  | AT1G08510 AtFATB | R | D | T | G | V | Q | V | K | R | E | N | H | K | E | E | C |
| FATB | Glyma.05G012300 GmFATB1A | R | D | T | G | V | Q | V | K | R | E | N | H | K | E | E | C |
|  | Glyma.17G120400 GmFATB1B | R | D | T | G | V | Q | V | K | R | E | N | H | K | E | E | C |
|  | Glyma.04G015160 GmFATB2A | R | D | T | G | V | Q | V | K | R | E | N | H | K | E | E | C |
|  | Glyma.06G211300 GmFATB2B | R | D | T | G | V | Q | V | K | R | E | N | H | K | E | E | C |
|  | Glyma.04G197400 GmFATB3A | R | D | T | G | V | Q | V | K | R | E | N | H | K | E | E | C |
|  | Glyma.06G168100 GmFATB3B | R | D | T | G | V | Q | V | K | R | E | N | H | K | E | E | C |
|  | Glyma.04G197500 GmFATB4A | R | D | T | G | V | Q | V | K | R | E | N | H | K | E | E | C |
|  | Glyma.06G168000 GmFATB4B | R | D | T | G | V | Q | V | K | R | E | N | H | K | E | E | C |
|  | Glyma.10G268200 GmFATB5A | R | D | T | G | V | Q | V | K | R | E | N | H | K | E | E | C |
|  | Glyma.20G122900 GmFATB5B | R | D | T | G | V | Q | V | K | R | E | N | H | K | E | E | C |

| Gene symbol | Gene ID | Amplicon size (bp) | Base changes | Type of base changes | | | InDel | AA substitutions | Missense mutations | Nonsense mutations | Silent mutations | Mutation density (Kb) |
|---|---|---|---|---|---|---|---|---|---|---|---|---|
| | | | | G > A | C > T | Others | | | | | | |
| GmFATB1A | Glyma.05G013300 | 2960 | 42 | 19 | 14 | 9 | 1 | 17 | 12 | 0 | 5 | 1/284 |
| GmFATB1B | Glyma.17G120400 | 2960 | 38 | 18 | 18 | 2 | 3 | 13 | 11 | 0 | 2 | 1/314 |
| GmFATB2A | Glyma.04G151600 | 4840 | 93 | 40 | 41 | 12 | 1 | 30 | 20 | 1 | 9 | 1/210 |
| GmFATB2B | Glyma.06G211300 | 2760 | 69 | 33 | 18 | 18 | 3 | 41 | 29 | 1 | 11 | 1/161 |
| GmFATA1A | Glyma.18G167300 | 2600 | 38 | 18 | 13 | 7 | 0 | 17 | 12 | 1 | 4 | 1/276 |
| Total | | 16120 | 280 | 128 | 104 | 48 | 8 | 118 | 84 | 3 | 31 | 1/232 |
| Percentage of each type of base change | | | | 45.7% | 37.1% | 17.1% | | | | | | |
| Percentage of each type of amino acid change | | | | | | | | | 71.2% | 2.5% | 26.3% | |

| Gene ID | Plant ID | Nucleotide change | Amino acid substitution | C16:0 | C18:0 | C18:1 | C18:2 | C18:3 |
|---|---|---|---|---|---|---|---|---|
| GmFATA-1A (Glyma.18g167300) | F740 | C437T | T146I | 10.5 | 3.8 | 25.3 | 52.4 | 6 |
| | F243 | C692T | A231V | 9.1 | 3.6 | 32.4 | 44.7 | 8.8 |
| | F393 | G830A | G277E | 9.9 | 4.1 | 34.5 | 45.2 | 4.1 |
| | F636 | C110T | S37F | 10.2 | 5.1 | 27.6 | 51.3 | 5.7 |
| | F1305 | G163T | A55T | 10.5 | 5.5 | 25.4 | 52.8 | 5.8 |
| | F996 | G928A | V310I | 8.0 | 3.5 | 28.6 | 51.7 | 8.1 |
| GmFATB-1A (Glyma.05g012300) | F236 | G539A | G180D | 7.5 | 3.3 | 22.2 | 55.1 | 7 |
| | F1166 | G1111A | A371T | 8.9 | 7.1 | 26.2 | 49.1 | 5.2 |
| | F1040 | C52T | P18L | 9.3 | 4.7 | 32.2 | 48.0 | 5.9 |
| | F1129 | G382A | G128R | 10.2 | 4.8 | 34.0 | 46.0 | 5.1 |
| | F1200 | G668A | G223E | 9.2 | 4.2 | 23.9 | 54.7 | 8.0 |
| | F1108 | G850A | D284N | 10.5 | 5.1 | 26.0 | 51.7 | 6.6 |
| GmFATB-1B (Glyma.17g120400) | F359 | C352T | P118S | 10.6 | 7.6 | 25 | 48.2 | 6.7 |
| | F43 | G383A | G128E | 9.5 | 4.5 | 31.9 | 46.2 | 6.2 |
| | F538 | T380* | I127X | 10.1 | 3.9 | 27.8 | 51.2 | 6.9 |
| | F858 | G1043A | R348K | 12.0 | 4.1 | 26.5 | 51.8 | 5.6 |
| | F1726 | G520A | A174T | 8.5 | 4.3 | 33.4 | 47.1 | 6.7 |
| | F1345 | C47T | P16L | 9.6 | 3.5 | 36.5 | 45.5 | 5.0 |
| GmFATB-2A Glyma.04G151600 | F1104 | G1117A | A373T | 9.9 | 4.2 | 34.3 | 46.2 | 5.3 |
| | F1220 | G1154A | R385Q | 9.6 | 6.1 | 26.5 | 52.0 | 5.9 |
| | F884 | G1184A | G395D | 11.1 | 4.3 | 24.6 | 51.4 | 8.6 |
| GmFATB-2B Glyma.06G211300 | F564 | C98ST | Q30* | 10.1 | 3.0 | 21.1 | 57.0 | 8.7 |
| | F317 | G136A | G46S | 8.9 | 10.0 | 34.8 | 41.3 | 4.9 |
| | F225 | G763A | V255M | 11.9 | 3.4 | 19.9 | 56.0 | 8.9 |
| Wild-type | F-WT | | | 11.59 | 3.32 | 18.04 | 54.52 | 6.19 |

SEQUENCE LISTING

<160> NUMBER OF SEQ ID NOS: 36

<210> SEQ ID NO 1
<211> LENGTH: 138
<212> TYPE: PRT
<213> ORGANISM: Glycine max

<400> SEQUENCE: 1

```
Tyr Lys Glu Lys Phe Ile Val Arg Ser Tyr Glu Val Gly Ile Asn Lys
1               5                   10                  15

Thr Ala Thr Val Glu Thr Ile Ala Asn Leu Leu Gln Glu Val Gly Cys
            20                  25                  30

Asn His Ala Gln Ser Val Gly Tyr Ser Thr Asp Gly Phe Ala Thr Thr
        35                  40                  45

Pro Thr Met Arg Lys Leu Arg Leu Ile Trp Val Thr Ala Arg Met His
    50                  55                  60

Ile Glu Ile Tyr Lys Tyr Pro Ala Trp Ser Asp Ile Val Glu Ile Glu
65              70                  75                  80

Thr Trp Cys Gln Gly Glu Gly Arg Val Gly Thr Arg Arg Asp Phe Ile
            85                  90                  95

Leu Lys Asp Tyr Ala Thr Asp Glu Val Ile Gly Arg Ala Thr Ser Lys
            100                 105                 110

Trp Val Met Met Asn Gln Asp Thr Arg Arg Leu Gln Lys Val Ser Asp
            115                 120                 125

Asp Val Lys Glu Glu Tyr Leu Val Phe Cys
        130                 135

<210> SEQ ID NO 2
<211> LENGTH: 138
<212> TYPE: PRT
<213> ORGANISM: Glycine max

<400> SEQUENCE: 2

Tyr Lys Glu Lys Phe Ile Val Arg Ser Tyr Glu Val Gly Ile Asn Lys
1               5                   10                  15

Thr Ala Thr Val Glu Thr Ile Ala Asn Leu Leu Gln Glu Val Gly Cys
            20                  25                  30

Asn His Ala Gln Ser Val Gly Tyr Ser Thr Asp Gly Phe Ala Thr Thr
        35                  40                  45

Pro Thr Met Arg Lys Leu Arg Leu Ile Trp Val Thr Ala Arg Met His
    50                  55                  60

Ile Glu Ile Tyr Lys Tyr Pro Ala Trp Ser Asp Val Val Glu Ile Glu
65              70                  75                  80

Thr Trp Cys Gln Gly Glu Gly Arg Val Gly Thr Arg Arg Asp Phe Ile
            85                  90                  95

Leu Lys Asp Tyr Ala Ser Asp Ala Val Ile Gly Arg Ala Thr Ser Lys
            100                 105                 110

Trp Val Met Met Asn Gln Asp Thr Arg Arg Leu Gln Lys Val Ser Asp
            115                 120                 125

Asp Val Lys Glu Glu Tyr Leu Val Phe Cys
        130                 135

<210> SEQ ID NO 3
<211> LENGTH: 138
<212> TYPE: PRT
<213> ORGANISM: Arabidopsis thaliana

<400> SEQUENCE: 3

Tyr Lys Glu Lys Phe Val Val Arg Ser Tyr Glu Val Gly Ser Asn Lys
1               5                   10                  15

Thr Ala Thr Val Glu Thr Ile Ala Asn Leu Leu Gln Glu Val Gly Cys
            20                  25                  30

Asn His Ala Gln Ser Val Gly Phe Ser Thr Asp Gly Phe Ala Thr Thr
        35                  40                  45
```

Thr Thr Met Arg Lys Leu His Leu Ile Trp Val Thr Ala Arg Met His
        50                  55                  60

Ile Glu Ile Tyr Lys Tyr Pro Ala Trp Gly Asp Val Val Glu Ile Glu
65                  70                  75                  80

Thr Trp Cys Gln Ser Glu Gly Arg Ile Gly Thr Arg Arg Asp Trp Ile
                85                  90                  95

Leu Lys Asp Ser Val Thr Gly Glu Val Thr Gly Arg Ala Thr Ser Lys
            100                 105                 110

Trp Val Met Met Asn Gln Asp Thr Arg Arg Leu Gln Lys Val Ser Asp
        115                 120                 125

Asp Val Arg Asp Glu Tyr Leu Val Phe Cys
    130                 135

<210> SEQ ID NO 4
<211> LENGTH: 138
<212> TYPE: PRT
<213> ORGANISM: Arabidopsis thaliana

<400> SEQUENCE: 4

Tyr Lys Glu Lys Phe Ile Val Arg Ser Tyr Glu Val Gly Ile Asn Lys
1               5                   10                  15

Thr Ala Thr Ile Glu Thr Ile Ala Asn Leu Leu Gln Glu Val Ala Cys
            20                  25                  30

Asn His Val Gln Asn Val Gly Phe Ser Thr Asp Gly Phe Ala Thr Thr
        35                  40                  45

Leu Thr Met Arg Lys Leu His Leu Ile Trp Val Thr Ala Arg Met His
    50                  55                  60

Ile Glu Ile Tyr Lys Tyr Pro Ala Trp Ser Asp Val Val Glu Ile Glu
65                  70                  75                  80

Thr Trp Cys Gln Ser Glu Gly Arg Ile Gly Thr Arg Arg Asp Trp Ile
                85                  90                  95

Leu Lys Asp Cys Ala Thr Gly Glu Val Ile Gly Arg Ala Thr Ser Lys
            100                 105                 110

Trp Val Met Met Asn Gln Asp Thr Arg Arg Leu Gln Arg Val Thr Asp
        115                 120                 125

Glu Val Arg Asp Glu Tyr Leu Val Phe Cys
    130                 135

<210> SEQ ID NO 5
<211> LENGTH: 138
<212> TYPE: PRT
<213> ORGANISM: Glycine max

<400> SEQUENCE: 5

Phe Arg Gln Ile Phe Val Ile Arg Ser Tyr Glu Ile Gly Pro Asp Lys
1               5                   10                  15

Thr Ala Thr Met Glu Thr Ile Met Asn Phe Leu Gln Glu Thr Ala Leu
            20                  25                  30

Asn His Val Thr Ser Ser Gly Ile Gly Gly Glu Gly Phe Gly Ala Thr
        35                  40                  45

Arg Glu Met Ser Leu Arg Lys Leu Ile Trp Val Thr Arg Ile Gln
    50                  55                  60

Val Gln Val Gln Arg Tyr Asn Lys Trp Gly Asp Glu Ile Glu Val Asp
65                  70                  75                  80

Thr Trp Val Asp Ala Ala Gly Lys Asn Gly Met Arg Arg Asp Trp Ile
                85                  90                  95

```
Ile Arg Asp His Tyr Thr Lys Glu Ile Ile Thr Arg Ala Thr Ser Thr
            100                 105                 110

Trp Val Ile Met Asn Arg Gln Thr Arg Arg Leu Ser Lys Ile Pro Glu
        115                 120                 125

Glu Val Lys Gln Glu Leu Leu Pro Phe Tyr
    130                 135

<210> SEQ ID NO 6
<211> LENGTH: 138
<212> TYPE: PRT
<213> ORGANISM: Glycine max

<400> SEQUENCE: 6

Phe Arg Gln Ile Phe Val Ile Arg Ser Tyr Glu Ile Gly Pro Asp Lys
1               5                   10                  15

Thr Ala Thr Met Glu Thr Leu Met Asn Phe Leu Gln Glu Thr Ala Leu
            20                  25                  30

Asn His Val Thr Ser Ser Gly Ile Gly Gly Glu Gly Phe Gly Ala Thr
        35                  40                  45

Arg Glu Met Ser Leu Arg Lys Leu Ile Trp Val Val Thr Arg Ile Gln
    50                  55                  60

Val Gln Val Gln Arg Tyr Asn Lys Trp Gly Asp Glu Ile Glu Val Asp
65                  70                  75                  80

Thr Trp Val Asp Ala Ala Gly Lys Asn Gly Met Arg Arg Asp Trp Ile
                85                  90                  95

Ile Arg Asp His Tyr Thr Lys Glu Ile Ile Thr Arg Ala Thr Ser Thr
            100                 105                 110

Trp Val Ile Met Asn Arg Gln Thr Arg Arg Leu Ser Lys Ile Pro Glu
        115                 120                 125

Glu Val Lys Gln Glu Leu Leu Pro Phe Tyr
    130                 135

<210> SEQ ID NO 7
<211> LENGTH: 138
<212> TYPE: PRT
<213> ORGANISM: Glycine max

<400> SEQUENCE: 7

Tyr Arg Gln Ile Phe Phe Val Arg Ser Tyr Glu Ile Gly Pro Asp Lys
1               5                   10                  15

Thr Ile Thr Val Glu Thr Leu Met Asn Phe Leu Gln Glu Thr Cys Leu
            20                  25                  30

Asn His Met Ser Asn Cys Gly Val Ser Gln Asn Asp Phe Gly Ala Thr
        35                  40                  45

His Glu Met Asp Leu Arg Lys Leu Ile Trp Val Val Thr Arg Ile Gln
    50                  55                  60

Val Gln Val Gln Arg Tyr Ser Lys Trp Gly Glu Glu Ile Glu Val Asp
65                  70                  75                  80

Thr Trp Phe Asp Ile Ala Gly Lys Asn Gly Ile Arg Arg Asp Trp Ile
                85                  90                  95

Ile Arg Asp His Tyr Thr Lys Glu Ile Ile Ala Lys Ala Thr Ser Thr
            100                 105                 110

Trp Thr Met Met Asn Arg Glu Thr Arg Arg Leu Ser Lys Ile Ser Glu
        115                 120                 125

Glu Val Arg Gln Glu Leu Val Pro Phe Phe
    130                 135
```

<210> SEQ ID NO 8
<211> LENGTH: 138
<212> TYPE: PRT
<213> ORGANISM: Glycine max

<400> SEQUENCE: 8

```
Tyr Arg Gln Thr Phe Phe Val Arg Cys Tyr Glu Ile Gly Pro Asp Lys
1               5                   10                  15

Thr Ile Thr Met Glu Thr Leu Met Asn Phe Leu Gln Glu Thr Ala Leu
            20                  25                  30

Asn His Val Ser Ser Cys Gly Gly Ser Gln Asn Gly Phe Gly Ala Thr
        35                  40                  45

Gln Glu Met Asp Leu Arg Asn Leu Ile Trp Val Val Thr Arg Phe Gln
50                  55                  60

Val Gln Val Gln Arg Tyr Ser Lys Trp Arg Asp Glu Ile Glu Val Glu
65                  70                  75                  80

Thr Trp Phe Asp Val Ala Gly Lys Asn Gly Thr Arg Arg Asp Trp Ile
                85                  90                  95

Val Arg Asp His Tyr Thr Lys Glu Ile Ile Ala Lys Ala Thr Ser Ile
            100                 105                 110

Trp Ala Ile Val Asn Gln Glu Thr Arg Arg Leu Cys Lys Ile Pro Glu
        115                 120                 125

Glu Val Arg Gln Glu Leu Val Thr Phe Tyr
    130                 135
```

<210> SEQ ID NO 9
<211> LENGTH: 138
<212> TYPE: PRT
<213> ORGANISM: Glycine max

<400> SEQUENCE: 9

```
Tyr Arg Gln Thr Val Val Ile Arg Ser Tyr Glu Val Gly Ala Asp Lys
1               5                   10                  15

Thr Ala Thr Leu Glu Ser Ile Leu Asn Leu Leu Gln Glu Thr Ala Leu
            20                  25                  30

Asn His Val Trp Met Ser Gly Leu Leu Ser Asp Gly Phe Gly Ala Thr
        35                  40                  45

His Gly Met Val Arg Asn Asn Leu Ile Trp Val Val Ser Arg Met Gln
50                  55                  60

Val Leu Ile Asp Tyr Tyr Pro Ile Trp Gly Glu Val Val Glu Ile Asp
65                  70                  75                  80

Thr Trp Val Gly Ala Ser Gly Lys Asn Gly Met Arg Arg Asp Trp Leu
                85                  90                  95

Ile Arg Ser Gln Ala Thr Gly His Ile Phe Ala Arg Ala Thr Ser Thr
            100                 105                 110

Trp Val Met Met Asn Arg Lys Thr Arg Arg Leu Ser Lys Met Pro Glu
        115                 120                 125

Glu Val Arg Ala Glu Val Ser Pro Trp Phe
    130                 135
```

<210> SEQ ID NO 10
<211> LENGTH: 138
<212> TYPE: PRT
<213> ORGANISM: Glycine max

<400> SEQUENCE: 10

Tyr Arg Gln Thr Val Ile Arg Ser Tyr Glu Val Gly Ala Asp Lys
1               5                   10                  15

Thr Ala Thr Leu Glu Ser Ile Leu Asn Leu Leu Gln Glu Thr Ala Leu
            20                  25                  30

Asn His Val Trp Met Ser Gly Leu Leu Ser Asp Gly Phe Gly Ala Thr
            35                  40                  45

His Gly Met Val Arg Asn Asp Leu Ile Trp Val Val Ser Arg Met Gln
50                  55                  60

Val Leu Val Asp Tyr Tyr Pro Ile Trp Gly Glu Val Glu Ile Asp
65                  70                  75                  80

Thr Trp Val Gly Ala Ser Gly Lys Asn Gly Met Arg Arg Asp Trp Leu
                85                  90                  95

Ile Arg Ser Gln Val Thr Gly Arg Ile Phe Ala Arg Ala Thr Ser Thr
            100                 105                 110

Trp Val Met Met Asn Arg Lys Thr Arg Arg Leu Ser Lys Met Pro Glu
            115                 120                 125

Glu Val Arg Ala Glu Val Ser Pro Trp Phe
130                 135

<210> SEQ ID NO 11
<211> LENGTH: 138
<212> TYPE: PRT
<213> ORGANISM: Arabidopsis thaliana

<400> SEQUENCE: 11

Phe Arg Gln Asn Phe Ser Ile Arg Ser Tyr Glu Ile Gly Ala Asp Arg
1               5                   10                  15

Ser Ala Ser Ile Glu Thr Val Met Asn His Leu Gln Glu Thr Ala Leu
            20                  25                  30

Asn His Val Lys Thr Ala Gly Leu Leu Gly Asp Gly Phe Gly Ser Thr
            35                  40                  45

Pro Glu Met Phe Lys Lys Asn Leu Ile Trp Val Val Thr Arg Met Gln
50                  55                  60

Val Val Val Asp Lys Tyr Pro Thr Trp Gly Asp Val Val Glu Val Asp
65                  70                  75                  80

Thr Trp Val Ser Gln Ser Gly Lys Asn Gly Met Arg Arg Asp Trp Leu
                85                  90                  95

Val Arg Asp Cys Asn Thr Gly Glu Thr Leu Thr Arg Ala Ser Ser Val
            100                 105                 110

Trp Val Met Met Asn Lys Leu Thr Arg Arg Leu Ser Lys Ile Pro Glu
            115                 120                 125

Glu Val Arg Gly Glu Ile Glu Pro Tyr Phe
130                 135

<210> SEQ ID NO 12
<211> LENGTH: 138
<212> TYPE: PRT
<213> ORGANISM: Glycine max

<400> SEQUENCE: 12

Phe Arg Glu Asn Phe Ser Ile Arg Ser Tyr Glu Ile Gly Ala Asp Arg
1               5                   10                  15

Thr Ala Ser Ile Glu Thr Val Met Asn His Leu Gln Glu Thr Ala Leu
            20                  25                  30

Asn His Val Lys Ser Ala Gly Leu Leu Gly Asp Gly Phe Gly Ser Thr
            35                  40                  45

```
Pro Glu Met Cys Lys Lys Asn Leu Ile Trp Val Val Thr Arg Met Gln
    50                  55                  60

Val Val Val Glu Arg Tyr Pro Thr Trp Gly Asp Ile Val Gln Val Asp
65                  70                  75                  80

Thr Trp Val Ser Gly Ser Gly Lys Asn Gly Met Arg Arg Asp Trp Leu
                85                  90                  95

Leu Arg Asp Cys Lys Thr Gly Glu Ile Leu Thr Arg Ala Ser Ser Val
            100                 105                 110

Trp Val Met Met Asn Lys Leu Thr Arg Arg Leu Ser Lys Ile Pro Glu
            115                 120                 125

Glu Val Arg Gln Glu Ile Gly Ser Tyr Phe
            130                 135
```

<210> SEQ ID NO 13
<211> LENGTH: 138
<212> TYPE: PRT
<213> ORGANISM: Glycine max

<400> SEQUENCE: 13

```
Phe Arg Glu Asn Phe Ser Ile Arg Ser Tyr Glu Ile Gly Ala Asp Arg
1               5                   10                  15

Thr Ala Ser Ile Glu Thr Val Met Asn His Leu Gln Glu Thr Ala Leu
                20                  25                  30

Asn His Val Lys Ser Ala Gly Leu Leu Gly Asp Gly Phe Gly Ser Thr
            35                  40                  45

Pro Glu Met Cys Lys Lys Asn Leu Ile Trp Val Val Thr Arg Met Gln
    50                  55                  60

Val Val Val Asp Arg Tyr Pro Thr Trp Gly Asp Val Val Gln Val Asp
65                  70                  75                  80

Thr Trp Ala Ser Gly Ser Gly Lys Asn Ala Met Arg Arg Asp Trp Val
                85                  90                  95

Leu Arg Asp Cys Lys Thr Gly Glu Ile Leu Thr Arg Ala Ser Ser Val
            100                 105                 110

Trp Val Met Met Asn Lys Leu Thr Arg Arg Leu Ser Lys Ile Pro Glu
            115                 120                 125

Glu Val Arg Gln Glu Ile Gly Ser Tyr Phe
            130                 135
```

<210> SEQ ID NO 14
<211> LENGTH: 138
<212> TYPE: PRT
<213> ORGANISM: Glycine max

<400> SEQUENCE: 14

```
Phe Arg Gln Asn Phe Pro Ile Arg Ser Tyr Glu Ile Gly Ala Asp Lys
1               5                   10                  15

Thr Ala Ser Ile Glu Thr Leu Met Asn His Leu Gln Glu Thr Ala Leu
                20                  25                  30

Asn His Val Lys Thr Ala Gly Leu Leu Gly Asp Gly Phe Gly Ser Thr
            35                  40                  45

Pro Glu Met Cys Lys Lys Asn Leu Ile Trp Val Val Thr Lys Met Gln
    50                  55                  60

Val Val Val Asp Lys Tyr Pro Thr Trp Gly Asp Val Val Gln Val Asp
65                  70                  75                  80

Thr Trp Val Ser Ala Ser Gly Lys Asn Gly Met Arg Arg Asp Trp Leu
                85                  90                  95
```

```
Val Arg Asp Ala Lys Thr Gly Glu Ile Leu Thr Arg Ala Ser Ser Val
            100                 105                 110

Trp Val Met Met Asn Lys Val Thr Arg Arg Leu Ser Lys Ile Pro Glu
        115                 120                 125

Glu Val Arg Ala Glu Ile Ser Ser Tyr Phe
    130                 135

<210> SEQ ID NO 15
<211> LENGTH: 138
<212> TYPE: PRT
<213> ORGANISM: Glycine max

<400> SEQUENCE: 15

Phe Arg Gln Asn Phe Pro Ile Arg Ser Tyr Glu Ile Gly Ala Asp Lys
1               5                   10                  15

Thr Ala Ser Ile Glu Thr Leu Met Asn His Leu Gln Glu Thr Ala Leu
            20                  25                  30

Asn His Val Lys Thr Ala Gly Leu Leu Gly Asp Gly Phe Gly Ser Thr
        35                  40                  45

Pro Glu Met Cys Lys Lys Asn Leu Ile Trp Val Val Thr Lys Met Gln
    50                  55                  60

Val Val Val Asp Lys Tyr Pro Thr Trp Gly Asp Val Val Gln Val Asp
65                  70                  75                  80

Thr Trp Val Ser Ala Ser Gly Lys Asn Gly Met Cys Arg Asp Trp Leu
                85                  90                  95

Val Arg Asp Ala Lys Ser Gly Glu Ile Leu Thr Arg Ala Ser Ser Val
            100                 105                 110

Trp Val Met Met Asn Lys Val Thr Arg Arg Leu Ser Lys Ile Pro Glu
        115                 120                 125

Glu Val Arg Ala Glu Ile Ser Ser Tyr Phe
    130                 135

<210> SEQ ID NO 16
<211> LENGTH: 138
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (52)..(52)
<223> OTHER INFORMATION: Xaa can be Arg, Ser, Asp, Val, Phe, or Cys.
<220> FEATURE:
<221> NAME/KEY: MISC_FEATURE
<222> LOCATION: (100)..(100)
<223> OTHER INFORMATION: Xaa can be Tyr, Ser, Cys, His, Gln, or Ala.
<220> FEATURE:
<221> NAME/KEY: MISC_FEATURE
<222> LOCATION: (101)..(101)
<223> OTHER INFORMATION: Xaa can be Ala, Val, Tyr, Asn, or Lys.
<220> FEATURE:
<221> NAME/KEY: MISC_FEATURE
<222> LOCATION: (112)..(112)
<223> OTHER INFORMATION: Xaa can be Lys, Thr, Ile, or Val.
<220> FEATURE:
<221> NAME/KEY: MISC_FEATURE
<222> LOCATION: (118)..(118)
<223> OTHER INFORMATION: Xaa can be Gln, Arg, or Lys.

<400> SEQUENCE: 16

Tyr Arg Gln Asn Phe Val Ile Arg Ser Tyr Glu Ile Gly Ala Asp Lys
1               5                   10                  15

Thr Ala Thr Ile Glu Thr Ile Met Asn Leu Leu Gln Glu Thr Ala Leu
            20                  25                  30
```

```
Asn His Val Lys Ser Ala Gly Leu Leu Gly Asp Gly Phe Gly Ala Thr
         35                  40                  45

Pro Glu Met Xaa Lys Lys Asn Leu Ile Trp Val Val Thr Arg Met Gln
     50                  55                  60

Val Val Val Asp Lys Tyr Pro Thr Trp Gly Asp Val Val Glu Val Asp
 65                  70                  75                  80

Thr Trp Val Ser Ala Ser Gly Lys Asn Gly Met Arg Arg Asp Trp Ile
                 85                  90                  95

Leu Arg Asp Xaa Xaa Thr Gly Glu Ile Ile Thr Arg Ala Thr Ser Xaa
                100                 105                 110

Trp Val Met Met Asn Xaa Asp Thr Arg Arg Leu Ser Lys Ile Pro Glu
                115                 120                 125

Glu Val Arg Gln Glu Ile Leu Pro Phe Phe
    130                 135
```

<210> SEQ ID NO 17
<211> LENGTH: 2000
<212> TYPE: DNA
<213> ORGANISM: Glycine max

<400> SEQUENCE: 17

```
gtagtttagg gtacacatga ggtcataata tgaggttttc ttatttgaaa gttaccttca      60
atagcattac tttcttgttt ttgttttgtt ttttgcggaa tattatatta aaactccttt     120
ttttcaaatt gtctattaaa atcaaattgt ttgattttat ttcataattg aattattttg     180
aaactacaac tgatccttcg agtatgatat ctagacttag gttcattgtt actcccacat     240
atgttacgtt tgcccttagt acaactaaca tctaatgtgt tagtacccat taataagtgt     300
tcccacatta gctacaagtg ctaagaaaac actttcatca taaatatat gattaagtta      360
tagaaactta atccaaacaa gaatgccatc aattttgct tccagtgaga tggatgaagg      420
ggaccatgtt tgcactcata gataatcatc aaagatcatg cattgtcctt gctgcatgac     480
cttactttag tcatactcct catcaattaa ccatacaaaa atctaatatg ttcatttaaa     540
aatcaaatat acccaaaggt tcaaaattgt ttctcacggt gaaaggtttt tttttcggtt     600
ttttattga ttttgatagt tttaattgt cttaaattat aattttaaat ttaaaataaa       660
tagtattaat tttgagcca caattaaaat ttgtaactat catatcatca tttgtcatat      720
catcacttaa atgacaataa aaatctaaaa gaaattttt tatcataact caatgcaatt      780
tttttatca agaattcaaa gcaaaattca aaatttata agggatctaa aagttattta      840
agtttttttt tttcaatttt tttcctaaat ccctctctat atgatatatt atcttatact     900
tgtaatatca actaaacaca ttataacctt ctcgtctctt ttaatttatc atgttcaata    960
tttttattt taacttgaat ttcattttt taaattttaa taattaaaat aacaatataa       1020
attattgatc ataaatttta aatataattt acttgtttag aaatatttat ttattacata    1080
ttttaattat aatataattt atatattttg aaatattttt cattataaat tttagatctt    1140
aaatgtatta aagaatgatt tactttatat gatacaaaga ctaaaactct actatttata    1200
attttataaa gtaactaata ttttagccaa tgcattgcaa accataaaat atttattta     1260
tataactaaa aattatagtt tattataaat aataattta aatatataaa ttatattata     1320
attgtaattt gtaataaatc aatattttta atatactaca taagttatat tttagattat    1380
cataattttt cttaaaaaat gttttaaatt aaatctttcg aaacatttaa attaaagtta    1440
aaataaaata ttttgagtaa tagattaaaa aagataaaat aattaagtta aattgtttag    1500
```

```
ttgatatttt tttaaaagga atcatttagt tggtattgta aataaaggaa agtagctatg    1560
caggaggaaa aagtaaaaca agtaatttaa ttacaattta ttatgtttga taaatttatt    1620
taaaataatt caaacaataa tttataatta aataataata taaaattatt ttacacatat    1680
taatacatat acattaaact cttaaaagtt taaaaagaat atatcatgga caagaagagt    1740
aaagttgctc ctcataaaac aagagtattc aaaatttgaa atgagactta agaagcagta    1800
tatatatata tatatatata tatatatata tatatatata tatatatata tatatatata    1860
tatatatata tatatatata tattttcttt ttttttatt ttatttattt atttatttat     1920
tttttaaaac aaacatcgat ttaatcgttg gacggttaaa aagttgaaga agacaaggga    1980
ggtttggttt ggtggaaaac                                                2000

<210> SEQ ID NO 18
<211> LENGTH: 6750
<212> TYPE: DNA
<213> ORGANISM: Glycine max
<220> FEATURE:
<221> NAME/KEY: 5'UTR
<222> LOCATION: (1)..(220)
<220> FEATURE:
<221> NAME/KEY: 3'UTR
<222> LOCATION: (6365)..(6750)

<400> SEQUENCE: 18
agaaataaaa aaagaaaaag agcaccatcg agaacacgtg cttcattcac cacttcagtg      60
tcgcttccca tctctatctc ttcgacaacg tcgttcgatt caaaaccact tgtttgttgc     120
actccgcctc ttccccttct ttctcattct catacgcacc cagtcaccca gctttccctt     180 tttcctatttt ttttttctctt tttttattaa aaaaataaaa atgttgaagc tttcgtgcaa   240
tggcttggac cgggctcact ccctggccca atgcggcttc gcggccggc ccgcctgcgc      300 cgtccctcgc cggaggagga gcggcgtctc cggattccgg ttgccggaag gcaggtcgat     360
ccgggtgtcc gcggcggtgt cggcaaagga cggcgcggtg gcgacccggg tagaggcgga    420
tcccggtacg ctggcggacc ggctgagggt ggggagcttg acggaggatg ggttgtctta    480
taaggagaag ttcattgtga ggagctacga agttgggatc aataagactg ccactgttga    540
aaccattgcc aatctcttgc aggtcctgat ttttttgtttg tttgtttaaa ttgggtgatt   600
tcatttgatt tgattgcttc atcttgttta attgggtgat tgattgggat tttgagcatc    660
ttggtgtttc tggaatggga aatgggattt ctttttttctg tttcttaagt gaaaaatgaa    720
tttttttttt tggcaactgg ggttgttttg ctttgactaa aactgttttg aagtttacaa    780
attgaagatt tgtaccattc gaggttgttt tgtgtactat gttttatag ctttatggtt     840 ttgctgtttt gtgccaattt tagtagtcca gatttggagg cactgagttc catgcatgga    900
gtgttggagt ttgtagtata agattttgga gaagtgtgct ttgttttctt cttcgtgctt    960
cttttttgta ttagtactaa atttgttcc ttgatttaa ctctctgatt cagaataatt     1020
gtcatattaa aaattcgtac tcttattct agtcttgatc ttgtgaaaat gctataaact    1080 tcttttttatt atattatcctt cttggtattt ctttaatgct ctcttaatga tttgctcatt  1140
gtaataccat tgttgcatcc caggtttgag acaaggcagt cccttgactc atcaaaacca   1200
aaagatgaaa atcagtagga aaatataatt gatttttttt atttctaaa gtatcaaata    1260 aatttggatg tcttttagag actgttgaat aaacaaaaaa gaagatagat ctcaccttag   1320
gaactgaatt tatctaatgt gaagagcatg tgctattgta ttcttcaaac tcaaatgaat   1380
```

```
tttgaaatgt tgggcgactt tgtgttatag gaggttggat gtaatcatgc tcagagtgtt    1440
ggatattcta ctgatggttt tgcaaccacc cctacgatga gaaaattgcg tctcatatgg    1500
gttactgctc gcatgcacat tgaaatctac aaatacactg cttggttggt ttttgttctt    1560
tataacactc ggtttataaa ctctaatttg aaaagtctaa cttaaatgat tccaacagga    1620
gtgacattgt tgagatagag acatggtgcc aaggggaagg aagggttggg acaaggcgtg    1680
attttatact gaaagactat gcaactgatg aagttattgg aagggcaaca aggtaaagat    1740
tttccattat gcactataat ctatcgagtt ttttctggcg tggctccttt cgggtcttaa    1800
atggcagatc aattgttaac aatcagatat atatgcttac tttgtgtagg actaggatga    1860
tatttgacca ttctttgatt tctgggcaac cttgtagagg acccatcacg agcttttcct    1920
tttgatctct tttgttcttg taaaatctct ttcctcattt gagctcatga tagtttcttt    1980
tggtaccaac caaccattaa tgataagcct atataatata acctatgcta tttagtggca    2040
aaaaggatag gaaggatagg agactaaact actggttatt acaattaatc ctcaagtcac    2100
attacaagga tgctcgggat tttataaaag cataaagctc agaagcaata ctgtcccaaa    2160
atctaaattt gacagaaaat tatccattga tgcaaatcaa gatacattaa caattagttc    2220
atttgcatca taaattggtg catctgtaaa ttttgacatg tttatgtttt gttgcataca    2280
atagctatac tgtctgaaat aatttgtttt agatactttc ttatagttga ctatttatat    2340
ttaattgttt cagcaaatgg gtaatgatga atcaggacac cagacgactc cagaaggttt    2400
ctgatgatgt taaagaagag tatttggttt tctgtcctcg agagcccagg tagtcacttt    2460
tctttatcat ttgctgccaa tgcattacaa cttactcaaa ctttgttaga cgatttgttt    2520
tatttaggtg ttcttaatca ttgtagtaat aacaagactt gataagcaga agagatcaaa    2580
ctttctggga tttcttagct cactagtgca aagagggtta cactacttga tcaatattct    2640 atattttat ggattctgga ataaactaaa ttatagcata tgatcttgca tgcatcaata    2700
gtacattttg aaatgacttc ttacaacttt tatttggtag gagggaggag cctaccagct    2760
tgatataatt tgtgataaac tgcagtgcag gttgttaatt gccatttact aggtagtaag    2820
tgaggcatca ctaatgagga tgtcattaga tggtcaagta aaatctggga cacgtgttcg    2880
catatttatg tagcctatat atttgaaatc acttttgcca gtttcaagat tcaagcttta    2940
ttaattgggt gagaatggtc ttttgggggg aggggtatag gttgagggag gatgaaaggt    3000
ggagaactat taccaaaaga acaaaagttg agcacccctc caacccaact atattaatgt    3060
gttatgttat gctgcccaat tgttttttgtt ggaattgtgg gagttaatgt atcattgcaa    3120
agatcagagt cgaagtgaat agtttaattc cttattattg ttttttgtaat tgtaaaatgt    3180 atttattctt ttatgcatgt aaatatcaag gatgctgagt actccctctc aagtaattca    3240
tgagacttct atctaatttc tacaataaag tatctcaagt ttattgtatg tgtgtgtagg    3300
ataaattaat ctcacctccc ttgaggtata atgatacacc aatatcgctc tcttttttga    3360
cattgcatac actgcctcaa tacatataac aatataaaat ataacagaag gcctgtgtta    3420
aggttaaggg tacatggcgt tatgttatat aaattgaggg aggtttgtgt tggatcatgg    3480
atgaaaagaa aacaagggat attgcgtata atattgataa acttctggtt gtgtgagtgt    3540
aatttgtcac acacacacat atttaaagaa atattatttc ttgattggta cttaaacatt    3600
tccagaagga agtttcacca ttaaaataaa tcaaaatgta ggtatacaag tatcattttt    3660 tcatacccctc cctctctgtg ttatagattt cttgaaaata tgatttagcc taggattata    3720
gtttatgtgt atttaaatga gggaaaataa ggagacagga tttggagtcc atctcgttgg    3780
```

```
acagaaacct agatagatca gtgatcagaa ttcctgttct aaactgaaaa caactctgta    3840
gatgttatct taatttacct cactaaaaca tatggagaac cactatttga agagcatccc    3900
acataattct agaactgact gaactctttc tgaacttaat gaccttttgg ttttttatca    3960
actgcccttg attacggact cctagcagtg aaaatagctg ttttcatcac ttcataatta    4020
agaatcacta ttgctaatct gtagaattct taattgacaa ataaaggaga attaacagca    4080
tcaccatcat tgttattcat atctaattgt tgaaattgtg atatcatttc catcaacaac    4140
acaaacttag attctattac tttcagcggc ttctgccact tccctctttt aggaaaggat    4200
gtgaggaagt tcatagtga tttctgataa aattgtggga acttactaca aacactatct    4260
tccattattt tagaaatgag tcttcctata aaagattcat agttttctt tggtaattgc     4320 caattggtac aaaaattgac ttgaacaatt tttttctggc ttagttagca tgctacaagt    4380
agcttggttg aattattagg gctgaatgat cataccgcat tgcttgtctt gttactgtta    4440
ctgttagtga cttggtgggt ttcaaatttc aatacccctgg ctggattgcg gcttaacttg    4500
tgattttatt ttctttgtcc aaatcttctt ctgtggtttt aggttagcta ttccagaggc    4560
agatagtaat agcttgaaga aaataccaaa attggaagac cctgctcagt attccagact    4620
tggacttgtg gtatgatcat ttgcctcagt gaaccttttt ctgttatttt cttttttccct   4680 ttttaacagg cacaaggaa ggaattttat tggtgataaa atagtggca aatccagcat      4740 atttcaattt tcaagagcct ggccttctca ttgtgctttt tattttgcag ccaagaagag    4800
cggatctgga catgaatcag catgttaaca atgtcaccta tattggatgg gtgcttgagg    4860
ttgttggatt gtcttttta ttaattgaaa tactatctat ttcatgtttt agctagttta     4920
tttgtcacaa aatcatcttt tggataaaca gtttatatca tgttctcatt taatttaca    4980 ttcatgaaat ctttatatct caaggtgcaa tgttttcaaa attaagaaaa tatcaattac    5040
ttgattgcat acttcatact tgatatgttc aattttctg atgtttggca tcttagatca     5100
aaagcacaat tattaataat tcaatggtcg gactgacaaa atttacatta gatgttctta    5160
cttgatatgt ttcctatata cttttatgca tttaatcctt tttttttcaa tattttgga    5220 tacttgtatg tgtgttattt cttccaaatg gcatgtactg tcacttgcat ttcataattc    5280
actaatattg gttctacttt tcactagaat atttgccatt tcttagatat gctagtgttg    5340
ctttgaattt gttagttata atttttcttt catgttcaac acccagaaaa aacatggttt    5400
tgacacattt ctaaaatcaa gattggcttt tgcaaacaag taataaaaat gtgtattaat    5460
ttagatctaa atgaaaaaga aaatgaggct atatgtttaa tgtataagct gataatttaa    5520
gcagtttaaa taaactgttt taaaaaacaa tcaattgaaa ttttttcatca agaagtggtc    5580 tgtgtaccat tcttttgaca aaaatccatg gttttgaata ttttggagc aacctatcta     5640 atatatatct gttgctggat tactggaaac taatttaatt gaggtcatgc tgggtcaact    5700
ttttttatct ttaatttttt agccttggct aaagttgaca ttaatgatag tcagctgttt    5760
agaccttaga tgtacaatta gaaatacaat ggtgttgata taatgatatt attatcatat    5820
ctacatgatg ttaaaataac cagtgaatta gaattggaaa taatgacaga caggaagatg    5880
ctttaaatac tgttttgtat aaatgaattt tcatgcactt catttgattt ggaatttttt    5940 tttttttctcc tcttctggtt tgttgcttat tctataatca cccttgtcat aaataacata    6000
catgtgacct atattatcaa tttttatgta gaaaaatgtc ttatcatgtt gatgtcacta    6060
acatactgtc ttactttatc agagcatgcc tcaagaaatc attgatagcc atgagttgca    6120
```

```
gagtattacc ttggattaca gacgagagtg cggacaacat gacatagtcg attccctcac      6180
tagtgtggaa gcgatacagg gtggtgccga ggcagttcca gaactgaaag gtacaaatgg      6240
atctgccacg gcaagggaag acaaacatga acaccagcag tttctgcatc tacttaggtt      6300
gtctactgaa ggacttgaga taaaccgggg acgaacagaa tggagaaaga aagctccaag      6360
atgagaacca ttatgtgtgc ttccacccga atccatgatt ctgttttttgt cttgtgttgt     6420 ttcatgttac cagggttgtc ttatcaattt tcccttgata ttttgcttag agtttgtgcg      6480
cttaataggg attgaagagt taaaatattg cttctgtttt cttgtcatgc tcaaaaattt      6540
aagttgtcca aatcccgtag ttaggctata taggttgaca tcaatctctg atccattagt      6600
atcagattcc atgaatgtca ttgtacctta agggagcata gaaatccagg aagttggtat      6660
ggatctgcca tctactgcat gacttgaaca atgtgtgtta aataatcat tttgaaataa       6720 ttcaattagc taattattaa tgttcttact                                       6750

<210> SEQ ID NO 19
<211> LENGTH: 1125
<212> TYPE: DNA
<213> ORGANISM: Glycine max
<220> FEATURE:
<221> NAME/KEY: mutation
<222> LOCATION: (110)..(110)
<223> OTHER INFORMATION: Sequence can be mutated from C to T.
<220> FEATURE:
<221> NAME/KEY: mutation
<222> LOCATION: (163)..(163)
<223> OTHER INFORMATION: Sequence can be mutated from G to T.
<220> FEATURE:
<221> NAME/KEY: mutation
<222> LOCATION: (437)..(437)
<223> OTHER INFORMATION: Sequence can be mutated from C to T.
<220> FEATURE:
<221> NAME/KEY: mutation
<222> LOCATION: (692)..(692)
<223> OTHER INFORMATION: Sequence can be mutated from C to T.
<220> FEATURE:
<221> NAME/KEY: mutation
<222> LOCATION: (830)..(830)
<223> OTHER INFORMATION: Sequence can be mutated from G to A.
<220> FEATURE:
<221> NAME/KEY: mutation
<222> LOCATION: (928)..(928)
<223> OTHER INFORMATION: Sequence can be mutated from G to A.

<400> SEQUENCE: 19
atgttgaagc tttcgtgcaa tggcttggac cgggctcact ccctggccca atgcggcttc       60
gcgggccggc ccgcctgcgc cgtccctcgc cggaggagga gcggcgtctc cggattccgg      120
ttgccggaag gcaggtcgat ccgggtgtcc gcggcggtgt cggcaaagga cggcgcggtg      180
gcgacccggg tagaggcgga tcccggtacg ctggcggacc ggctgagggt ggggagcttg      240
acggaggatg ggttgtctta taaggagaag ttcattgtga ggagctacga agttgggatc      300
aataagactg ccactgttga aaccattgcc aatctcttgc aggaggttgg atgtaatcat      360
gctcagagtg ttggatattc tactgatggt tttgcaacca cccctacgat gagaaaattg      420
cgtctcatat gggttactgc tcgcatgcac attgaaatct acaaataccc tgcttggagt      480
gacattgttg agatagagac atggtgccaa ggggaaggaa gggttgggac aaggcgtgat      540
tttatactga aagactatgc aactgatgaa gttattggaa gggcaacaag caaatgggta      600
atgatgaatc aggacaccag acgactccaa aaggtttctg atgatgttaa agaagagtat      660 ttggtttttct gtcctcgaga gcccaggtta gctattccag aggcagatag taatagcttg      720
aagaaaatac caaaattgga agaccctgct cagtattcca gacttggact tgtgccaaga      780
```

```
agagcggatc tggacatgaa tcagcatgtt aacaatgtca cctatattgg atgggtgctt    840
gagagcatgc ctcaagaaat cattgatagc catgagttgc agagtattac cttggattac    900
agacgagagt gcggacaaca tgacatagtc gattccctca ctagtgtgga agcgatacag    960
ggtggtgccg aggcagttcc agaactgaaa ggtacaaatg gatctgccac ggcaagggaa   1020
gacaaacatg aacaccagca gtttctgcat ctacttaggt tgtctactga aggacttgag   1080
ataaaccggg gacgaacaga atggagaaag aaagctccaa gatga                   1125
```

<210> SEQ ID NO 20
<211> LENGTH: 374
<212> TYPE: PRT
<213> ORGANISM: Glycine max
<220> FEATURE:
<221> NAME/KEY: MUTAGEN
<222> LOCATION: (37)..(37)
<223> OTHER INFORMATION: Sequence can be mutated from Ser to Phe.
<220> FEATURE:
<221> NAME/KEY: MUTAGEN
<222> LOCATION: (55)..(55)
<223> OTHER INFORMATION: Sequence can be mutated from Ala to Thr.
<220> FEATURE:
<221> NAME/KEY: MUTAGEN
<222> LOCATION: (146)..(146)
<223> OTHER INFORMATION: Sequence can be mutated from Thr to Ile.
<220> FEATURE:
<221> NAME/KEY: MUTAGEN
<222> LOCATION: (231)..(231)
<223> OTHER INFORMATION: Sequence can be mutated from Ala to Val.
<220> FEATURE:
<221> NAME/KEY: MUTAGEN
<222> LOCATION: (277)..(277)
<223> OTHER INFORMATION: Sequence can be mutated from Gly to Glu.
<220> FEATURE:
<221> NAME/KEY: MUTAGEN
<222> LOCATION: (310)..(310)
<223> OTHER INFORMATION: Sequence can be mutated from Val to Ile.

<400> SEQUENCE: 20

Met Leu Lys Leu Ser Cys Asn Gly Leu Asp Arg Ala His Ser Leu Ala
1               5                   10                  15

Gln Cys Gly Phe Ala Gly Arg Pro Ala Cys Ala Val Pro Arg Arg Arg
            20                  25                  30

Arg Ser Gly Val Ser Gly Phe Arg Leu Pro Glu Gly Arg Ser Ile Arg
        35                  40                  45

Val Ser Ala Ala Val Ser Ala Lys Asp Gly Ala Val Ala Thr Arg Val
    50                  55                  60

Glu Ala Asp Pro Gly Thr Leu Ala Asp Arg Leu Arg Val Gly Ser Leu
65                  70                  75                  80

Thr Glu Asp Gly Leu Ser Tyr Lys Glu Lys Phe Ile Val Arg Ser Tyr
                85                  90                  95

Glu Val Gly Ile Asn Lys Thr Ala Thr Val Glu Thr Ile Ala Asn Leu
            100                 105                 110

Leu Gln Glu Val Gly Cys Asn His Ala Gln Ser Val Gly Tyr Ser Thr
        115                 120                 125

Asp Gly Phe Ala Thr Thr Pro Thr Met Arg Lys Leu Arg Leu Ile Trp
    130                 135                 140

Val Thr Ala Arg Met His Ile Glu Ile Tyr Lys Tyr Pro Ala Trp Ser
145                 150                 155                 160

Asp Ile Val Glu Ile Glu Thr Trp Cys Gln Gly Glu Gly Arg Val Gly
                165                 170                 175

Thr Arg Arg Asp Phe Ile Leu Lys Asp Tyr Ala Thr Asp Glu Val Ile

```
            180                 185                 190
Gly Arg Ala Thr Ser Lys Trp Val Met Met Asn Gln Asp Thr Arg Arg
        195                 200                 205

Leu Gln Lys Val Ser Asp Asp Val Lys Glu Glu Tyr Leu Val Phe Cys
    210                 215                 220

Pro Arg Glu Pro Arg Leu Ala Ile Pro Glu Ala Asp Ser Asn Ser Leu
225                 230                 235                 240

Lys Lys Ile Pro Lys Leu Glu Asp Pro Ala Gln Tyr Ser Arg Leu Gly
                245                 250                 255

Leu Val Pro Arg Arg Ala Asp Leu Asp Met Asn Gln His Val Asn Asn
            260                 265                 270

Val Thr Tyr Ile Gly Trp Val Leu Glu Ser Met Pro Gln Glu Ile Ile
        275                 280                 285

Asp Ser His Glu Leu Gln Ser Ile Thr Leu Asp Tyr Arg Arg Glu Cys
    290                 295                 300

Gly Gln His Asp Ile Val Asp Ser Leu Thr Ser Val Glu Ala Ile Gln
305                 310                 315                 320

Gly Gly Ala Glu Ala Val Pro Glu Leu Lys Gly Thr Asn Gly Ser Ala
                325                 330                 335

Thr Ala Arg Glu Asp Lys His Glu His Gln Gln Phe Leu His Leu Leu
            340                 345                 350

Arg Leu Ser Thr Glu Gly Leu Glu Ile Asn Arg Gly Arg Thr Glu Trp
        355                 360                 365

Arg Lys Lys Ala Pro Arg
    370
```

<210> SEQ ID NO 21
<211> LENGTH: 2000
<212> TYPE: DNA
<213> ORGANISM: Glycine max

<400> SEQUENCE: 21

```
gaaaaagaaa attccaacta atcaactgta tcgcttatag atcatattaa tttctgtgtg      60
tttggatgta aaattcattt gaggagtgat agtaatatat ttttattgg ttaaaatata     120
ttaaaaattg cataattagg tgagagagtc attaaataag atttgatatc cacttaattt    180
tgtaaatttt aataaatttt aatcaaagaa agagtaacta taatatttct taattaattt    240
tgattaaaat tcattttaaa gtcatataat tcaagtttag attttttatt ataaaaacaa    300
aaattagtag tagcacttaa ttaatgtaat ttttttatc aaacacaaaa tagttaaaat     360
tattttaagt cataattaat tactcaacgt gaactaaaaa attattaaat atatatagcg    420
ttaaccaacg gataaaatct gataaccaaa cctaagtcgc tactcatgtg agggaaaaat    480
ttaataagat gtatcaattt gttgacggtg tgaaacatgc atgtattatg gaaaaaaaaa    540
atataatcat aaaaaattac cttatttatg atattattat tttctttaat tgctcgacaa    600
tagatacata atttttttac atattttttt tctcaaaatt atttaacaaa aagtgaataa    660
aaaatgtaat gcataaaaga tgttgaaagt agtttaaaaa tatgtccatt taacatgcta    720
atgtccgtaa gatgatatat agagcataat attagtagtg acaattataa aatactccga    780
aaatgcataa aactattcga acacataaac ctaatgagtg taacaaatcc aggatacatc    840
gatttgagat gctattttcg ctagaacgtt taataataat aataataaat atataacacg    900
tttagaaact aatgcagtat taattaacaa ctaattctat aacagacacg aagaaaatgg    960
tgcaaatttc aaacacaatt aaattatatg ttcaacttaa aaatttaaat acaaataata   1020
```

```
tttaaaatgg tttaaattta atttgaaata atatatgtga aaaattagat taaactatat    1080
ttattgtata agagatattt aagtcggaaa aaaatagagg aatgctaaat taattaggta    1140
aataaattac aaatatttag ataaaatacg aaattcagta tattaattac gcgaaaagct    1200 aaaaagtta aataaaaata taataaaagg ttaaattata ttttttctc ctatgaaaat      1260 attcgaaatt cattcatgtg aaattttag tatatttttt atttacataa aattaaaatt     1320
tattattttt tacctagata taatcttgag taaatttaaa cttatggtga tgattttata    1380
tctatgaaaa atgtgatttt ttttatattg gtggttacaa ccaatataaa aataatac a    1440 aataagttca aatatttaaa tcttactggg gttaaaaatt gacacgtttc aatttttataa   1500 acatgaaaaa tattcttgaa aatttttaaaa aacaaatttt gaatattttt atatttatga   1560
taattaaaaa tatattttaa tctaataaaa atgcattaaa aaagaatagt agctaatata    1620
taaaattaaa attctaaagt agaaaaaaaa gattaaacct tattttatc gagtaaactt     1680 gatagagata aataatgata cgtggtggtg gggtgattac aaaatgtctt aatcttttat    1740
tgtgaaagaa atattctatt gtgaataaaa aaaaaaaccc aatgtcttta tcttttactt    1800
ggaaaatgaa aaaaaaaaaa aaaactctgt aaaatcccgt gggtactggc attactagga   1860
gagtatggcc gaaataaggg gggcaatacg gtaaagagg gaagagacta gctgggatct     1920
ttgaaagggc ggcgggaggg ccagctggac agtataaaaa gaagtggctg gaatgctaat   1980
gccttatccc taactcataa                                                2000

<210> SEQ ID NO 22
<211> LENGTH: 4195
<212> TYPE: DNA
<213> ORGANISM: Glycine max
<220> FEATURE:
<221> NAME/KEY: 5'UTR
<222> LOCATION: (1)..(136)
<220> FEATURE:
<221> NAME/KEY: 5'UTR
<222> LOCATION: (246)..(319)
<220> FEATURE:
<221> NAME/KEY: 5'UTR
<222> LOCATION: (1156)..(1173)
<220> FEATURE:
<221> NAME/KEY: 3'UTR
<222> LOCATION: (3702)..(4195)

<400> SEQUENCE: 22
cacaattaca ctgtctctct cttttccaaa attagggaaa caacaaggac gcaaaatgac    60
acaatagccc ttcttccctg tttccagctt ttctccttct ctctctccat cttcttcttc    120
ttcttcactc agtcaggtac gcaaacaaat ctgctattca ttcattcatt cctctttctc    180
tctgatcgca aactgcacct ctacgctcca ctcttctcat tttctcttcc tttctcgctt    240
ctcagatcca actcctcaga taacacaaga ccaaacccgc ttttttctgca tttctagact    300 agacgttcta ccggagaagg ttctcgattc ttttctcttt taactttatt tttaaaataa    360
taataatgag agctggatgc gtctgttcgt tgtgaatttc gaggcaatgg ggttctcatt    420
ttcgttacag ttacagattg cattgtctgc tttcctcttc tcccttgttt ctttgccttg    480
tctgattttt cgtttttatt tcttactttt aattttgggg gatggatgtt ttttctgcat    540
tttttcggtt tgcgatgttt tcaggattcc gattccgagt cagatctgcg ccggcttata    600
cgacgaattt gttcttattc gcaacttttc gcttgattgg cttgttttac ctctggaatc    660
tcacacgtga tcaaataagc ctgctatttt agttgaagta gaatttgttc tttatcggaa    720
```

```
agaattctat ggatctgttc tgaaattgga gctactgttt cgagttgcta ttttttttag      780
tagtattaag aacaagtttg ccttttattt tacattttt tcctttgctt ttgccaaaag        840
tttttatgat cactctcttc tgtttgtgat ataactgatg tgctgtgctg ttattatttg      900
ttatttgggg tgaagtataa ttttttgggt gaacttggag cattttagt ccgattgatt       960 tctcgatatc atttaaggct aaggttgacc tctaccacgc gtttgcgttt gatgtttttt      1020
ccattttttt tttatctcat atcttttaca gtgtttgcct atttgcattt ctcttcttta      1080 tccccttct gtggaaggtg ggagggaaaa tgtatttttt ttttctcttc taacttgcgt       1140
atattttgca tgcagcgacc ttagaaattc attatggtgg caacagctgc tacttcatca      1200
tttttccctg ttacttcacc ctcgccggac tctggtggag caggcagcaa acttggtggt      1260
gggcctgcaa accttggagg actaaaatcc aaatctgcgt cttctggtgg cttgaaggca      1320
aaggcgcaag ccccttcgaa aattaatgga accacagttg ttacatctaa agaaagcttc      1380
aagcatgatg atgatctacc ttcgcctccc cccagaactt ttatcaacca gttgcctgat      1440
tggagcatgc ttcttgctgc tatcacaaca attttcttgg ccgctgaaaa gcagtggatg      1500
atgcttgatt ggaagccacg gcgacctgac atgcttattg ccccctttgg gataggaaaa      1560
attgttcagg atggtcttgt gttccgtgaa aacttttcta ttagatcata tgagattggt      1620
gctgatcgta ccgcatctat agaaacagta atgaaccatt gcaagtaag tccgtcctca       1680 tacaagtgaa tctttatgat cttcagagat gagtatgctt tgactaagat agggctgttt      1740
atttagtcac tgtaattcaa tttcatatat agataatatc attctgttgt tacttttcat      1800
actatattta tatcaactat ttgcttaaca acaggaaact gcacttaatc atgttaaaag      1860
tgctgggctt cttggtgatg gctttggttc cacgccagaa atgtgcaaaa agaacttgat      1920
atgggtggtt actcggatgc aggttgtggt ggaacgctat cctacatggt tagtcatcta      1980
gattcaacca ttacatgtga tttgcaatgt atccatgtta agctgctatt tctctgtcta      2040
ttttagtaat ctttatgagg aatgatcact cctaaatata ttcatggtaa ttattgagac      2100
ttaattatga gaaccaaaat gctttggaaa tttgtctggg atgaaaattg attagataca      2160
caagctttat acatgatgaa ctatgggaaa ccttgtgcaa cagagctatt gatctgtaca      2220
agagatgtag tatagcatta attacatgtt attagataag gtgacttatc cttgtttaat      2280
tattgtaaaa atagaagctg atactatgta ttctttgcat ttgttttctt accagttata      2340
tataccctct gttctgtttg agtactacta gatgtataaa gaatgcaatt attctgactt      2400
cttggtgttg ggttgaagtt agataagcta ttagtattat tatggttatt ctaaatctaa      2460
ttatctgaaa ttgtgtgtct atatttgctt caggggtgac atagttcaag tggacacttg      2520
ggtttctgga tcaggaaga atggtatgcg ccgtgattgg cttttacgtg actgcaaaac       2580
tggtgaaatc ttgacaagag cttccaggta gaaatcattc tctggaattt tccttcccct      2640
ttccttctgc ttcaagcaaa ttttaagatg tgtatcttaa tgtacttgat ggtgattggg      2700
cacaattttg aatcttccat acattttaaa agttatggaa ccctttcttt tccttcttaa      2760
gatgcaaatt tgtcatgact gaagtttcag gtaatcattt gcattttgca gtgttaaaaa      2820
agataatgaa ctacacattt attatatttt gcaggcaaaa acctctaatt aaacaaactg      2880
aacattgtat cttagtttat ttatcagact ttatcatgtg tactgatgca tcaccttgga      2940
gcttgtaatg aattacatat tagtattttc tgaactgttt gttatggttt tggtgatcta      3000
cagtgtttgg gtcatgatga ataagctaac acgaggctct ctaaaattc cagaagaagt       3060 cagacaggag ataggatctt atttttgtgga ttctgatcca attctggaag aggataacag     3120
```

```
aaaactgact aaacttgacg acaacacagc ggattatatt cgtaccggtt taagtgtatg   3180
tcaactagtt ttttttctaa ttgctgtcat taatttattt tctcaaatta tttcagatgt   3240
tgttttctaa ttagtttaca taatgcatct tcattttgca gcctaggtgg agtgatctag   3300
atatcaatca gcatgtcaac aatgtgaagt acattggctg gattctggag gtattttttct  3360 gttcttgtat tctaatcaac tgcaatccat gttagttctt taaccaaagg actgtctttt   3420
gattgttgca gagtgctcca cagccaatct tggagagtca tgagctttct tccatgactt   3480
tagagtatag gagagagtgt ggtagggaca gtgtgctgga ttccctgact gctgtatctg   3540
gggccgacat gggcaatcta gctcacagcg ggcatgttga gtgcaagcat ttgcttcgac   3600
tggaaaatgg tgctgagatt gtgaggggca ggactgagtg gaggcccaaa cctgtgaaca   3660
actttggtgt tgtgaaccag gttccagcag aaagcaccta agattttgaa atggttaacg   3720
attggagttg catcagtctc cttgctatgt ttagacttat tctggtccct ggggagagtt   3780
ttgcttgtgt ctatccaatc aatctacatg tctttatata tatacacctt ctaatttgtg   3840
atactttggt gggtaagggg gaaaagcagc agtaaatctc attctcattg taattagcta   3900
ctgctgtatt ctctctttct gctgctccat atttcatttc atctctgatt gcgctactgc   3960
taggctgtct tcaatatttta attgcttgtt caaaatagct aggcatgtat attattattc   4020
tttttctctt ggcccaatta aagatgcaat tttccttgtg aacacagcat aattcttatt   4080
cttatttatt tttgtatatc ctgtatgcaa gaatgacttg tcctccaata caactgtgat   4140
tttgtatgct ccagcttgta ttttatgcca gcttcccaca tgggaattat tgtgc         4195
```

<210> SEQ ID NO 23
<211> LENGTH: 1251
<212> TYPE: DNA
<213> ORGANISM: Glycine max
<220> FEATURE:
<221> NAME/KEY: mutation
<222> LOCATION: (52)..(52)
<223> OTHER INFORMATION: Sequence can be mutated from C to T.
<220> FEATURE:
<221> NAME/KEY: mutation
<222> LOCATION: (382)..(382)
<223> OTHER INFORMATION: Sequence can be mutated from G to A.
<220> FEATURE:
<221> NAME/KEY: mutation
<222> LOCATION: (539)..(539)
<223> OTHER INFORMATION: Sequence can be mutated from G to A.
<220> FEATURE:
<221> NAME/KEY: mutation
<222> LOCATION: (668)..(668)
<223> OTHER INFORMATION: Sequence can be mutated from G to A.
<220> FEATURE:
<221> NAME/KEY: mutation
<222> LOCATION: (850)..(850)
<223> OTHER INFORMATION: Sequence can be mutated from G to A.
<220> FEATURE:
<221> NAME/KEY: mutation
<222> LOCATION: (1111)..(1111)
<223> OTHER INFORMATION: Sequence can be mutated from G to A.

<400> SEQUENCE: 23

```
atggtggcaa cagctgctac ttcatcattt ttccctgtta cttcaccctc gccggactct     60
ggtggagcag gcagcaaact tggtggtggg cctgcaaacc ttggaggact aaaatccaaa    120
tctgcgtctt ctggtggctt gaaggcaaag gcgcaagccc cttcgaaaat taatggaacc    180
acagttgtta catctaaaga aagcttcaag catgatgatg atctaccttc gcctccccc     240 agaacttttta tcaaccagtt gcctgattgg agcatgcttc ttgctgctat cacaacaatt    300
```

```
ttcttggccg ctgaaaagca gtggatgatg cttgattgga agccacggcg acctgacatg    360
cttattgacc cctttgggat aggaaaaatt gttcaggatg gtcttgtgtt ccgtgaaaac    420
ttttctatta gatcatatga gattggtgct gatcgtaccg catctataga aacagtaatg    480
aaccatttgc aagaaactgc acttaatcat gttaaaagtg ctgggcttct tggtgatggc    540
tttggttcca cgccagaaat gtgcaaaaag aacttgatat gggtggttac tcggatgcag    600
gttgtggtgg aacgctatcc tacatggggt gacatagttc aagtggacac ttgggtttct    660
ggatcaggga agaatggtat gcgccgtgat tggcttttac gtgactgcaa aactggtgaa    720
atcttgacaa gagcttccag tgtttgggtc atgatgaata agctaacacg gaggctgtct    780
aaaattccag aagaagtcag acaggagata ggatcttatt ttgtggattc tgatccaatt    840
ctggaagagg ataacagaaa actgactaaa cttgacgaca cacagcgga ttatattcgt    900
accggtttaa gtcctaggtg gagtgatcta gatatcaatc agcatgtcaa caatgtgaag    960
tacattggct ggattctgga gagtgctcca cagccaatct tggagagtca tgagcttttct    1020
tccatgactt tagagtatag gagagagtgt ggtagggaca gtgtgctgga ttccctgact    1080
gctgtatctg gggccgacat gggcaatcta gctcacagcg ggcatgttga gtgcaagcat    1140
ttgcttcgac tggaaaatgg tgctgagatt gtgaggggca ggactgagtg gaggcccaaa    1200
cctgtgaaca actttggtgt tgtgaaccag gttccagcag aaagcaccta a            1251
```

<210> SEQ ID NO 24
<211> LENGTH: 416
<212> TYPE: PRT
<213> ORGANISM: Glycine max
<220> FEATURE:
<221> NAME/KEY: MUTAGEN
<222> LOCATION: (18)..(18)
<223> OTHER INFORMATION: Sequence can be mutated from Pro to Leu.
<220> FEATURE:
<221> NAME/KEY: MUTAGEN
<222> LOCATION: (128)..(128)
<223> OTHER INFORMATION: Sequence can be mutated from Gly to Arg.
<220> FEATURE:
<221> NAME/KEY: MUTAGEN
<222> LOCATION: (180)..(180)
<223> OTHER INFORMATION: Sequence can be mutated from Gly to Asp.
<220> FEATURE:
<221> NAME/KEY: MUTAGEN
<222> LOCATION: (223)..(223)
<223> OTHER INFORMATION: Sequence can be mutated from Gly to Glu.
<220> FEATURE:
<221> NAME/KEY: MUTAGEN
<222> LOCATION: (284)..(284)
<223> OTHER INFORMATION: Sequence can be mutated from Asp to Asn.
<220> FEATURE:
<221> NAME/KEY: MUTAGEN
<222> LOCATION: (371)..(371)
<223> OTHER INFORMATION: Sequence can be mutated from Ala to Thr.

<400> SEQUENCE: 24

```
Met Val Ala Thr Ala Ala Thr Ser Ser Phe Phe Pro Val Thr Ser Pro
1               5                   10                  15

Ser Pro Asp Ser Gly Gly Ala Gly Ser Lys Leu Gly Gly Gly Pro Ala
            20                  25                  30

Asn Leu Gly Gly Leu Lys Ser Lys Ser Ala Ser Ser Gly Gly Leu Lys
        35                  40                  45

Ala Lys Ala Gln Ala Pro Ser Lys Ile Asn Gly Thr Thr Val Val Thr
    50                  55                  60

Ser Lys Glu Ser Phe Lys His Asp Asp Asp Leu Pro Ser Pro Pro Pro
65                  70                  75                  80
```

```
Arg Thr Phe Ile Asn Gln Leu Pro Asp Trp Ser Met Leu Leu Ala Ala
                85                  90                  95

Ile Thr Thr Ile Phe Leu Ala Ala Glu Lys Gln Trp Met Met Leu Asp
            100                 105                 110

Trp Lys Pro Arg Arg Pro Asp Met Leu Ile Asp Pro Phe Gly Ile Gly
        115                 120                 125

Lys Ile Val Gln Asp Gly Leu Val Phe Arg Glu Asn Phe Ser Ile Arg
    130                 135                 140

Ser Tyr Glu Ile Gly Ala Asp Arg Thr Ala Ser Ile Glu Thr Val Met
145                 150                 155                 160

Asn His Leu Gln Glu Thr Ala Leu Asn His Val Lys Ser Ala Gly Leu
                165                 170                 175

Leu Gly Asp Gly Phe Gly Ser Thr Pro Glu Met Cys Lys Lys Asn Leu
            180                 185                 190

Ile Trp Val Val Thr Arg Met Gln Val Val Glu Arg Tyr Pro Thr
        195                 200                 205

Trp Gly Asp Ile Val Gln Val Asp Thr Trp Val Ser Gly Ser Gly Lys
    210                 215                 220

Asn Gly Met Arg Arg Asp Trp Leu Leu Arg Asp Cys Lys Thr Gly Glu
225                 230                 235                 240

Ile Leu Thr Arg Ala Ser Ser Val Trp Val Met Met Asn Lys Leu Thr
                245                 250                 255

Arg Arg Leu Ser Lys Ile Pro Glu Glu Val Arg Gln Glu Ile Gly Ser
            260                 265                 270

Tyr Phe Val Asp Ser Asp Pro Ile Leu Glu Glu Asp Asn Arg Lys Leu
        275                 280                 285

Thr Lys Leu Asp Asp Asn Thr Ala Asp Tyr Ile Arg Thr Gly Leu Ser
    290                 295                 300

Pro Arg Trp Ser Asp Leu Asp Ile Asn Gln His Val Asn Asn Val Lys
305                 310                 315                 320

Tyr Ile Gly Trp Ile Leu Glu Ser Ala Pro Gln Pro Ile Leu Glu Ser
                325                 330                 335

His Glu Leu Ser Ser Met Thr Leu Glu Tyr Arg Arg Glu Cys Gly Arg
            340                 345                 350

Asp Ser Val Leu Asp Ser Leu Thr Ala Val Ser Gly Ala Asp Met Gly
        355                 360                 365

Asn Leu Ala His Ser Gly His Val Glu Cys Lys His Leu Leu Arg Leu
    370                 375                 380

Glu Asn Gly Ala Glu Ile Val Arg Gly Arg Thr Glu Trp Arg Pro Lys
385                 390                 395                 400

Pro Val Asn Asn Phe Gly Val Val Asn Gln Val Pro Ala Glu Ser Thr
                405                 410                 415

<210> SEQ ID NO 25
<211> LENGTH: 2000
<212> TYPE: DNA
<213> ORGANISM: Glycine max

<400> SEQUENCE: 25
gatttgagat gctattttat cgattgacag cagcagcagt aataataata ataataataa      60
taataataat aataataata ataataataa taataataat gatgataata ataataataa     120
taatataact taacaactaa tgtagtatta gttccgtttc tttttataag aaaaataagt     180
tacattatat tttatacaaa taacttattt ttttataaat agaaaggat gtagtattaa      240
```

-continued

| | |
|---|---|
| ttaacaccta attctataac agacatgaag taaatgatgc aaaattccaa cacaatgaaa | 300 |
| gtatatgttc tattttaaaa aattaaataa aaataaaatt taaaatattt taaataataa | 360 |
| atttgaaaaa tagattaaat tagatttat tgtataagag atatttaagc tgaaaaaaat | 420 |
| gaggcgtact aaatttattg ggtaaagaaa ttacaaatat ttatataaaa tatgaaattc | 480 |
| agtatattaa ttaggtgtaa agctaaattt ttttaaaaaa aatgtattta tattaaaatt | 540 |
| ataataaaaa ggcattaaaa aagaaaagta actaatatct aaaaattcta aagtagaaaa | 600 |
| aataagatta aaccttatt ttatacagta attaatattc ttttcttct ttttataaat | 660 |
| taattttta aaccttcatt aaaatatata gaaacaataa aataagggtc tagcgtaaaa | 720 |
| aaaagtcatg agatgttttt ctcatccata taaaataaat atgataccaa aaaatttata | 780 |
| aaacttacat atcttattca actaattgag ctaaatccct tacctttgga ttaggaattt | 840 |
| caaaatttta aggaatttaa aatgcttgga atttgagttg ttttaatttt aattttcttc | 900 |
| attttcaaa tgctttgttt ggataaatca attcaaattt cttcaatttt aaattatttg | 960 |
| tttgaataag gcaattcaat tttctacatc tgtaaaattt taattttata ttttaaatag | 1020 |
| atgaaatttc aatattgaac tttatagaaa acaaacacaa tctaatttta aaatattaat | 1080 |
| taaaaattat ttttccattt ttaataattt aaaaatacaa aatattgata atttattta | 1140 |
| gggttgtttt tcctgaccac aattagtgac gttttcaac cgacatcaac caaggctatt | 1200 |
| tttcggttga tatcaaataa ggtttatttt gtcaaagtat gtcgggaata tttgtcagct | 1260 |
| gatgtcagtc aggactattt ttcggctaac gttggttgag tttattttt tgtcgatgct | 1320 |
| ggctagggtt ttttttaccaa tgtcgcatag ggtttgttg ccgacaccg actaaggctt | 1380 |
| ttttgaacga cattgactaa gactattttt ggccaacatc ggcttgggat tttttggtcg | 1440 |
| atgtcttcta gggatttttt agtcgataaa tagcccttac taaccaacat caaccttaaa | 1500 |
| aaccctagta ggcgttgaca aaaaaaaat tctatccaac attggctaaa aaatagcttg | 1560 |
| gtcaatgtca actaatagaa cctacctgac ctcggctgaa agcatcatt ggtcaacgtt | 1620 |
| ggccgaaaaa tccctagtct aagttggcta aaaaatagtc ataatcaatg tcggacaaaa | 1680 |
| aatcctagcc aacatcgact ataaaatagt cttggttaat gttgactaaa aatagctctg | 1740 |
| atcgatgtcg accgaaaaaa ctctagtgga tatcgactaa aagaacctag tcgatgttga | 1800 |
| ctaaaaatag tcatgcctga tgtcggtcaa aaataccag ctggtattag cagaaaaaac | 1860 |
| catagcgaac atcaaccaaa aaattataac taatgtggtt aagaaatagt ggctgatatt | 1920 |
| tgaaagggag gcgggaggcc cagctggacg gtataaaaag aagtggcagg attgctaatt | 1980 |
| ccttatccca atcaacacat | 2000 |

<210> SEQ ID NO 26
<211> LENGTH: 4382
<212> TYPE: DNA
<213> ORGANISM: Glycine max
<220> FEATURE:
<221> NAME/KEY: 5'UTR
<222> LOCATION: (1)..(359)
<220> FEATURE:
<221> NAME/KEY: 5'UTR
<222> LOCATION: (1388)..(1405)
<220> FEATURE:
<221> NAME/KEY: 3'UTR
<222> LOCATION: (3924)..(4382)

<400> SEQUENCE: 26

| | |
|---|---|
| aataaagaga gcattacatt acaataactc tgtctctctt ttttaaaatt agggaaacaa | 60 |

```
ggaagcaaaa tgacacaata gtccttcttc cctgtttcca ctttccaggt tttctccttc     120
tcgtttgttg agcgcttttc tctccctctc cctcttcttc actcagtcag gtacgctaac    180
aaatctgcta ttcaatcaat tcctctttct ctctgatcta cgtacgtgtc cgcaaactgc    240
acctccactc tccactcatt ccatctaatc ttcccttttc gcttcagaga tccaactcct    300
catataattc aagacaaaat cccgcgtttt ctgcatttct agacgttcta ccctacaagg    360
ttctcgattc ttcttttttc tttttttttt agactattat tattttaaaa aaataaaaat    420
aataatgaga gctggatgcg tctgttcgtt gtgaatttcg aggcaatggg gttctgattt    480
tcgttacaga ttgcattgtt tgctttcctc ctctccgttt tttctttgcc ttgttttat     540 ttttaatttt ggggatgttt tcggtcttgc ctttgtttct gcattttttt ttcggtttgc    600
gatgttttca gatctgcgct ggcttatacg acgaatttgt tcttattcgt gactttccgc    660
ttgattgacc tgttttacct ctggaatctc acacgtgatc aaataaggct gctatttag     720 ttgaagtaga atctatacac actttgtagc attcttttta cgatcactta cacgggtggt    780
ttttaatcag gcttttttg tgggggtata acattttcc tcctcgattc tttccgataa      840
aagcttaatt ggattatagg aagtgggaaa caatgcgtgg gagctctttg gtttgttttt    900
cgtaggttaa acttgcaggt ttaagttctg aatcaggagt tccaaatata gaggctgggg    960
gcataaaaaa agagaattct atggatctgt tctgaaattg gagccactgt ttcgagttgc    1020 tatttttta ctagtattaa taagaacaag tttgctttt attttacatt ttttcccgtt     1080
tcttttgcca aaagtattta tgatcactct cttctgtttg tgatattact tataagtgct    1140
gtgctgtaat tatttgttat ttggggtgaa gtataatttt tgggtgaact tggagcattt    1200
ttagttagat tgatttctcg atatcattta aggtttaggt tgacccttc cactcgtttg     1260 tggttgattg ttttttttt ttttatctct tatcatttac agtgcttctt tgcctatttt     1320
tttcattatc cccttcgtg aaggtagga gaagaaaaac aatgacttgc gtaaattttg     1380
catgcagctg ccgtagaaat tcattatggt ggcaacagct gcaacttcat cattttccc    1440 tgttacttca ccctcgccgg actctggtgg agcaggcagc aaacttggtg gtgggcctgc    1500
gaaccttgga ggtctaaaat ccaaatctgt gtcttctggt ggcttgaagg caaaggcaca    1560 agccccttg aaaattaatg gaaccacagt tgttacatct aaagaaatct tgaagcatga     1620
ggatgatcta ccttcacctc ccccaggac tttatcaac cagttacctg attggagcat      1680
gcttcttgct gccattacaa caattttctt ggcagctgaa aagcagtgga tgatgcttga    1740
ttggaagcca aggcgacctg acatgcttat tgaccccttt gggataggaa aaattgttca    1800
ggatggtctc gtgttccgtg aaaactttc tattagatca tatgagattg gtgctgatcg    1860
aaccgcatct atagaaacag taatgaacca tttgcaagta agttcgtcct catacaagtg    1920
aatctttatg agcttcagag atgagtatgt tttgactagg acagggctgt atatttagtt    1980
acactgcata attgaatttc atgtatagat aatatcatcc tgttgttact tttcatactt    2040
gatttatatc aactatttgc ttaacaacag gaaactgcac ttaatcatgt taaaagtgct    2100
gggcttcttg gtgatggctt cggttccacg ccagaaatgt gcaaaagaa cttgatatgg     2160 gtagttactc ggatgcaggt tgtggtggat cgctatccta catggttagt catctagatt    2220
cacccattac atgtcattcg caatgtgccc ttgttaagct gctatttctc tgtctatttt    2280
agtgatcttt atgaggaatg atcactccta aatatattca tggtaactat tgagacttaa    2340
ttatgagaac cacaatactt ttgaaattcg tctgggatga aaattgatta gatacacaag    2400
ctttatacgt gatgaactat gggaagcctt gtgcaacaga gctgttgatc tatacatgag    2460
```

```
atgtagtata gtattaatta catattagat atgatgactt atccttgttt aattattgta    2520
aaaagagaaa ctgatactat gtgttctttg caattgtttt cttaccagtt atataccctc    2580
tgttctgttt gagtactaga tgtataaaat atgcaattat tctggcttct tggtgttgga    2640
ttgaagttag ataagctatt agtattatta tggttattct gaatctaatt agctgaaatt    2700
gtgtgtctat gtttgcttca ggggtgacgt agttcaagta gacacctggg cttctggatc    2760
agggaagaat gctatgcgcc gtgattgggt tttacgtgac tgcaaaactg gtgaaatctt    2820
gacaagagct tccaggtaga aatcattctc tgtaattttc cttccccttt ccttctgctt    2880
caagcaaatt ttaagatgtg tatcttaatg tgcacgatgc tgattggaca caattttaaa    2940
tctttcaaac atttacaaaa gttatggaac cctttctttt ctctcttgaa gatgcaaatt    3000
tgtcacgact gaagtttgag gaaatcattt gaattttgca atgttaaaaa agataatgaa    3060
ctacatattt tgcaggcaaa aacctctaat tgaacaaact gaacattgta tcttagttta    3120
tttatcagac tttatcatgt gtactgatgc atcaccttgg agcttgtaat gaattacata    3180
ttagcatttt ctgaactgta tgttatggtt ttggtgatct acagtgtttg ggtcatgatg    3240
aataagctga cacggaggct gtctaaaatt ccagaagaag tcagacagga gataggatct    3300
tattttgtgg attctgatcc aattctagaa gaggataaca gaaaactgac taaacttgac    3360
gacaacacag cagattatat tcgtaccggt ttaagtgtat gtcaactagt ttttttgtaa    3420
ttgttgtcat taatttcttt tcttaaatta tttcagatgt tgctttctaa ttagtttaca    3480
ttatgtatct tcattcttcc agtctaggtg gagtgatcta gatatcaatc agcatgtcaa    3540
caatgtgaag tacattgact ggattctgga ggtattttc tgttcttgta ttctaatcca    3600
ctgcagtcct tgttttgttg ttaaccaaag gactgtcctt tgattgtttg cagagtgctc    3660
cacagccaat cttggagagt catgagcttt cttccgtgac tttagagtat aggagggagt    3720
gtggtaggga cagtgtgctg gattccctga ctgctgtatc tggggccgac atgggcaatc    3780
tagctcacag tggacatgtt gagtgcaagc atttgcttcg actcgaaaat ggtgctgaga    3840
ttgtgagggg caggactgag tggaggccca aacctatgaa caacattggt gttgtgaacc    3900
aggttccagc agaaagcacc taagattttg aaatggttaa cggttggagt tgcatcagtc    3960
tccttgctat gtttagactt attctggccc ctggggagag ttttgcttgt gtctgtccaa    4020
tcaatctaca tatctttata tccttctaat ttgtgttact ttggtgggta aggggaaaa    4080
gctgcagtaa acctcattct ctctttctgc tgctccatat ttcatttcat ctctgattgc    4140
gctactgcta ggctgtcttc aatatttaat tgcttgatca aaatagctag gcatgtatat    4200
tattattctt ttctcttggc tcaattaaag atgcaatttt cattgtgaac acagcataat    4260
tattattctt attattttg tatagcctgt atgcaagaat gacttgtcca tccaatacaa    4320
ccgtgattgt atgctccagc gtgtatttat gcaagcttcc cacatgggaa ttattgtgtg    4380
ca                                                                   4382
```

<210> SEQ ID NO 27
<211> LENGTH: 1251
<212> TYPE: DNA
<213> ORGANISM: Glycine max
<220> FEATURE:
<221> NAME/KEY: mutation
<222> LOCATION: (352)..(352)
<223> OTHER INFORMATION: Sequence can be mutated from C to T.
<220> FEATURE:
<221> NAME/KEY: mutation
<222> LOCATION: (380)..(380)

```
<223> OTHER INFORMATION: Sequence can be mutated from T to a deletion.
<220> FEATURE:
<221> NAME/KEY: mutation
<222> LOCATION: (383)..(383)
<223> OTHER INFORMATION: Sequence can be mutated from G to A.
<220> FEATURE:
<221> NAME/KEY: mutation
<222> LOCATION: (520)..(520)
<223> OTHER INFORMATION: Sequence can be mutated from G to A.
<220> FEATURE:
<221> NAME/KEY: mutation
<222> LOCATION: (1043)..(1043)
<223> OTHER INFORMATION: Sequence can be mutated from G to A.

<400> SEQUENCE: 27
atggtggcaa cagctgcaac ttcatcattt ttccctgtta cttcaccctc gccggactct      60
ggtggagcag gcagcaaact tggtggtggg cctgcgaacc ttggaggtct aaaatccaaa     120
tctgtgtctt ctggtggctt gaaggcaaag gcacaagccc ctttgaaaat taatggaacc     180
acagttgtta catctaaaga aatcttgaag catgaggatg atctaccttc acctcccccc     240
aggactttta tcaaccagtt acctgattgg agcatgcttc ttgctgccat acaacaatt      300 ttcttggcag ctgaaaagca gtggatgatg cttgattgga agccaaggcg acctgacatg     360
cttattgacc cctttgggat aggaaaaatt gttcaggatg gtctcgtgtt ccgtgaaaac     420
ttttctatta gatcatatga gattggtgct gatcgaaccg catctataga aacagtaatg     480
aaccatttgc aagaaactgc acttaatcat gttaaaagtg ctgggcttct tggtgatggc     540
ttcggttcca cgccagaaat gtgcaaaaag aacttgatat gggtagttac tcggatgcag     600
gttgtggtgg atcgctatcc tacatggggt gacgtagttc aagtagacac ctgggcttct     660
ggatcaggga agaatgctat gcgccgtgat tgggttttac gtgactgcaa aactggtgaa     720
atcttgacaa gagcttccag tgtttgggtc atgatgaata agctgacacg gaggctgtct     780
aaaattccag aagaagtcag acaggagata ggatcttatt ttgtggattc tgatccaatt     840
ctagaagagg ataacagaaa actgactaaa cttgacgaca cacagcaga ttatattcgt      900 accggtttaa gttctaggtg gagtgatcta gatatcaatc agcatgtcaa caatgtgaag     960
tacattgact ggattctgga gagtgctcca cagccaatct tggagagtca tgagctttct    1020
tccgtgactt tagagtatag gagggagtgt ggtagggaca gtgtgctgga ttccctgact    1080
gctgtatctg gggccgacat gggcaatcta gctcacagtg gacatgttga gtgcaagcat    1140
ttgcttcgac tcgaaaatgg tgctgagatt gtgaggggca ggactgagtg gaggcccaaa    1200
cctatgaaca acattggtgt tgtgaaccag gttccagcag aaagcaccta a              1251

<210> SEQ ID NO 28
<211> LENGTH: 416
<212> TYPE: PRT
<213> ORGANISM: Glycine max
<220> FEATURE:
<221> NAME/KEY: MUTAGEN
<222> LOCATION: (118)..(118)
<223> OTHER INFORMATION: Sequence can be mutated from Pro to Ser.
<220> FEATURE:
<221> NAME/KEY: MUTAGEN
<222> LOCATION: (127)..(416)
<223> OTHER INFORMATION: Sequence can be mutated from a T380* frameshift
      mutation in the coding sequence.
<220> FEATURE:
<221> NAME/KEY: MUTAGEN
<222> LOCATION: (128)..(128)
<223> OTHER INFORMATION: Sequence can be mutated from Gly to Glu.
<220> FEATURE:
<221> NAME/KEY: MUTAGEN
<222> LOCATION: (174)..(174)
```

<223> OTHER INFORMATION: Sequence can be mutated from Ala to Thr.
<220> FEATURE:
<221> NAME/KEY: MUTAGEN
<222> LOCATION: (348)..(348)
<223> OTHER INFORMATION: Sequence can be mutated from Arg to Lys.

<400> SEQUENCE: 28

```
Met Val Ala Thr Ala Thr Ser Ser Phe Phe Pro Val Thr Ser Pro
1               5                   10                  15

Ser Pro Asp Ser Gly Gly Ala Gly Ser Lys Leu Gly Gly Pro Ala
            20                  25                  30

Asn Leu Gly Gly Leu Lys Ser Lys Ser Val Ser Ser Gly Gly Leu Lys
        35                  40                  45

Ala Lys Ala Gln Ala Pro Leu Lys Ile Asn Gly Thr Thr Val Val Thr
    50                  55                  60

Ser Lys Glu Ile Leu Lys His Glu Asp Asp Leu Pro Ser Pro Pro Pro
65                  70                  75                  80

Arg Thr Phe Ile Asn Gln Leu Pro Asp Trp Ser Met Leu Leu Ala Ala
                85                  90                  95

Ile Thr Thr Ile Phe Leu Ala Ala Glu Lys Gln Trp Met Met Leu Asp
            100                 105                 110

Trp Lys Pro Arg Arg Pro Asp Met Leu Ile Asp Pro Phe Gly Ile Gly
        115                 120                 125

Lys Ile Val Gln Asp Gly Leu Val Phe Arg Glu Asn Phe Ser Ile Arg
130                 135                 140

Ser Tyr Glu Ile Gly Ala Asp Arg Thr Ala Ser Ile Glu Thr Val Met
145                 150                 155                 160

Asn His Leu Gln Glu Thr Ala Leu Asn His Val Lys Ser Ala Gly Leu
                165                 170                 175

Leu Gly Asp Gly Phe Gly Ser Thr Pro Glu Met Cys Lys Lys Asn Leu
            180                 185                 190

Ile Trp Val Val Thr Arg Met Gln Val Val Asp Arg Tyr Pro Thr
        195                 200                 205

Trp Gly Asp Val Val Gln Val Asp Thr Trp Ala Ser Gly Ser Gly Lys
210                 215                 220

Asn Ala Met Arg Arg Asp Trp Val Leu Arg Asp Cys Lys Thr Gly Glu
225                 230                 235                 240

Ile Leu Thr Arg Ala Ser Ser Val Trp Val Met Met Asn Lys Leu Thr
                245                 250                 255

Arg Arg Leu Ser Lys Ile Pro Glu Glu Val Arg Gln Glu Ile Gly Ser
            260                 265                 270

Tyr Phe Val Asp Ser Asp Pro Ile Leu Glu Glu Asp Asn Arg Lys Leu
        275                 280                 285

Thr Lys Leu Asp Asp Asn Thr Ala Asp Tyr Ile Arg Thr Gly Leu Ser
    290                 295                 300

Ser Arg Trp Ser Asp Leu Asp Ile Asn Gln His Val Asn Asn Val Lys
305                 310                 315                 320

Tyr Ile Asp Trp Ile Leu Glu Ser Ala Pro Gln Pro Ile Leu Glu Ser
                325                 330                 335

His Glu Leu Ser Ser Val Thr Leu Glu Tyr Arg Arg Glu Cys Gly Arg
            340                 345                 350

Asp Ser Val Leu Asp Ser Leu Thr Ala Val Ser Gly Ala Asp Met Gly
        355                 360                 365

Asn Leu Ala His Ser Gly His Val Glu Cys Lys His Leu Leu Arg Leu
    370                 375                 380
```

Glu Asn Gly Ala Glu Ile Val Arg Gly Arg Thr Glu Trp Arg Pro Lys
385                 390                 395                 400

Pro Met Asn Asn Ile Gly Val Val Asn Gln Val Pro Ala Glu Ser Thr
                405                 410                 415

<210> SEQ ID NO 29
<211> LENGTH: 2000
<212> TYPE: DNA
<213> ORGANISM: Glycine max

<400> SEQUENCE: 29

| | | | | | |
|---|---|---|---|---|---|
| tatatggttt | attcataaag | ttgagagcta | gcatttagag | acttgatata | ttgtggtaca | 60 |
| tgaacgataa | tacttgctat | tagtggacct | atcgccatga | ctcatatttt | gtttcttgtt | 120 |
| atgactaatg | ttaggttaaa | tggaccaagt | cggagaatga | tggaattttc | gttcctttat | 180 |
| tcccatattg | tttttctgtt | ttttcccgtt | gcgatttcta | tgggaagcgg | ttttttgtac | 240 |
| atagtccatt | ttcttcccac | attcaatcct | tatcctcttc | aatgttcaac | aacaaacaac | 300 |
| aacccatgct | ccaatccatg | aaggttgagc | tttgtgatgg | gcagagctct | ataaatagaa | 360 |
| ccaggtgctc | tcagttttga | tcatcaagtc | tactcctctc | ttcagataaa | ctcaccattg | 420 |
| agtttgagcc | agtaaaggtt | tggaaagcta | aaactgtgaa | ggctgaaaaa | ggtcaatagc | 480 |
| aatggctaga | ggtagtacct | ttaaaattta | ttttcttct | ctgctttcga | tgtttgctct | 540 |
| ggatgtgttg | cttatggttg | ttaacatgtt | caaactagta | tatttacgtt | taatatctaa | 600 |
| gggatttaga | gtgtgagaag | gcctcattgg | cgcgacccaa | tgggagagg | cttagacca | 660 |
| tggaagtgat | ggaagggtgt | gcaatatggt | gtggtgagag | gataggagga | gtttgtggag | 720 |
| gtggtggagt | tcgtggtgca | tgttggcgct | ggtgagggtg | caagttatga | tagcgactag | 780 |
| gtattgagta | taagtgtggt | tgtggaaaag | gaaggggaag | agatatcatg | tttgactaga | 840 |
| tgtcatgcta | gctttggatc | tagtggtgtt | tagttatatg | ggggtgttgc | gtggccgtgg | 900 |
| ggttgaagat | gaattgcagc | actagaagtt | atggtggacg | tggttcgaag | aagaaaataa | 960 |
| ataggaccaa | aataaaaata | gttacaattt | ttagtcgcca | ctattttaaa | ttatttattt | 1020 |
| taaaatttaa | aagttaatga | acattaatg | tttctaacaa | aaactgggaa | aaaaatcaaa | 1080 |
| acgaaacctt | tcaaaaacat | aaaaaaataa | atgaaacttt | taaaacttaa | tatacaaaaa | 1140 |
| taaaaaatac | taaaatataa | aaggataaaa | ataatatttt | ggcttatctt | atatataaga | 1200 |
| tacaatatat | gacaagaggt | aatataaaat | atggtaaaat | atgtttggag | ttcttgtaaa | 1260 |
| atttaaaaag | tattattta | gtcctcataa | aattttcat | attaatttga | tcctttaaaa | 1320 |
| ataaaacata | ttttttatgg | tctttaatgg | taacttcgtt | agacaattcc | tttatatgac | 1380 |
| taacagactt | aattattttc | tttcttttc | ttcccaagca | cactcaaaag | acactaaaac | 1440 |
| atattgttac | tttatctttc | cctctaatgt | catacaaaaa | aatcatcaaa | aaataacaaa | 1500 |
| aattacaatt | tttaagattt | ttaatcgcaa | aaaattgtgt | aatgcatttt | agagaatttt | 1560 |
| aattaccaca | aatgatttaa | tttatgtgta | attaaattca | tattagatta | tcatataaca | 1620 |
| aagttatcat | ttagaactat | aaaatttatg | ttttattttt | cacatgacca | aaataatatg | 1680 |
| aattttttta | ctataatcaa | aataatactt | tgcaaattta | cgacgattca | aaatatattt | 1740 |
| tatcttataa | agtatgaaaa | aattattttt | catttagttg | tatttcaaac | ccaaactatt | 1800 |
| aattattcca | tttactcgt | gtgcattgcc | ccacacggct | cacacaaccg | agccacgggg | 1860 |
| ctccaacatg | taatttctag | aaaaccatag | gagataaaaa | aagagtagca | aagattggag | 1920 |

-continued

| aagttagtaa aacaaaaagg gtagtatggt aaatacaaac atagaagagt ataggaatta | 1980 |
| gaattataaa ctttgaaaga | 2000 |

<210> SEQ ID NO 30
<211> LENGTH: 7394
<212> TYPE: DNA
<213> ORGANISM: Glycine max
<220> FEATURE:
<221> NAME/KEY: 5'UTR
<222> LOCATION: (1)..(337)
<220> FEATURE:
<221> NAME/KEY: 5'UTR
<222> LOCATION: (944)..(968)
<220> FEATURE:
<221> NAME/KEY: 3'UTR
<222> LOCATION: (4500)..(7394)

<400> SEQUENCE: 30

| gaggcgggcg ggaggacagg tgtattgcat ataacaaagc cccaggaggc tatttcggtg | 60 |
| ccatcaaaat aatcgctggc cctatcacat tattgttaat attcttccct tctttacctt | 120 |
| ctactttccg aatccagaaa acaccacaac accacccaga attgttgggt tccattctca | 180 |
| aaacagagaa caagaagaag aagaaagaga gagagtgaaa acgggaaaag caaaaagttg | 240 |
| tttctgtgat tgattctctg caaccgaatc atcatcagcc acttcttccc gtttcatctc | 300 |
| tcccatttct tcttttcttc cgctctggtt cagtaaggta cgaaacgccg cgttttgctc | 360 |
| ccttctgatc tagctccatc ccaaaatcac gtatccaaac ttcttttttca ttttcattat | 420 |
| tattattatt tctttaaaaa aattggtttt actaggatcc ctaacttact gcattcaccg | 480 |
| gaaacccaac aaggcgttga ggattactat ctcaatcgct ttcggtttat ttttcgtgaa | 540 |
| tttcgatgct ttggattgcg actcatattg ttgttacaaa caatattatt tatttttaaa | 600 |
| ataatacttg ttttttttta taaaaaaaat gttcttgctc ggacttcaat tcgccatctt | 660 |
| tcattataca atcttggttt gcggtgtttt ctagattcaa tgtcagatct acaccgactt | 720 |
| ttgcattaat tgcacattaa ttcgccgata gattggtgtc tgaaaaaact atcattactt | 780 |
| actatattta caccttttc attaattcgg taacataatt ttctaattga tgttgatgtt | 840 |
| gatgttttt cttttcttt aataacattg cagcttggct ttaaaattta tatattacta | 900 |
| atatttagt tttatttaaa tggtgtttta actttccatg caggcgaaga gggttaacgt | 960 |
| tattcataat ggttgcaaca gccgctacgg cgtcgtttct tcccgtgcct ttgccagacg | 1020 |
| ctggaaaagg gaaacccaag aaactgggtg gtggtggcgg tggcggtggc ggttctgtga | 1080 |
| acctcggagg actcaaacag aaacaaggtt tgtgcggtgg cttgcaggtc aaggcaaacg | 1140 |
| cacaagcccc tccgaagacc gtggagaagg ttgagaatga tttgtcgtcg tcgtcctcgt | 1200 |
| cgatttcgca cgccccgagg actttcatca accagttacc tgactggagc atgcttctgg | 1260 |
| ccgccatcac caccgtgttc ctggcggcgg agaagcagtg gatgatgctg gattggaagc | 1320 |
| cgcggcgccc cgacatgctc attgaccect tgggattgg gaagatcgtg caggatgggc | 1380 |
| tgtgttcag gcagaacttc cccattaggt cctatgagat tggcgccgat aaaaccgcgt | 1440 |
| ctatcgagac tttaatgaat catttgcagg tcagcttttg caaaaaattg ctgagaattg | 1500 |
| cattcagcaa tcacgataaa tataacttt aataaattat tatagaagtt aagtaactta | 1560 |
| tcacgggttg tcaacaaaaa tttagagaat aattgcatag acaaaacttt acctacagtt | 1620 |
| cgtttgacat ttttttgtgtc gttttaaat caaaattaaa attttatctt ggtaatttgc | 1680 |
| agattattag atacaactcc aatttcgatc aaagaacaat gccaaaaaca cctatggaat | 1740 |

```
ctaagttttg tgcaattgct tattgatgat tttattttat tgcctaaatt gtctgttttc    1800
caaacaggag actgcactta atcatgttaa gactgctggg cttcttggtg atggatttgg    1860
ttccacgcct gaaatgtgca aaaagaacct gatatgggtg gtgactaaga tgcaggttgt    1920
ggttgataaa tatcccacat ggtaagttgg tgtgactaag aagaaccttt ttgatgtgtg    1980
aagaattgca aaggcgtcca tgctcagctg tgaaatcttc ttttgcctta ctcatcttta    2040
ctttgacttt atatagtatc tggttgaatt attttgtact tctgcatttg tttctgtcac    2100
ttgtgctttt ttgtttcaca aaattggtat gatagttagg aacttgggat taaaggcatg    2160
tttggaatat attgtgattg tgaattattt ttaaaaatat tttcactttt caaaatctat    2220
ctcatgaatc tgtaaaaata aaaataaaaa ataaaactac tgtaatgtgt ataaaaaatt    2280
cttcttggat ggtaattgat ctgataagca catgctttt acataatgaa ttatatgaag     2340
tcctttgcct taagtctgtt agactgggta tgagatatgg tagtaaattc ttttacatt     2400 ccgtacattt ttttgcatat ttctgtctta ttattgtaaa atgttggatg catatacagg    2460
ttttcaaaag aagcaactta taccatgtgc ccttttctgc attttggtct gttcgagaat    2520
aatctcttta gtaaattctg aatctgttca tctgaagttg agtgaatcta tatttgcttc    2580
aggggtgatg ttgttcaagt agacacttgg gtatctgcat cagggaagaa tggtatgtgt    2640
cgtgattggc ttgtgcgtga cgcgaaatct ggtgaaatct tgacaagagc ctccaggtag    2700
atattagttt caggaatcct ttcttctgtt gcctatagac atgttttgaa gtgttattct    2760
gaatctgaat gtgtctctct ggtgatttgg cactgctttt aatctcacaa ggctgtgtga    2820
agtcatctgt tatcatattt acttttttctt aatacaccac tattgaaagg caattaatta   2880
ctgatttaat tatactaaat tttgtagatg agaatttctg aatctaccaa cagtatctca    2940
tatcttcttg atttgttatt aagtacaagc cttcaactgg tgtacatgtt gtacctaggt    3000
gcgaggaact tataagcatt ttctgattgg ttgatttga ttttgatttt gattttgatg     3060
ttatgcagtg tttgggtcat gatgaataaa gtgacaagaa gactgtctaa aattcccgaa    3120
gaagtcaggg cagagataag ctcttatttt gtggactctg ctccagttgt gccagaggat    3180
aacagaaaac taaccaaact tgatgattcc gctaatttca ttcgcactgg tttaagtgta    3240
tgcaaacttc atgttatcat tgatttattt tctaaaatat ctcagatgtt ttctaatcat    3300
attatgtgtc tctattttca gcccagatgg aatgatctag atgtgaatca gcatgttaac    3360
aatgtgaagt atgttgggtg gattctggag gtagtcttct gttcttgtat tattattatt    3420
ctgtccttaa tttcttttct tcttttggtg gatatattag taaggcttgt ctgactggac    3480
agtttgaact tttgcaaggg aggttgaatg gtgatactgt tattctggaa cacccacttt    3540
cctttcaaaa gactctaaac cccattgggt ctatatgata gtgtgccata gcaaatgcca    3600
ctctgccagt gtgttctttt gagaggaatc tgggtgtgag taataatgaa agtgttgagt    3660
aagatcatgt ttcagaattc cagtctcatc aagtgaaagt tgtttcaaga cagaagcatt    3720
caattttata ttatatgtgg gcatttgatg cctcatatga agtggttta tgccagtttt     3780 gaagtggctt gaaagttgat acatgggata atggatacta aaatgggatg gtggatggga    3840
aaatagagca cgcttcctcg tttgatcttt ttgtgtcct aatatttccc ccttttttgat    3900 tattgtgtta ttttgaggga aaacaattga ttttacaagg agctctcttt ctaacatttt    3960
atattggttg aaatttatta gaaatcacta gttttggtga gacccaatca attaatgatt    4020
atttcaagat ttagaagtgt gatctacaaa aaatgatgat ttctaataaa tttaaatcaa    4080
tcatagaggg tttgaaagag ggtgacatgg aaagtgtcac tagcattcca ttttatgttt    4140
```

```
tatttgttta gtttgttatt tgcttggatt ttgattagaa tgctttacca aaagaattit    4200 gctttggaca actgcagagt gctccacagc cacttttgga gagccatgag ctgtgtgcca    4260
tgacattgga gtacaggagg gagtgtggca ggaacagtgt gctggattcc ctctctgatc    4320
tctctggtgc tgatgtagga aacttggcag atggtggatt ttttgagtgc aagcacttgc    4380
ttcgacttga tgatggtgct gagattgtga ggggtaggac tcaatggagg cccaaacctt    4440
taagcagcaa ctttggtcat gttttgagtc aggttccagt tccagcagaa agcacctgaa    4500
tcttatctta ttgattggca tcactggagg aggagtggca taaattcata gagagctttg    4560
cttgttttta tcaaatctac gtatcttaaa atatatataa aagaaagtgt gttactttgg    4620 ctaaaaagg ggagggaag tagaaagtaa aaaaaaaaa aaaatctcg ctctcatgat    4680 tttgtaatta aaaaatagct cctagcacta ctttctccta cctgctccat tttctgtttc    4740
acttatggtt atgcagctgc ttggtgtcat caatatttaa ttgtttcatc aaaatggcta    4800
agggtgtata ttatatattt ttgttttctt ttaccttata agaaatatgc aatattcctc    4860
gtgagcatac caaaacaaat aaatgtatgt ataggttgca ggaaaggcaa gacacttcgg    4920 tctctttat tgcttctatt ttagtcttca attttttta ggcaggtctt gatattgtta    4980
tagttgttat atgttctatg catctgttgt ccacgaagca caaaaaaga tcagatgaag    5040 tggatatgca atcaaaaggc gagctgggtt gcttccacca gaaggcaccg ccttctgttg    5100
gaagaccttg gaaggcccaa gtgggcctga ttgctagttg tacccctatg tttactaaat    5160
actccccctg ccttttttg ctgattcttt ttccgtaacg ttacgaaact ttacgaatta    5220
cgtaacgata cttgttttct ttctgtaatg tcacaaaacc ttacggatta tgtaatcatc    5280
ctttttttgg cttccgaaat gttacggaac ttcacggatt gtgcaacaat gcttcctttt    5340
gatttccagc atgtcatgga acttcacgga ttgtgcaaca atgcttcctt ttgacttcca    5400
gcatgtcacg aaacttcaca gattgcctaa cgatgggtgc caagtacctc gaagtggtca    5460
aacgagggtc gcatcccaac aaacggatgg tccccggacg aaattagggt atgacacctg    5520
tgatgttcca cctatgtatt cagggatagc tggtggtttt cggcgaaggt gatttcaaac    5580
ggagttaatc ccgtactcga atggcacgaa gtattatacg accattctgc ccacaacaga    5640
aatcgtcccc acaacgctgg cttgcgatgg acgaaggccc tcaagtattg ttctactatc    5700
cgatttgcca cctccgtctg accgtctgtt tgtggatggt aagacgagct gagtctaagc    5760
ttggtgccac tcaactcaaa taattccttc caaatctac tcacgaacaa tggatcccta    5820
tccgagatga tgctgcgagg tagcccatgc agacgactca ccatggccgt gaacaactcc    5880
gccaccttcc tcgcagaatg tttagtgggt aacataccca gatgtaatcc ctttgagaat    5940
cgatccacaa cctaaaaat tcatgtgtgg cccttataag ctggcaaccc cacgatgaag    6000
tctatactta aatcctccca cggccggaat ggtaccggta agggacataa taatccagct    6060
ggcttgcggt tgtcatactt cgtaagttga caagtcacac atgctgggat gaacgtacga    6120
acatcactcc tcatggagtt ccatgtgaaa ttctcctgca acctttggag tgttttctga    6180
attccataat ggcccctgc tggtgtactg tgaaattcct ccatcaataa cagaataatg    6240
gaagaccccg ttgggagcca aatgctgtgc ttgtgcagga tcagtcatt ctcaagttta    6300 tattcagtag ctatggtagg gtccccttga atttttctcct tcaatgtcag gaattcaggg    6360
tgtgttgcta attctctttt gagatcagca atgaaggaga actgtggtgt cgacaacaga    6420
tataaggagg ccttgtcttc ttctccggcg actctggaca acgcgtttgc cacaccattc    6480
```

```
tcgtgacctg gctgatattg gatggtatat tcgaatccca acaagcgaat taggtaacga    6540
tgttcctcca gcgtctgcac cgcctgagtc atcaggtccc gtaagctttg gtgattagtg    6600
agaatcacaa aatgatggcc caacaagtaa tggcgccact tttaacgac cgtagttatt     6660 gccgcaagtt cgtgaatata agttgaggaa gcacagagct tgggacaaaa ctccttactg    6720
aaaaactcga tggggtgacc cgcctgagaa agaacagccc ctattctggt accagaagag    6780
tccatctcca ccacaaatgg aatctcgaag ttgggaagtg cgagaactgg cgcggtggat    6840
attgctttct tcaatgcgtt aaaagcttca gtcgccatct ccgaccactg aaactgacct    6900
ttgcacaata actgagaaag aggcgttgca atttggcat agcccttaat aaacctcctg     6960
taaaaaccca ccaagcccaa aaaacttcat aatgctttaa ctgttcgagg aagtggccac    7020
tcctggatcg catgcaactt atccggcacc ggttccacac ccctcccgga gaccacatgt    7080
cccaaatatt cgagctgttc ctaagcaaat gtacatttag aacgcttcaa ggaaaatttc    7140
cttgagacca agagttggaa cgcgttctcc agatgcacca gatgatcgt catcgtcttg      7200 ctatagatga gcacatcatc gaagaagacg atgatggact tttgcaagat gggttagaac    7260
aactgattca tggttgcctg gaatgtagat ggagcgttac acagaccaaa aggcatcact    7320
ctaaactcgt aatgcccttg atgcgttcag aatgcggttt tgttgatgtc tccctccttc    7380
atcagaatct gatg                                                      7394
```

<210> SEQ ID NO 31
<211> LENGTH: 1269
<212> TYPE: DNA
<213> ORGANISM: Glycine max
<220> FEATURE:
<221> NAME/KEY: mutation
<222> LOCATION: (47)..(47)
<223> OTHER INFORMATION: Sequence can be mutated from C to T.
<220> FEATURE:
<221> NAME/KEY: mutation
<222> LOCATION: (1117)..(1117)
<223> OTHER INFORMATION: Sequence can be mutated from G to A.
<220> FEATURE:
<221> NAME/KEY: mutation
<222> LOCATION: (1154)..(1154)
<223> OTHER INFORMATION: Sequence can be mutated from G to A.
<220> FEATURE:
<221> NAME/KEY: mutation
<222> LOCATION: (1184)..(1184)
<223> OTHER INFORMATION: Sequence can be mutated from G to A.

<400> SEQUENCE: 31

```
atggttgcaa cagccgctac ggcgtcgttt cttcccgtgc ctttgccaga cgctggaaaa      60
gggaaaccca agaaactggg tggtggtggc ggtggcggtg gcggttctgt gaacctcgga     120
ggactcaaac agaaacaagg tttgtgcggt ggcttgcagg tcaaggcaaa cgcacaagcc     180
cctccgaaga ccgtggagaa ggttgagaat gatttgtcgt cgtcgtcctc gtcgatttcg     240
cacgccccga ggactttcat caaccagtta cctgactgga gcatgcttct ggccgccatc     300
accaccgtgt tcctggcggc ggagaagcag tggatgatgc tggattggaa gccgcggcgc     360
cccgacatgc tcattgaccc ctttgggatt gggaagatcg tgcaggatgg gcttgtgttc     420
aggcagaact tcccccattag gtcctatgag attggcgccg ataaaaccgc gtctatcgag     480
actttaatga atcatttgca ggagactgca cttaatcatg ttaagactgc tgggcttctt     540
ggtgatggat ttggttccac gcctgaaatg tgcaaaaaga acctgatatg ggtggtgact     600
aagatgcagg ttgtggttga taaatatccc acatgggggtg atgttgttca agtagacact     660
tgggtatctg catcagggaa gaatggtatg tgtcgtgatt ggcttgtgcg tgacgcgaaa     720
```

```
tctggtgaaa tcttgacaag agcctccagt gtttgggtca tgatgaataa agtgacaaga      780
agactgtcta aaattcccga agaagtcagg gcagagataa gctcttattt tgtggactct      840
gctccagttg tgccagagga taacagaaaa ctaaccaaac ttgatgattc cgctaatttc      900
attcgcactg gtttaagtcc cagatggaat gatctagatg tgaatcagca tgttaacaat      960
gtgaagtatg ttgggtggat tctggagagt gctccacagc cacttttgga gagccatgag     1020
ctgtgtgcca tgacattgga gtacaggagg gagtgtggca ggaacagtgt gctggattcc     1080
ctctctgatc tctctggtgc tgatgtagga aacttggcag atggtggatt ttttgagtgc     1140
aagcacttgc ttcgacttga tgatggtgct gagattgtga ggggtaggac tcaatggagg     1200
cccaaacctt taagcagcaa ctttggtcat gttttgagtc aggttccagt tccagcagaa     1260
agcacctga                                                             1269
```

<210> SEQ ID NO 32
<211> LENGTH: 422
<212> TYPE: PRT
<213> ORGANISM: Glycine max
<220> FEATURE:
<221> NAME/KEY: MUTAGEN
<222> LOCATION: (16)..(16)
<223> OTHER INFORMATION: Sequence can be mutated from Pro to Leu.
<220> FEATURE:
<221> NAME/KEY: MUTAGEN
<222> LOCATION: (373)..(373)
<223> OTHER INFORMATION: Sequence can be mutated from Ala to Thr.
<220> FEATURE:
<221> NAME/KEY: MUTAGEN
<222> LOCATION: (385)..(385)
<223> OTHER INFORMATION: Sequence can be mutated from Arg to Gln.
<220> FEATURE:
<221> NAME/KEY: MUTAGEN
<222> LOCATION: (395)..(395)
<223> OTHER INFORMATION: Sequence can be mutated from Gly to Asp.

<400> SEQUENCE: 32

```
Met Val Ala Thr Ala Ala Thr Ala Ser Phe Leu Pro Val Pro Leu Pro
 1               5                  10                  15

Asp Ala Gly Lys Gly Lys Pro Lys Lys Leu Gly Gly Gly Gly Gly Gly
            20                  25                  30

Gly Gly Gly Ser Val Asn Leu Gly Gly Leu Lys Gln Lys Gln Gly Leu
        35                  40                  45

Cys Gly Gly Leu Gln Val Lys Ala Asn Ala Gln Ala Pro Pro Lys Thr
    50                  55                  60

Val Glu Lys Val Glu Asn Asp Leu Ser Ser Ser Ser Ser Ser Ile Ser
65                  70                  75                  80

His Ala Pro Arg Thr Phe Ile Asn Gln Leu Pro Asp Trp Ser Met Leu
                85                  90                  95

Leu Ala Ala Ile Thr Thr Val Phe Leu Ala Ala Glu Lys Gln Trp Met
            100                 105                 110

Met Leu Asp Trp Lys Pro Arg Arg Pro Asp Met Leu Ile Asp Pro Phe
        115                 120                 125

Gly Ile Gly Lys Ile Val Gln Asp Gly Leu Val Phe Arg Gln Asn Phe
    130                 135                 140

Pro Ile Arg Ser Tyr Glu Ile Gly Ala Asp Lys Thr Ala Ser Ile Glu
145                 150                 155                 160

Thr Leu Met Asn His Leu Gln Glu Thr Ala Leu Asn His Val Lys Thr
                165                 170                 175

Ala Gly Leu Leu Gly Asp Gly Phe Gly Ser Thr Pro Glu Met Cys Lys
```

```
                180             185             190
Lys Asn Leu Ile Trp Val Val Thr Lys Met Gln Val Val Asp Lys
        195                 200                 205

Tyr Pro Thr Trp Gly Asp Val Gln Val Asp Thr Trp Val Ser Ala
        210                 215                 220

Ser Gly Lys Asn Gly Met Cys Arg Asp Trp Leu Val Arg Asp Ala Lys
225                 230                 235                 240

Ser Gly Glu Ile Leu Thr Arg Ala Ser Ser Val Trp Val Met Met Asn
                245                 250                 255

Lys Val Thr Arg Arg Leu Ser Lys Ile Pro Glu Glu Val Arg Ala Glu
        260                 265                 270

Ile Ser Ser Tyr Phe Val Asp Ser Ala Pro Val Val Pro Glu Asp Asn
            275                 280                 285

Arg Lys Leu Thr Lys Leu Asp Asp Ser Ala Asn Phe Ile Arg Thr Gly
        290                 295                 300

Leu Ser Pro Arg Trp Asn Asp Leu Asp Val Asn Gln His Val Asn Asn
305                 310                 315                 320

Val Lys Tyr Val Gly Trp Ile Leu Glu Ser Ala Pro Gln Pro Leu Leu
                325                 330                 335

Glu Ser His Glu Leu Cys Ala Met Thr Leu Glu Tyr Arg Arg Glu Cys
            340                 345                 350

Gly Arg Asn Ser Val Leu Asp Ser Leu Ser Asp Leu Ser Gly Ala Asp
        355                 360                 365

Val Gly Asn Leu Ala Asp Gly Gly Phe Phe Glu Cys Lys His Leu Leu
        370                 375                 380

Arg Leu Asp Asp Gly Ala Glu Ile Val Arg Gly Arg Thr Gln Trp Arg
385                 390                 395                 400

Pro Lys Pro Leu Ser Ser Asn Phe Gly His Val Leu Ser Gln Val Pro
                405                 410                 415

Val Pro Ala Glu Ser Thr
            420

<210> SEQ ID NO 33
<211> LENGTH: 2000
<212> TYPE: DNA
<213> ORGANISM: Glycine max

<400> SEQUENCE: 33
ttggtaaaag ggaaatggtg taacatttaa ggggtttgtt gtgggattaa aaagcaaagg      60
ggtatcaagc gtaatatgaa aaaacttggg gtatgaataa taattactct atcttgtaat     120
taaagttatt tcaaaaacat tcacaatata ttggaagagc attaagaaga ctcaatcaaa     180
cttgaagaac aacaacttta agaggtaagt accatgaatt ttgacttatt attttaatat     240
cacaatttgt gtaactatga tcctatttag ttaagaaaac tattgaatca tgatttatga     300
taaatttaac atttaatgta attgtatatc cttaattcaa atttgatatt aatgattaag     360
ttaaaataat catgtgtcag ttaattcaca tgtttaagga tacctataat tgaaacaaaa     420
ctatcattta aaaaacttaa acattaaaaa tgataaatta ttatctttag tcctatatat     480
aagaaacaaa tgcataaatc atcaagacca ataacagtat ttaagttgat taattttaat     540
taataatgtc atcaatttaa atttattcc aaaaagacct ataaatttaa atgatttaag     600
tgtcaattgt attaaatgac gctcctcata attcaagaca taattttcca accaataaga     660
caatgagttt gacttatatt gctaattgcc caatatttgc atccactttc atagaaaatg     720
```

```
agtgaatatc tcattcatag acttcacaat aaattgaagg tataaaaaaa ttaacaatta      780
atgtatttta aaaatgctct cattttttat gtgtaagaat caaacttgag tatcagaaag      840
tttaaaaagg cacaatcttt gttgatactc gtaacagtgc aaggcttatc aggcaaaaaa      900
tagaaatcaa ctcagcctat tcgctcatcc tctcaacaag cttctcagcc tcatcattca      960
tctcctctct acaaaaccta gaaacaagag agtattgtac acaaccatgt tagcaatacc     1020
acaaaaattg ttattttat tgttattgtt aattagctcc aaggcttatt tggtgaggcc      1080
gacgcaaaac aaccagcgaa cgagaatacc aagagtgaac ttgttggggt ggcatccttt     1140
ttggtgcatt ttatcaaaca attcaagtgt gtggttgaag cgtgagatt tgcaaaggga      1200 attgatgagg aggttgaaag tgtaggttcg aggcggtggt gttggagggt ggaacggatg     1260
tggagattgt agagggaaag ggtgagaggg agtgaagcga attgggatat aagggatttt     1320
aagtgtgaga gggccttgtc gatgtgaccc tgttgggaga ggacttaaac atgaaagtga     1380
tggagttcat ggtgcatgtt ggcgctggca agcatgcagg ttgtgatggt gactaggtgt     1440
tgagtgtgag tggtggtgga agaggaagga gaagggaag agaggacatc cttaactaga      1500
tgtcgtatta gtttggatct agtggtgttt gatcgtatga aggtgttgca ttgactgcga     1560
gattgaagac gaattacagt gtcgaaagtt atgatgatta taatagatgt ggttggaaga    1620
agaaaataaa gatggccaaa ataatattt aggttttctt aattataaaa taaacaaga      1680 agtaatataa aacattataa aagaatattt ttcattaagt gttaatccaa acccaaacta    1740
ttccatttta ctcatgtgca ttgcccaacg gcccacacaa cggagccacg aggctccaac   1800
atgtaatctc ctctagaaaa acccaactat taattatgca taccacagga ggaaaaatac   1860
aataaagatg gtcaaaataa gggtagtgtt gtaaatataa aatagaagag tatagaaaat   1920
tggaattaga aactttaaaa gagaagagag gcgggcgcga ggacaggtgt attgtatata    1980
acaaacctct tggaggctat                                                2000

<210> SEQ ID NO 34
<211> LENGTH: 4959
<212> TYPE: DNA
<213> ORGANISM: Glycine max
<220> FEATURE:
<221> NAME/KEY: 5'UTR
<222> LOCATION: (1)..(312)
<220> FEATURE:
<221> NAME/KEY: 5'UTR
<222> LOCATION: (923)..(950)
<220> FEATURE:
<221> NAME/KEY: 3'UTR
<222> LOCATION: (4451)..(4959)

<400> SEQUENCE: 34
ttcggtgcca ctcaaaacaa tcgctggccc tatctctcac acacccaaac ccaacattat      60
taatactctt ccttctcttt acctttact tttcgaagca aaaacaccat aacaaaacac      120
ccagaatttg tgggttccat tcccaaaaca agaacaaga aggagagaga gagagagaga      180
atgcaacggg agaaacaaaa aacagaagta tttctgtgat tgattctctg caaccgaatc      240
atcatcagcc acttcttctc cccgtttcag ctctcccctc tctcttcttt tcctcggctc      300
tggttcggta aggtacgaaa cgccgcgttt tgctaccttc tgatctacct ccaccgcaaa      360
atcacgtttc caaacttttt ttttcctttt ttttatcatt atattctctt ataaaaaaaa      420
ttggttttac aaatcctgca ttccccggta acccaacccct cattgaggat tgctatctca    480
aatcgctttc ggttaatttt ttcgtgaatt ttgatgcatt ggactgcgac tcatgatgtt     540
```

```
gtcacaatat ttatataatt tttttaaaaa attaaatttt taaataaaaa tttctttgct    600
cggacttcaa ttcgtcctct ttcaatatac aatcttggtt tgcggtgttt tctagattca    660
atgtcagatc tacaccgact tttacattaa ttgcacaata attcgccgat agattgatgt    720
ctaaaaaaaa caatcataac ttactatata cagttataca ccttttttcat taattctgta    780 acataatttt ccaactgatg ttgatgctga tgtgttttttt tttcttttct tttctttaaa    840
taaccttgca gcttcgcttt aaaaaattta tatattaatt aatttttttta ttaaaaaaat    900 ggcgttttaa cttccatgc aggcgtaggg ggttgttatt attcttcata atggttgcaa    960
cagctgctac ggcgtcgttt ctccctgtgc cttcgccgga cgctggaaaa gggaaaccca   1020
agggtggtgg tggcggcggc gtttctgtga acctcggagg actcaaagag aagcaaggtt   1080
tgtgcggttg cttgcaggtc aaggcaaacg cacaagcccc tccgaagacc atggagaagg   1140
ttgagaatga tttgccatgg ttgccgtcgt cgtcgatttc gcacgccccg aggacttttta   1200 taaatcagtt acctgactgg agcatgcttc tggccgccat caccaccgtg ttcctcgcgg   1260
cggagaagca gtggatgatg ctggattgga agccgcgccg ccccgacatg ctcattgacc   1320
cctttgggat tgggaagatc gtgcaggacg ggctcgtgtt caggcagaac ttccccataa   1380
ggtcttacga aattggcgca gacaaaactg cgtcaataga gaccttaatg aatcatttgc   1440
aggtaagatc aacaaaaagt tacatttttaa aatcacctaa cttttaataa atttatcaac   1500
aaagaccgta gataagtta ttaaaaatca tatttatctt aattttttctg aatgtaactt    1560 tttgaaaaag ttaaagttat cacgggatgt caacaaaaac tattgagaat tattgcatag    1620
gacaaaactt acctatagtt tctttggcat tttttttttgt tttcccatga aaattgaagt    1680
tttatgtcgg taacatgcat aataaatgtt tgcatgttga ttccaagata aaacttcaat    1740
tctaatcgga gaacaatggg aaaaacacct atggaaacta gttttgtac aattgcatat    1800 tgatttattt tattttattg tttgaattgt tgtttattt aaaaaaacaa acaggagact     1860
gcacttaatc atgttaagac cgctgggctt ctaggtgatg gatttggttc cacgcctgaa   1920
atgtgtaaga agaacctgat atgggtggtg actaagatgc aggttgtggt tgataaatat    1980
cctacatggt aagttggtgt gactagaaag aaccttttta atgtgtgaag aattgcaaag    2040
gcgtccatgc tcagatgtta aatcttcttt tgccttactc atctttgctt tgactttata    2100
tagtatctgg ttgaatttt ttgtacttct gtctttgttt ctgtcacttg tgccttttt     2160 tttcacaaaa atggaatgat agttgggaac ttgggattta aggcatgtat ggaatagatt    2220
gtgaattatt tttaaaaata tttttcatttt ttcaaaagct atctcaagaa actgtaaaaa   2280
aaattacttc tgcaatgtat ctgaaattct tcttggatga taatagatct aataaacata    2340
agctttgtat gtagtgaatt atgggaagtc ctttgcctta agtctgttat actgggtacg    2400
agaataatct cttagtaaa ttatgaatat gttcatctga agctgaatga atctatattt     2460
gcttcagggg tgatgttgtt caagtagaca cgtgggtttc tgcatcaggg aagaatggta    2520
tgcgtcgtga ttggcttgtg cgtgacgcca aaactggtga atcttgaca agagcctcca     2580 ggtagatatc agtttcagga atcctttttt tctgttgcct atagacatgt tttgaagagt    2640 tttttctgaat ctgaatgttt ctctctggtg atttggcact gcttttaatc tcacgaggct   2700
gtgtgaagtt atctattatc atatttactt tctcttaata caccactatt gaaaggcaat    2760
tcattacaga tttaagcata caaaattttg ttgatgataa ttttttaatc taccaacagt    2820
atctaatatc ttcttaattt gttattaagt accagccttc aacttgtgta catgttgcac    2880
cttggtgcta cgaacttata agcatttttct gattggttga gtttgatttt gattttgatg   2940
```

```
ttatgcagtg tttgggtcat gatgaataaa gtgacaagaa gactgtctaa aattcccgaa    3000
gaagtcaggg cagagataag ctcttatttt gtggattctg ctccagttgt gccagaggat    3060
aacagaaaac taaccaaact tgatgattca gctaatttca ttcgcactgg tttaagtgta    3120
tgcaaacttc ttttcaatta tgttatcatt gatttatttt ctaaaatgtc tcagatgttt    3180
tctgattaga tgttacgtat ctctattttc agcccagatg gcatgatcta gatgtgaatc    3240
agcatgttaa caatgtgaag tatgttgggt ggattctgga ggtagtcttc tgttcttgtt    3300
tcatattatt ctgtcttgaa tttctcttct ttttttggtg gatttattag caaggctcgt    3360
ctgacctttt gcaaggcagg ttgaatggtg attctgtaat tctgcaacac ccactttcct    3420
ttcaaaagac tctaaagaac ccattgggtc tatatgatag tgtgccaaag caactaccac    3480
tctgccagtg ttttcttttg agaggaatct gggtgtgagt agtaataaaa gtgttgagta    3540
agatcatgtt tcagatttcc agtaccgcca agtgaaagtt gtttgaagac agaagcattc    3600
aatttgttgt gggcatttga tgtctcgtat ggaagtggtt tatgctagtt tgaagtgtct    3660
tgaaacttga ttcatgagat aatggaatag taaaatggga tattggatgg gaaaaataga    3720
acaacacact tcctcgtatg atctttctgt gttcaactta tattgtcccc cttttttatta    3780 gtgtgttatt ttgaggggaa actaatgatt tatgtttggg taaagtatgt ttttaatcct    3840
tgtatttttg gtaagaattg gtatttgttt ccgtagttta acttttgaat aatttggttc    3900
ctgaacttta gaaaaataat ggtttttgt ccctcatcaa gatggttttc actgtgagga    3960
gagacaaaaa ccactaaacc actgttttat gtaaatttta tggagtattg accaaagttg    4020
aaattcagga atgaaaatca gatttcactg tgaaaatata aggacctaaa acatatttta    4080
ccctttatgt tttatttgtt tagtttgtta tgcatttgga ttttgatcag aacgtttaac    4140
caaagaatta tgctattgac tcctgcagag tgctccgcag ccacttttgg agagccatga    4200
gctatgtgcc atgacattgg agtacaggag ggagtgtggc aggaacagtg tgctagattc    4260
cctctctgat ctctccggtg ctgatgttgg aaacttagca gatgatggat ttttttgagtg    4320 caagcacttg cttcgacttg atgatggtgc tgagattgtg aggggcagga ccgaatggag    4380
gccaaaaccc ttaaacagaa actttggtca tgttttgagt caggttcctg ttccagcaga    4440
aagcacctga atctcattga ttgacatcaa tggaagagtg gcataattca tgttcccact    4500
tgcagattgg agagctttgc ttgttgcctt aaaatataaa acaaacaaaa aataataata    4560
aaaaaactcg gtcttatcat tttgtaatta aaaaatagct cctaccacta ctttcccttc    4620
tgctccattt cgtttatggt tatgctgctg ctaggtgtca tcaaaattta attgtttcat    4680
aaaaatggct aagcgtgtat attatagttc tttttttcttt tcccttataa gaaagatgca    4740
atattcctcg tgaacatacc aaaacaaata aagctatgta tagcttgcag gaaaggcctc    4800
ctgggtctct tttgtggttt ctattattag caattaattg cgcacacaaa tatgggtcat    4860
gtgacgggat ggattctagc tatatagaca acttcatatg accggcacta tcatgtagac    4920
atgtatgttc cgagagattt aaccatttat gatttatcc                            4959
```

<210> SEQ ID NO 35
<211> LENGTH: 1260
<212> TYPE: DNA
<213> ORGANISM: Glycine max
<220> FEATURE:
<221> NAME/KEY: mutation
<222> LOCATION: (136)..(136)
<223> OTHER INFORMATION: Sequence can be mutated from G to A.
<220> FEATURE:

```
<221> NAME/KEY: mutation
<222> LOCATION: (763)..(763)
<223> OTHER INFORMATION: Sequence can be mutated from G to A.
<220> FEATURE:
<221> NAME/KEY: mutation
<222> LOCATION: (988)..(988)
<223> OTHER INFORMATION: Sequence can be mutated from C to T.

<400> SEQUENCE: 35
atggttgcaa cagctgctac ggcgtcgttt ctccctgtgc cttcgccgga cgctggaaaa      60
gggaaaccca agggtggtgg tgcggcggc gtttctgtga acctcggagg actcaaagag      120
aagcaaggtt tgtgcggttg cttgcaggtc aaggcaaacg cacaagcccc tccgaagacc      180
atggagaagg ttgagaatga tttgccatgg ttgccgtcgt cgtcgatttc gcacgccccg      240
aggactttta taaatcagtt acctgactgg agcatgcttc tggccgccat caccaccgtg      300
ttcctcgcgg cggagaagca gtggatgatg ctggattgga agccgcgccg ccccgacatg      360
ctcattgacc cctttgggat tgggaagatc gtgcaggacg ggctcgtgtt caggcagaac      420
ttccccataa ggtcttacga aattggcgca gacaaaactg cgtcaataga gaccttaatg      480
aatcatttgc aggagactgc acttaatcat gttaagaccg ctgggcttct aggtgatgga      540
tttggttcca cgcctgaaat gtgtaagaag aacctgatat gggtggtgac taagatgcag      600
gttgtggttg ataaatatcc tacatggggt gatgttgttc aagtagacac gtgggtttct      660
gcatcaggga gaatggtat gcgtcgtgat tggcttgtgc gtgacgccaa actggtgaa       720 atcttgacaa gagcctccag tgtttgggtc atgatgaata agtgacaag aagactgtct     780 aaaattcccg aagaagtcag ggcagagata agctcttatt ttgtggattc tgctccagtt     840
gtgccagagg ataacagaaa actaaccaaa cttgatgatt cagctaattt cattcgcact     900
ggtttaagtc ccagatggca tgatctagat gtgaatcagc atgttaacaa tgtgaagtat     960
gttgggtgga ttctggagag tgctccgcag ccacttttgg agagccatga gctatgtgcc    1020
atgacattgg agtacaggag ggagtgtggc aggaacagtg tgctagattc cctctctgat    1080
ctctccggtg ctgatgttgg aaacttagca gatgatggat tttttgagtg caagcacttg    1140
cttcgacttg atgatggtgc tgagattgtg aggggcagga ccgaatggag gccaaaaccc    1200
ttaaacagaa actttggtca tgttttgagt caggttcctg ttccagcaga aagcacctga    1260

<210> SEQ ID NO 36
<211> LENGTH: 419
<212> TYPE: PRT
<213> ORGANISM: Glycine max
<220> FEATURE:
<221> NAME/KEY: MUTAGEN
<222> LOCATION: (46)..(46)
<223> OTHER INFORMATION: Sequence can be mutated from Gly to Ser.
<220> FEATURE:
<221> NAME/KEY: MUTAGEN
<222> LOCATION: (255)..(255)
<223> OTHER INFORMATION: Sequence can be mutated from Val to Met.
<220> FEATURE:
<221> NAME/KEY: MUTAGEN
<222> LOCATION: (330)..(330)
<223> OTHER INFORMATION: Sequence can be mutated from Gln to a premature
      stop.

<400> SEQUENCE: 36

Met Val Ala Thr Ala Ala Thr Ala Ser Phe Leu Pro Val Pro Ser Pro
1               5                   10                  15

Asp Ala Gly Lys Gly Lys Pro Lys Gly Gly Gly Gly Gly Val Ser
            20                  25                  30
```

-continued

```
Val Asn Leu Gly Gly Leu Lys Glu Lys Gln Gly Leu Cys Gly Cys Leu
        35                  40                  45

Gln Val Lys Ala Asn Ala Gln Ala Pro Pro Lys Thr Met Glu Lys Val
 50                  55                  60

Glu Asn Asp Leu Pro Trp Leu Pro Ser Ser Ile Ser His Ala Pro
 65              70                  75                  80

Arg Thr Phe Ile Asn Gln Leu Pro Asp Trp Ser Met Leu Leu Ala Ala
                 85                  90                  95

Ile Thr Thr Val Phe Leu Ala Ala Glu Lys Gln Trp Met Met Leu Asp
                100                 105                 110

Trp Lys Pro Arg Arg Pro Asp Met Leu Ile Asp Pro Phe Gly Ile Gly
            115                 120                 125

Lys Ile Val Gln Asp Gly Leu Val Phe Arg Gln Asn Phe Pro Ile Arg
    130                 135                 140

Ser Tyr Glu Ile Gly Ala Asp Lys Thr Ala Ser Ile Glu Thr Leu Met
145                 150                 155                 160

Asn His Leu Gln Glu Thr Ala Leu Asn His Val Lys Thr Ala Gly Leu
                165                 170                 175

Leu Gly Asp Gly Phe Gly Ser Thr Pro Glu Met Cys Lys Lys Asn Leu
            180                 185                 190

Ile Trp Val Val Thr Lys Met Gln Val Val Val Asp Lys Tyr Pro Thr
        195                 200                 205

Trp Gly Asp Val Val Gln Val Asp Thr Trp Val Ser Ala Ser Gly Lys
    210                 215                 220

Asn Gly Met Arg Arg Asp Trp Leu Val Arg Asp Ala Lys Thr Gly Glu
225                 230                 235                 240

Ile Leu Thr Arg Ala Ser Ser Val Trp Val Met Met Asn Lys Val Thr
                245                 250                 255

Arg Arg Leu Ser Lys Ile Pro Glu Glu Val Arg Ala Glu Ile Ser Ser
            260                 265                 270

Tyr Phe Val Asp Ser Ala Pro Val Val Pro Glu Asp Asn Arg Lys Leu
    275                 280                 285

Thr Lys Leu Asp Asp Ser Ala Asn Phe Ile Arg Thr Gly Leu Ser Pro
290                 295                 300

Arg Trp His Asp Leu Asp Val Asn Gln His Val Asn Asn Val Lys Tyr
305                 310                 315                 320

Val Gly Trp Ile Leu Glu Ser Ala Pro Gln Pro Leu Leu Glu Ser His
                325                 330                 335

Glu Leu Cys Ala Met Thr Leu Glu Tyr Arg Arg Glu Cys Gly Arg Asn
            340                 345                 350

Ser Val Leu Asp Ser Leu Ser Asp Leu Ser Gly Ala Asp Val Gly Asn
    355                 360                 365

Leu Ala Asp Asp Gly Phe Phe Glu Cys Lys His Leu Leu Arg Leu Asp
    370                 375                 380

Asp Gly Ala Glu Ile Val Arg Gly Arg Thr Glu Trp Arg Pro Lys Pro
385                 390                 395                 400

Leu Asn Arg Asn Phe Gly His Val Leu Ser Gln Val Pro Val Pro Ala
                405                 410                 415

Glu Ser Thr
```

SOYBEAN LINES WITH LOW SATURATED FATTY ACID AND HIGH OLEIC ACID CONTENTS

CROSS-REFERENCE TO RELATED APPLICATIONS

This application claims the benefit of U.S. Provisional Application No. 63/193,705, filed May 27, 2021, the contents of which are incorporated herein in their entirety.

INCORPORATION OF SEQUENCE LISTING

A paper copy of the Sequence Listing and a computer readable form of the Sequence Listing containing the file named "3512490.0043_sequence_listing_ST25," which is 102,421 bytes in size (as measured in MICROSOFT WINDOWS® EXPLORER) and was created on May 27, 2022, are provided herein and are herein incorporated by reference. This Sequence Listing consists of SEQ ID NOs: 1-36.

FIELD OF THE INVENTION

The present invention generally relates to compositions and methods to increase oleic acid content in soybeans.

BACKGROUND OF THE INVENTION

Soybean oil is an important edible resource of vegetable oil that makes up 53% in the U.S. vegetable oil consumption in 2017. As the predominant saturated fatty acid, palmitic acid (16:0) typically accounts for 11% in conventional soybean oil. Although elevated palmitic acid content improved oxidative stability of soybean oil, it also causes the decreases in oleic acid and oil contents. On the contrary, reducing palmitic acid content have been reported to reduce the risks of developing cardiovascular diseases for humans. To produce edible oil with <7% total saturates required by U.S. Food and Drug Administration, several soybean lines with reduced palmitic acid phenotype have been identified as potential genetic resources for developing low palmitic acid cultivars. In fatty acid biosynthetic pathway, 16:0-ACP fatty acid thioesterase (FATB) is the major targets to genetically reduce the levels of palmitic acid in soybean seeds.

Plant acyl-acyl carrier protein (ACP) thioesterase (TE), an enzyme terminates plastidial fatty acid biosynthesis, catalyzed acyl-ACP thioester bond hydrolysis to release free fatty acids and ACP. The substrate specificity of individual TEs is essential for the chain length of fatty acids exported from the plastid. In the online database named ThYme, there are 25 TE families, from which Family TE14 include bacterial and plant acyl-ACP TEs. Based on amino acid sequence alignment and substrate specificity, the plant TEs have been classified into two classes, FATA and FATB. The FATA class primarily hydrolyze 18:1-ACP with minor activity towards saturated acyl-ACP substrates, while FATB class show preference for acyl-ACP with saturated fatty acyl chains. They both contain two helix/multi-stranded sheet motifs (hotdog domains), in which residues in the N-terminal domain were found to affect substrate specificity of enzymes and highly conserved residues in the C-terminal domain involved in catalysis. Two thioesterases maintain the saturated/unsaturated balance of membrane fatty acids for normal plant growth under critical conditions.

As an allotetraploid crop species, soybean possess a highly duplicated genome that ~75% of genes present with multiple copies. Two whole-genome duplication events have occurred in soybean genome, including one shared by legume species 59 million years ago and another glycine-specific one around 13 million year ago. The number of genes involved in acyl lipid biosynthesis in soybean almost doubled compared to *Arabidopsis*. The gene families involved in fatty acid synthesis are generally much larger in soybean, such as omega-6 fatty acid desaturase (FAD2) with seven members. Such genetic redundancy drastically increases the complexity of genetic basis behind agronomical important traits but provide an invaluable resource for breeding desired phenotypes.

From mutagenized soybean lines, five quantitative trait loci (QTLs) have been associated with low palmitic acid phenotype, including fap1 in C1726, fap* in ELLP2, fap3 in A22, sop1 in J3, and fap$_{nc}$ in N79-2077-12. With the exception of fap$_{nc}$ allelic with fap3, fap1, fap3 and fap* are independent alleles conferring low palmitic acid content. At fap1, a disrupted splicing mutation in a 3-ketoacyl-ACP synthase enzyme III (GmKASIIIA) has been associated with reduced palmitic acid phenotype. At fap3, a single nucleotide polymorphism (SNP) have caused loss-of-function for GmFATB1A. Fap$_{nc}$ represented the second allele of GmFATB1A, in which a deletion is responsible for low palmitic acid phenotype. Two additional alleles of GmFATB1A from soybean mutant lines with 30% reduction in palmitic acid content have been identified. More recently, a 254-kb genomic deletion, including the GmFATB1A gene, have been reported to result in reduced palmitic acid content in soybean seeds. Alternatively, downregulation of GmFATB gene expression can reduce palmitic acid content in soybean seeds. In *Arabidopsis*, a FATB knockout mutant has shown not only the low saturated fatty acid content, but also slow seedling growth and low-viable seed development. However, no report on FATB soybean mutants with negative impact on soybean growth and seed quality has been released so far.

TILLING (Targeting Induced Local Lesions IN Genomes) has been developed to screen induced mutations from a chemical mutagenized population in early 2000s. It combines traditional chemical mutagenesis with a high-throughput mutation screening method. Ethylmethane sulfonate (EMS) is widely used as the most common chemical mutagen to randomly create point mutations in plant genome. A large number of TILLING populations have been well developed in a variety of plant species, such as barley, legume, maize, rice, sorghum, and wheat]. Using reverse genetic methods like TILLING, the gene functions have been studied for economically important traits in soybean, such as disease resistance and seed oil composition traits. Two missense mutations in the GmSHMT08 gene were identified in soybean cv.'Forrest' mutant populations and resulted in alternation of SCN-resistant phenotype. Three missense mutations in individual soybean lines were detected in the FAD2-1A and one of them led to high oleic acid and low linoleic acid contents in the seed oil]. However, the complex traits due to duplicated soybean genome dramatically lowered the efficiency of mutation screening in soybean. Using gel-based TILLING, a recent study showed that no mutations were found in either FAD2-1A or FAD2-1B from 2,000 EMS-mutagenized soybean lines, but five mutants in either of targeted genes were identified using forward phenotypic screening followed by targeted sequencing analysis. More recently, the adoption of exome capture sequencing enabled the high-throughput screening for hidden mutations in multiple homologous wheat genes controlling one trait.

The current invention is directed to the characterization of the soybean acyl-ACP thioesterase gene family through a comprehensive analysis of phylogeny, gene structure and expression, synteny, and conserved domain variations, and identified six additional members belonging to GmFATB gene family. One aspect of the present invention is directed to EMS-induced mutations in GmFATA1A, resulting in high oleic acid content in soybean seed. The novel alleles of GmFATB1A and GmFATB1B have also been discovered to be associated with low palmitic acid and high oleic acid contents. Therefore, these GmFAT mutants are valuable sources for breeding new soybean lines with low saturated fatty acid and high oleic acid contents.

DESCRIPTION OF THE DRAWINGS

The following drawings form part of the present specification and are included to further demonstrate certain aspects of the present invention. The present invention may be better understood by reference to one or more of these drawings in combination with the detailed description of specific embodiments presented herein. However, those of skill in the art will understand that the drawings, described below, are for illustrative purposes only. The drawings are not intended to limit the scope of the present invention in any way.

FIG. 6 is a table showing the predicted 13 substrate specificity sites and 3 conserved catalytic sites of soybean acyl-ACP thioesterase genes. $^a$: Numbering of the residues are according to the sequence of GmFATA1A. $^b$: Previously reported substrate specificity sites of acyl-ACP thioesterases. C: The catalytic sites of acyl-ACP thioesterases.

FIG. 8 is a table showing a summary of mutations in five soybean acyl-ACP thioesterase genes identified by TbyTCS.

FIG. 9 is a table showing a summary of mutants in GmFATA and GmFATB genes identified by TILLING-by-Sequencing+ and their fatty acids phenotype.

DETAILED DESCRIPTION OF THE INVENTION

Transgenic Soybean Plants

Figure 1:
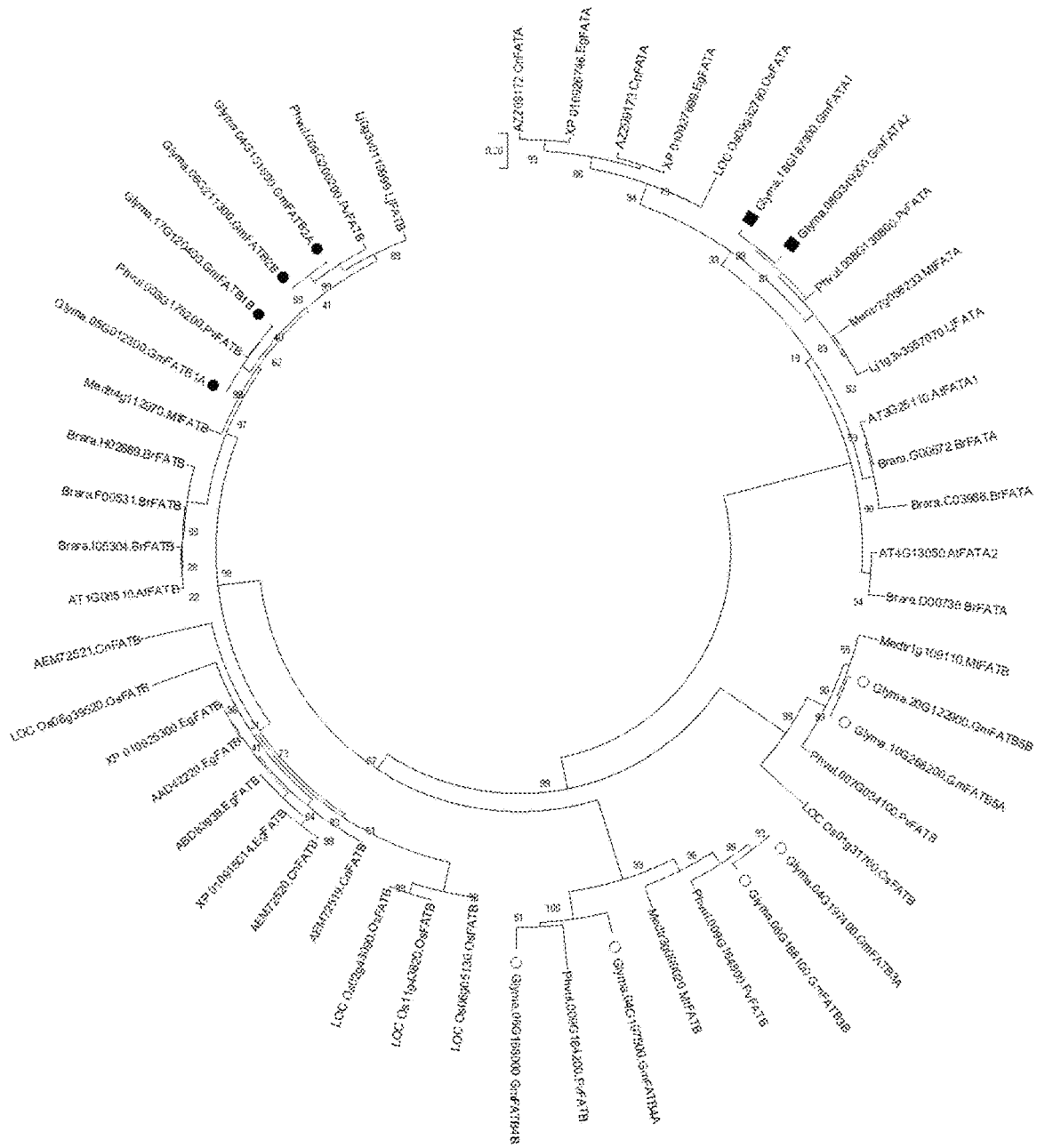
FIG. 1 is a schematic of the phylogenetic tree of acyl-ACP thioesterase gene family from nine plant species. The protein sequences of all acyl-ACP thioesterases were subjected to a MUSCLE multiple alignment and phylogenetic tree was constructed by maximum likelihood (ML) method using Mega X. The two members of soybean FATA gene subfamily were labelled with filled squares. The previously identified four members of soybean FATB1/2 subfamilies were marked with filled circles while the newly identified members of FATB3/4/5 subfamilies in this study were labelled with empty circles The name and abbreviation of plant species used for the analysis are: *Arabidopsis thaliana* (At); *Glycine max* (Gm); *Phaseolus vulgaris* (Pv); *Medicago truncatula* (Mt); *Lotus japonicas* (Lj); *Brassica rapa* (Br); *Cocos nucifera* (Cn); *Elaeis guineensis* (Eg); *Oriza sativa* (Os).

One embodiment of the present invention is directed to a transgenic soybean plant with increased oleic acid content comprising a polynucleotide encoding a fatty acid thioesterase (FAT) related promoter that functions in the soybean plant operably linked to a polynucleotide encoding a polypeptide having FAT activity.

The polynucleotide encoding a FAT related promoter may comprise any wild type FAT promoter sequence, or a sequence at least 95% identical thereto, or a full length complement thereof, or a functional fragment thereof. In certain embodiments, the wild type FAT promoter sequence can be selected from the group consisting of a promoter sequence of FATA1A, FATA1B, FATB1A, FATB2A, FATB3A, FATB4A, FATB5A, FATB1B, FATB2B, FATB3B, FATB4B, and FATB5B. In certain embodiments, the wild type FAT promoter sequence can be selected from the group consisting of a promoter sequence of FATA1A, FATB1A, FATB1B, FATB2A, and FATB2B.

In some embodiments, the polynucleotide encoding a polypeptide having FAT activity may comprise any wild type FAT genomic or coding sequence, or a sequence at least 95% identical thereto, or a full length complement thereof, or a functional fragment thereof. In one embodiment, the wild type FAT genomic or coding sequence can be selected from the group consisting of a genomic or coding sequence of FATA1A, FATA1B, FATB1A, FATB2A, FATB3A, FATB4A, FATB5A, FATB1B, FATB2B, FATB3B, FATB4B, and FATB5B. In certain embodiments, the wild type FAT genomic or coding sequence can be selected from the group consisting of a genomic or coding sequence of FATA1A, FATB1A, FATB1B, FATB2A, and FATB2B.

The polypeptide having FAT activity may comprise any wild type FAT amino acid sequence, or a sequence at least 95% identical thereto, or a full-length complement thereof, or a functional fragment thereof. In one embodiment, the wild type FAT amino acid sequence can be selected from the group consisting of an amino acid sequence of FATA1A, FATA1B, FATB1A, FATB2A, FATB3A, FATB4A, FATB5A, FATB1B, FATB2B, FATB3B, FATB4B, and FATB5B. In certain embodiments, the wild type FAT amino acid sequence can be selected from the group consisting of an amino acid sequence of FATA1A, FATB1A, FATB1B, FATB2A, and FATB2B.

In one embodiment, the polynucleotide encoding a FAT related promoter may comprise any wild type FATA1A promoter sequence, or a sequence at least 95% identical thereto, or a full length complement thereof, or a functional fragment thereof. In certain embodiments, the wild type FATA1A promoter sequence can comprise the wild type "Forrest" FATA1A promoter sequence (SEQ ID NO: 17), or a sequence at least 95% identical thereto, or a full-length complement thereof, or a functional fragment thereof.

The polynucleotide encoding a polypeptide having FAT activity may comprise any wild type FATA1A genomic or coding sequence, or a sequence at least 95% identical thereto, or a full length complement thereof, or a functional fragment thereof. In certain embodiments, the wild type FATA1A genomic sequence may comprise the wild type "Forrest" FATA1A genomic sequence (SEQ ID NO: 18), or a sequence at least 95% identical thereto, or a full-length complement thereof, or a functional fragment thereof. In certain embodiments, the wild type FATA1A coding sequence may comprise the wild type "Forrest" FATA1A coding sequence (SEQ ID NO: 19), or a sequence at least 95% identical thereto, or a full-length complement thereof, or a functional fragment thereof, and may further comprise one or more mutations of the wild type "Forrest" FATA1A coding sequence selected from the group consisting of: C110T, G163T, C437T, C692T, G830A, and G928A.

The polypeptide having FAT activity may comprise the wild type "Forrest" FATA1A amino acid sequence (SEQ ID NO: 20), or a sequence at least 95% identical thereto, or a full-length complement thereof, or a functional fragment thereof, and may further comprise one or more mutations of the wild type "Forrest" FATA1A amino acid sequence selected from the group consisting of: S37F, A55T, T146I, A231V, G277E, and V310I.

The polynucleotide encoding a FAT related promoter may comprise any wild type FATB1A promoter sequence, or a sequence at least 95% identical thereto, or a full length complement thereof, or a functional fragment thereof. In certain embodiments, the wild type FATB1A promoter sequence can comprise the wild type "Forrest" FATB1A promoter sequence (SEQ ID NO: 21), or a sequence at least 95% identical thereto, or a full-length complement thereof, or a functional fragment thereof.

The polynucleotide encoding a polypeptide having FAT activity may comprise any wild type FATB1A genomic or coding sequence, or a sequence at least 95% identical thereto, or a full length complement thereof, or a functional fragment thereof. In certain embodiments, the wild type FATB1A genomic sequence may comprise the wild type "Forrest" FATB1A genomic sequence (SEQ ID NO: 22), or a sequence at least 95% identical thereto, or a full-length complement thereof, or a functional fragment thereof. In certain embodiments, the wild type FATB1A coding sequence may comprise the wild type "Forrest" FATB1A coding sequence (SEQ ID NO: 23), or a sequence at least 95% identical thereto, or a full-length complement thereof, or a functional fragment thereof, and may further comprise one or more mutations of the wild type "Forrest" FATB1A coding sequence selected from the group consisting of: C52T, G382A, G539A, G668A, G850A, and G1111A.

The polypeptide having FAT activity may comprise the wild type "Forrest" FATB1A amino acid sequence (SEQ ID NO: 24), or a sequence at least 95% identical thereto, or a full-length complement thereof, or a functional fragment thereof, and may further comprise one or more mutations of the wild type "Forrest" FATB1A amino acid sequence selected from the group consisting of: P18L, G128R, G180D, G223E, D284N, and A371T.

The polynucleotide encoding a FAT related promoter may comprise any wild type FATB1B promoter sequence, or a sequence at least 95% identical thereto, or a full length complement thereof, or a functional fragment thereof. In certain embodiments, the wild type FATB1B promoter sequence can comprise the wild type "Forrest" FATB1B promoter sequence (SEQ ID NO: 25), or a sequence at least 95% identical thereto, or a full-length complement thereof, or a functional fragment thereof.

The polynucleotide encoding a polypeptide having FAT activity may comprise any wild type FATB1B genomic or coding sequence, or a sequence at least 95% identical thereto, or a full length complement thereof, or a functional fragment thereof. In certain embodiments, the wild type FATB1B genomic sequence may comprise the wild type "Forrest" FATB1B genomic sequence (SEQ ID NO: 26), or a sequence at least 95% identical thereto, or a full-length complement thereof, or a functional fragment thereof. In certain embodiments, the wild type FATB1B coding sequence may comprise the wild type "Forrest" FATB1B coding sequence (SEQ ID NO: 27), or a sequence at least 95% identical thereto, or a full-length complement thereof, or a functional fragment thereof, and may further comprise one or more mutations of the wild type "Forrest" FATB1B coding sequence selected from the group consisting of: C352T, T380*, G383A, G520A, and G1043A.

The polypeptide having FAT activity may comprise the wild type "Forrest" FATB1B amino acid sequence (SEQ ID NO: 28), or a sequence at least 95% identical thereto, or a full-length complement thereof, or a functional fragment thereof, and may further comprise one or more mutations of the wild type "Forrest" FATB1B amino acid sequence selected from the group consisting of: P118S, I127X, G128E, A174T, and R348K.

The polynucleotide encoding a FAT related promoter may comprise any wild type FATB2A promoter sequence, or a sequence at least 95% identical thereto, or a full length complement thereof, or a functional fragment thereof. In certain embodiments, the wild type FATB2A promoter sequence can comprise the wild type "Forrest" FATB2A promoter sequence (SEQ ID NO: 29), or a sequence at least 95% identical thereto, or a full-length complement thereof, or a functional fragment thereof.

The polynucleotide encoding a polypeptide having FAT activity may comprise any wild type FATB2A genomic or coding sequence, or a sequence at least 95% identical thereto, or a full length complement thereof, or a functional fragment thereof. In certain embodiments, the wild type FATB2A genomic sequence may comprise the wild type "Forrest" FATB2A genomic sequence (SEQ ID NO: 30), or a sequence at least 95% identical thereto, or a full-length complement thereof, or a functional fragment thereof. In certain embodiments, the wild type FATB2A coding sequence may comprise the wild type "Forrest" FATB2A coding sequence (SEQ ID NO: 31), or a sequence at least 95% identical thereto, or a full-length complement thereof, or a functional fragment thereof, and may further comprise one or more mutations of the wild type "Forrest" FATB2A coding sequence selected from the group consisting of: C47T, G1117A, G1154A, and G1184A.

The polypeptide having FAT activity may comprise the wild type "Forrest" FATB2A amino acid sequence (SEQ ID NO: 32), or a sequence at least 95% identical thereto, or a full-length complement thereof, or a functional fragment thereof, and may further comprise one or more mutations of the wild type "Forrest" FATB2A amino acid sequence selected from the group consisting of: P16L, A373T, R385Q, and G395D.

The polynucleotide encoding a FAT related promoter may comprise any wild type FATB2B promoter sequence, or a sequence at least 95% identical thereto, or a full length complement thereof, or a functional fragment thereof. In certain embodiments, the wild type FATB2B promoter sequence can comprise the wild type "Forrest" FATB2B promoter sequence (SEQ ID NO: 33), or a sequence at least 95% identical thereto, or a full-length complement thereof, or a functional fragment thereof.

The polynucleotide encoding a polypeptide having FAT activity may comprise any wild type FATB2B genomic or coding sequence, or a sequence at least 95% identical thereto, or a full length complement thereof, or a functional fragment thereof. In certain embodiments, the wild type FATB2B genomic sequence may comprise the wild type "Forrest" FATB2B genomic sequence (SEQ ID NO: 34), or a sequence at least 95% identical thereto, or a full-length complement thereof, or a functional fragment thereof. In certain embodiments, the wild type FATB2B coding sequence may comprise the wild type "Forrest" FATB2B coding sequence (SEQ ID NO: 35), or a sequence at least 95% identical thereto, or a full-length complement thereof, or a functional fragment thereof, and may further comprise one or more mutations of the wild type "Forrest" FATB2B coding sequence selected from the group consisting of: G136A, G763A, and C988T.

The polypeptide having FAT activity may comprise the wild type "Forrest" FATB2B amino acid sequence (SEQ ID NO: 36), or a sequence at least 95% identical thereto, or a full-length complement thereof, or a functional fragment thereof, and may further comprise one or more mutations of the wild type "Forrest" FATB2B amino acid sequence selected from the group consisting of: G46S, V255M, and Q330*.

The transgenic soybean plant with increased oleic acid content may comprise more than one polynucleotide encoding a FAT related promoter that functions in the soybean plant, provided that each polynucleotide encoding a FAT related promoter that functions in the soybean plant is operably linked to a polynucleotide encoding a polypeptide having FAT activity.

The more than one polynucleotide encoding a FAT related promoter may be selected from the group consisting of: (i) any wild type FATA1A promoter sequence, or a sequence at least 95% identical thereto, or a full length complement thereof, or a functional fragment thereof, wherein the polypeptide having FAT activity comprises the wild type "Forrest" FATA1A amino acid sequence (SEQ ID NO: 20), or a sequence at least 95% identical thereto, or a full-length complement thereof, or a functional fragment thereof, and further comprises one or more mutations of the wild type "Forrest" FATA1A amino acid sequence (SEQ ID NO: 20) selected from the group consisting of: S37F, A55T, T146I, A231V, G277E, and V310I; (ii) any wild type FATB1A promoter sequence, or a sequence at least 95% identical thereto, or a full length complement thereof, or a functional fragment thereof, wherein the polypeptide having FAT activity comprises the wild type "Forrest" FATB1A amino acid sequence (SEQ ID NO: 24), or a sequence at least 95% identical thereto, or a full-length complement thereof, or a functional fragment thereof, and further comprises one or more mutations of the wild type "Forrest" FATB1A amino acid sequence (SEQ ID NO: 24) selected from the group consisting of: P18L, G128R, G180D, G223E, D284N, and A371T; (iii) any wild type FATB1B promoter sequence, or a sequence at least 95% identical thereto, or a full length complement thereof, or a functional fragment thereof, wherein the polypeptide having FAT activity comprises the wild type "Forrest" FATB1B amino acid sequence (SEQ ID NO: 28), or a sequence at least 95% identical thereto, or a full-length complement thereof, or a functional fragment thereof, and further comprises one or more mutations of the wild type "Forrest" FATB1B amino acid sequence (SEQ ID NO: 28) selected from the group consisting of: P118S, I127X, G128E, A174T, and R348K; (iv) any wild type FATB2A promoter sequence, or a sequence at least 95% identical thereto, or a full length complement thereof, or a functional fragment thereof, wherein the polypeptide having FAT activity comprises the wild type "Forrest" FATB2A amino acid sequence (SEQ ID NO: 32), or a sequence at least 95% identical thereto, or a full-length complement thereof, or a functional fragment thereof, and further comprises one or more mutations of the wild type "Forrest" FATB2A amino acid sequence (SEQ ID NO: 32) selected from the group consisting of: P16L, A373T, R385Q, and G395D; and (v) any wild type FATB2B promoter sequence, or a sequence at least 95% identical thereto, or a full length complement thereof, or a functional fragment thereof, wherein the polypeptide having FAT activity comprises the wild type "Forrest" FATB2B amino acid sequence (SEQ ID NO: 36), or a sequence at least 95% identical thereto, or a full-length complement thereof, or a functional fragment thereof, and further comprises one or more mutations of the wild type "Forrest" FATB2B amino acid sequence (SEQ ID NO: 36) selected from the group consisting of: G46S, V255M, and Q330*.

The transgenic soybean plant may have increased oleic acid content compared to a control soybean plant lacking the polynucleotide encoding a polypeptide having FAT activity as described above. The increased oleic acid content may comprise an at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or at least about 100% increase in oleic acid content as compared to a control soybean plant lacking the polynucleotide encoding a polypeptide having FAT activity as described above.

An additional embodiment of the present invention is a plant part of any of the transgenic soybean plants described above.

Agronomically Elite Soybean Varieties

Another embodiment of the present invention is a plant of an agronomically elite soybean variety with increased oleic acid content comprising a polynucleotide encoding a fatty acid thioesterase (FAT) related promoter that functions in the soybean plant operably linked to a polynucleotide encoding a polypeptide having FAT activity.

The polynucleotide encoding a FAT related promoter may comprise any wild type FAT promoter sequence, or a sequence at least 95% identical thereto, or a full length complement thereof, or a functional fragment thereof. In certain embodiments, the wild type FAT promoter sequence can be selected from the group consisting of a promoter sequence of FATA1A, FATA1B, FATB1A, FATB2A, FATB3A, FATB4A, FATB5A, FATB1B, FATB2B, FATB3B, FATB4B, and FATB5B. In certain embodiments, the wild type FAT promoter sequence can be selected from the group consisting of a promoter sequence of FATA1A, FATB1A, FATB1B, FATB2A, and FATB2B.

In some embodiments, the polynucleotide encoding a polypeptide having FAT activity may comprise any wild type FAT genomic or coding sequence, or a sequence at least 95% identical thereto, or a full length complement thereof, or a functional fragment thereof. In one embodiment, the wild type FAT genomic or coding sequence can be selected from the group consisting of a genomic or coding sequence of FATA1A, FATA1B, FATB1A, FATB2A, FATB3A, FATB4A, FATB5A, FATB1B, FATB2B, FATB3B, FATB4B, and FATB5B. In certain embodiments, the wild type FAT genomic or coding sequence can be selected from the group consisting of a genomic or coding sequence of FATA1A, FATB1A, FATB1B, FATB2A, and FATB2B.

The polypeptide having FAT activity may comprise any wild type FAT amino acid sequence, or a sequence at least 95% identical thereto, or a full-length complement thereof, or a functional fragment thereof. In one embodiment, the wild type FAT amino acid sequence can be selected from the group consisting of an amino acid sequence of FATA1A, FATA1B, FATB1A, FATB2A, FATB3A, FATB4A, FATB5A, FATB1B, FATB2B, FATB3B, FATB4B, and FATB5B. In certain embodiments, the wild type FAT amino acid sequence can be selected from the group consisting of an amino acid sequence of FATA1A, FATB1A, FATB1B, FATB2A, and FATB2B.

The polynucleotide encoding a FAT related promoter may comprise any wild type FATA1A promoter sequence, or a sequence at least 95% identical thereto, or a full length complement thereof, or a functional fragment thereof. In certain embodiments, the wild type FATA1A promoter sequence can comprise the wild type "Forrest" FATA1A promoter sequence (SEQ ID NO: 17), or a sequence at least 95% identical thereto, or a full-length complement thereof, or a functional fragment thereof.

The polynucleotide encoding a polypeptide having FAT activity may comprise any wild type FATA1A genomic or coding sequence, or a sequence at least 95% identical thereto, or a full length complement thereof, or a functional fragment thereof. In certain embodiments, the wild type FATA1A genomic sequence may comprise the wild type "Forrest" FATA1A genomic sequence (SEQ ID NO: 18), or a sequence at least 95% identical thereto, or a full-length complement thereof, or a functional fragment thereof. In certain embodiments, the wild type FATA1A coding sequence may comprise the wild type "Forrest" FATA1A coding sequence (SEQ ID NO: 19), or a sequence at least 95% identical thereto, or a full-length complement thereof, or a functional fragment thereof, and may further comprise one or more mutations of the wild type "Forrest" FATA1A coding sequence selected from the group consisting of: C110T, G163T, C437T, C692T, G830A, and G928A.

The polypeptide having FAT activity may comprise the wild type "Forrest" FATA1A amino acid sequence (SEQ ID NO: 20), or a sequence at least 95% identical thereto, or a full-length complement thereof, or a functional fragment thereof, and may further comprise one or more mutations of the wild type "Forrest" FATA1A amino acid sequence selected from the group consisting of: S37F, A55T, T146I, A231V, G277E, and V310I.

The polynucleotide encoding a FAT related promoter may comprise any wild type FATB1A promoter sequence, or a sequence at least 95% identical thereto, or a full length complement thereof, or a functional fragment thereof. In certain embodiments, the wild type FATB1A promoter sequence can comprise the wild type "Forrest" FATB1A promoter sequence (SEQ ID NO: 21), or a sequence at least 95% identical thereto, or a full-length complement thereof, or a functional fragment thereof.

The polynucleotide encoding a polypeptide having FAT activity may comprise any wild type FATB1A genomic or coding sequence, or a sequence at least 95% identical thereto, or a full length complement thereof, or a functional fragment thereof. In certain embodiments, the wild type FATB1A genomic sequence may comprise the wild type "Forrest" FATB1A genomic sequence (SEQ ID NO: 22), or a sequence at least 95% identical thereto, or a full-length complement thereof, or a functional fragment thereof. In certain embodiments, the wild type FATB1A coding sequence may comprise the wild type "Forrest" FATB1A coding sequence (SEQ ID NO: 23), or a sequence at least 95% identical thereto, or a full-length complement thereof, or a functional fragment thereof, and may further comprise one or more mutations of the wild type "Forrest" FATB1A coding sequence selected from the group consisting of: C52T, G382A, G539A, G668A, G850A, and G1111A.

The polypeptide having FAT activity may comprise the wild type "Forrest" FATB1A amino acid sequence (SEQ ID NO: 24), or a sequence at least 95% identical thereto, or a full-length complement thereof, or a functional fragment thereof, and may further comprise one or more mutations of the wild type "Forrest" FATB1A amino acid sequence selected from the group consisting of: P18L, G128R, G180D, G223E, D284N, and A371T.

The polynucleotide encoding a FAT related promoter may comprise any wild type FATB1B promoter sequence, or a sequence at least 95% identical thereto, or a full length complement thereof, or a functional fragment thereof. In certain embodiments, the wild type FATB1B promoter sequence can comprise the wild type "Forrest" FATB1B promoter sequence (SEQ ID NO: 25), or a sequence at least 95% identical thereto, or a full-length complement thereof, or a functional fragment thereof.

The polynucleotide encoding a polypeptide having FAT activity may comprise any wild type FATB1B genomic or coding sequence, or a sequence at least 95% identical thereto, or a full length complement thereof, or a functional fragment thereof. In certain embodiments, the wild type FATB1B genomic sequence may comprise the wild type "Forrest" FATB1B genomic sequence (SEQ ID NO: 26), or a sequence at least 95% identical thereto, or a full-length complement thereof, or a functional fragment thereof. In certain embodiments, the wild type FATB1B coding sequence may comprise the wild type "Forrest" FATB1B coding sequence (SEQ ID NO: 27), or a sequence at least 95% identical thereto, or a full-length complement thereof, or a functional fragment thereof, and may further comprise one or more mutations of the wild type "Forrest" FATB1B coding sequence selected from the group consisting of: C352T, T380*, G383A, G520A, and G1043A.

The polypeptide having FAT activity may comprise the wild type "Forrest" FATB1B amino acid sequence (SEQ ID NO: 28), or a sequence at least 95% identical thereto, or a full-length complement thereof, or a functional fragment thereof, and may further comprise one or more mutations of the wild type "Forrest" FATB1B amino acid sequence selected from the group consisting of: P118S, I127X, G128E, A174T, and R348K.

The polynucleotide encoding a FAT related promoter may comprise any wild type FATB2A promoter sequence, or a sequence at least 95% identical thereto, or a full length complement thereof, or a functional fragment thereof. In certain embodiments, the wild type FATB2A promoter sequence can comprise the wild type "Forrest" FATB2A promoter sequence (SEQ ID NO: 29), or a sequence at least 95% identical thereto, or a full-length complement thereof, or a functional fragment thereof.

The polynucleotide encoding a polypeptide having FAT activity may comprise any wild type FATB2A genomic or coding sequence, or a sequence at least 95% identical thereto, or a full length complement thereof, or a functional fragment thereof. In certain embodiments, the wild type FATB2A genomic sequence may comprise the wild type "Forrest" FATB2A genomic sequence (SEQ ID NO: 30), or a sequence at least 95% identical thereto, or a full-length complement thereof, or a functional fragment thereof. In certain embodiments, the wild type FATB2A coding sequence may comprise the wild type "Forrest" FATB2A coding sequence (SEQ ID NO: 31), or a sequence at least 95% identical thereto, or a full-length complement thereof, or a functional fragment thereof, and may further comprise one or more mutations of the wild type "Forrest" FATB2A coding sequence selected from the group consisting of: C47T, G1117A, G1154A, and G1184A.

The polypeptide having FAT activity may comprise the wild type "Forrest" FATB2A amino acid sequence (SEQ ID NO: 32), or a sequence at least 95% identical thereto, or a full-length complement thereof, or a functional fragment thereof, and may further comprise one or more mutations of the wild type "Forrest" FATB2A amino acid sequence selected from the group consisting of: P16L, A373T, R385Q, and G395D.

The polynucleotide encoding a FAT related promoter may comprise any wild type FATB2B promoter sequence, or a sequence at least 95% identical thereto, or a full length complement thereof, or a functional fragment thereof. In certain embodiments, the wild type FATB2B promoter sequence can comprise the wild type "Forrest" FATB2B promoter sequence (SEQ ID NO: 33), or a sequence at least 95% identical thereto, or a full-length complement thereof, or a functional fragment thereof.

The polynucleotide encoding a polypeptide having FAT activity may comprise any wild type FATB2B genomic or coding sequence, or a sequence at least 95% identical thereto, or a full length complement thereof, or a functional fragment thereof. In certain embodiments, the wild type FATB2B genomic sequence may comprise the wild type "Forrest" FATB2B genomic sequence (SEQ ID NO: 34), or a sequence at least 95% identical thereto, or a full-length complement thereof, or a functional fragment thereof. In certain embodiments, the wild type FATB2B coding sequence may comprise the wild type "Forrest" FATB2B coding sequence (SEQ ID NO: 35), or a sequence at least 95% identical thereto, or a full-length complement thereof, or a functional fragment thereof, and may further comprise one or more mutations of the wild type "Forrest" FATB2B coding sequence selected from the group consisting of: G136A, G763A, and C988T.

The polypeptide having FAT activity may comprise the wild type "Forrest" FATB2B amino acid sequence (SEQ ID NO: 36), or a sequence at least 95% identical thereto, or a full-length complement thereof, or a functional fragment thereof, and may further comprise one or more mutations of the wild type "Forrest" FATB2B amino acid sequence selected from the group consisting of: G46S, V255M, and Q330*.

The plant with increased oleic acid content may comprise more than one polynucleotide encoding a FAT related promoter that functions in the soybean plant, provided that each polynucleotide encoding a FAT related promoter that functions in the soybean plant is operably linked to a polynucleotide encoding a polypeptide having FAT activity.

The more than one polynucleotide encoding a FAT related promoter may be selected from the group consisting of: (i) any wild type FATA1A promoter sequence, or a sequence at least 95% identical thereto, or a full length complement thereof, or a functional fragment thereof, wherein the polypeptide having FAT activity comprises the wild type "Forrest" FATA1A amino acid sequence (SEQ ID NO: 20), or a sequence at least 95% identical thereto, or a full-length complement thereof, or a functional fragment thereof, and further comprises one or more mutations of the wild type "Forrest" FATA1A amino acid sequence (SEQ ID NO: 20) selected from the group consisting of: S37F, A55T, T146I, A231V, G277E, and V310I; (ii) any wild type FATB1A promoter sequence, or a sequence at least 95% identical thereto, or a full length complement thereof, or a functional fragment thereof, wherein the polypeptide having FAT activity comprises the wild type "Forrest" FATB1A amino acid sequence (SEQ ID NO: 24), or a sequence at least 95% identical thereto, or a full-length complement thereof, or a functional fragment thereof, and further comprises one or more mutations of the wild type "Forrest" FATB1A amino acid sequence (SEQ ID NO: 24) selected from the group consisting of: P18L, G128R, G180D, G223E, D284N, and A371T; (iii) any wild type FATB1B promoter sequence, or a sequence at least 95% identical thereto, or a full length complement thereof, or a functional fragment thereof, wherein the polypeptide having FAT activity comprises the wild type "Forrest" FATB1B amino acid sequence (SEQ ID NO: 28), or a sequence at least 95% identical thereto, or a full-length complement thereof, or a functional fragment thereof, and further comprises one or more mutations of the wild type "Forrest" FATB1B amino acid sequence (SEQ ID NO: 28) selected from the group consisting of: P118S, I127X, G128E, A174T, and R348K; (iv) any wild type FATB2A promoter sequence, or a sequence at least 95% identical thereto, or a full length complement thereof, or a functional fragment thereof, wherein the polypeptide having FAT activity comprises the wild type "Forrest" FATB2A amino acid sequence (SEQ ID NO: 32), or a sequence at least 95% identical thereto, or a full-length complement thereof, or a functional fragment thereof, and further comprises one or more mutations of the wild type "Forrest" FATB2A amino acid sequence (SEQ ID NO: 32) selected from the group consisting of: P16L, A373T, R385Q, and G395D; and (v) any wild type FATB2B promoter sequence, or a sequence at least 95% identical thereto, or a full length complement thereof, or a functional fragment thereof, wherein the polypeptide having FAT activity comprises the wild type "Forrest" FATB2B amino acid sequence (SEQ ID NO: 36), or a sequence at least 95% identical thereto, or a full-length complement thereof, or a functional fragment thereof, and further comprises one or more mutations of the wild type "Forrest" FATB2B amino acid sequence (SEQ ID NO: 36) selected from the group consisting of: G46S, V255M, and Q330*.

The plant may have increased oleic acid content compared to a control soybean plant lacking the polynucleotide encoding a polypeptide having FAT activity as described above. The increased oleic acid content may comprise an at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or at least about 100% increase in oleic acid content as compared to a control soybean plant lacking the polynucleotide encoding a polypeptide having FAT activity as described above.

An additional embodiment of the present invention is a plant part of any of the plants described above.

Methods of Increasing Oleic Acid Content

Another embodiment of the present invention is a method of increasing oleic acid content of a soybean plant comprising transforming the soybean plant with a polynucleotide encoding a fatty acid thioesterase (FAT) related promoter that functions in the soybean plant operably linked to a polynucleotide encoding a polypeptide having FAT activity.

The polynucleotide encoding a FAT related promoter may comprise any wild type FAT promoter sequence, or a sequence at least 95% identical thereto, or a full length complement thereof, or a functional fragment thereof. In certain embodiments, the wild type FAT promoter sequence can be selected from the group consisting of a promoter sequence of FATA1A, FATA1B, FATB1A, FATB2A, FATB3A, FATB4A, FATB5A, FATB1B, FATB2B, FATB3B, FATB4B, and FATB5B. In certain embodiments, the wild type FAT promoter sequence can be selected from the group consisting of a promoter sequence of FATA1A, FATB1A, FATB1B, FATB2A, and FATB2B.

In some embodiments, the polynucleotide encoding a polypeptide having FAT activity may comprise any wild type FAT genomic or coding sequence, or a sequence at least 95% identical thereto, or a full length complement thereof, or a functional fragment thereof. In one embodiment, the wild type FAT genomic or coding sequence can be selected from the group consisting of a genomic or coding sequence of FATA1A, FATA1B, FATB1A, FATB2A, FATB3A, FATB4A, FATB5A, FATB1B, FATB2B, FATB3B, FATB4B, and FATB5B. In certain embodiments, the wild type FAT genomic or coding sequence can be selected from the group consisting of a genomic or coding sequence of FATA1A, FATB1A, FATB1B, FATB2A, and FATB2B.

The polypeptide having FAT activity may comprise any wild type FAT amino acid sequence, or a sequence at least 95% identical thereto, or a full-length complement thereof, or a functional fragment thereof. In one embodiment, the wild type FAT amino acid sequence can be selected from the group consisting of an amino acid sequence of FATA1A, FATA1B, FATB1A, FATB2A, FATB3A, FATB4A, FATB5A, FATB1B, FATB2B, FATB3B, FATB4B, and FATB5B. In certain embodiments, the wild type FAT amino acid sequence can be selected from the group consisting of an amino acid sequence of FATA1A, FATB1A, FATB1B, FATB2A, and FATB2B.

The polynucleotide encoding a FAT related promoter may comprise any wild type FATA1A promoter sequence, or a sequence at least 95% identical thereto, or a full length complement thereof, or a functional fragment thereof. In certain embodiments, the wild type FATA1A promoter sequence can comprise the wild type "Forrest" FATA1A promoter sequence (SEQ ID NO: 17), or a sequence at least 95% identical thereto, or a full-length complement thereof, or a functional fragment thereof.

The polynucleotide encoding a polypeptide having FAT activity may comprise any wild type FATA1A genomic or coding sequence, or a sequence at least 95% identical thereto, or a full length complement thereof, or a functional fragment thereof. In certain embodiments, the wild type FATA1A genomic sequence may comprise the wild type "Forrest" FATA1A genomic sequence (SEQ ID NO: 18), or a sequence at least 95% identical thereto, or a full-length complement thereof, or a functional fragment thereof. In certain embodiments, the wild type FATA1A coding sequence may comprise the wild type "Forrest" FATA1A coding sequence (SEQ ID NO: 19), or a sequence at least 95% identical thereto, or a full-length complement thereof, or a functional fragment thereof, and may further comprise one or more mutations of the wild type "Forrest" FATA1A coding sequence selected from the group consisting of: C110T, G163T, C437T, C692T, G830A, and G928A.

The polypeptide having FAT activity may comprise the wild type "Forrest" FATA1A amino acid sequence (SEQ ID NO: 20), or a sequence at least 95% identical thereto, or a full-length complement thereof, or a functional fragment thereof, and may further comprise one or more mutations of the wild type "Forrest" FATA1A amino acid sequence selected from the group consisting of: S37F, A55T, T146I, A231V, G277E, and V310I.

The polynucleotide encoding a FAT related promoter may comprise any wild type FATB1A promoter sequence, or a sequence at least 95% identical thereto, or a full length complement thereof, or a functional fragment thereof. In certain embodiments, the wild type FATB1A promoter sequence can comprise the wild type "Forrest" FATB1A promoter sequence (SEQ ID NO: 21), or a sequence at least 95% identical thereto, or a full-length complement thereof, or a functional fragment thereof.

The polynucleotide encoding a polypeptide having FAT activity may comprise any wild type FATB1A genomic or coding sequence, or a sequence at least 95% identical thereto, or a full length complement thereof, or a functional fragment thereof. In certain embodiments, the wild type FATB1A genomic sequence may comprise the wild type "Forrest" FATB1A genomic sequence (SEQ ID NO: 22), or a sequence at least 95% identical thereto, or a full-length complement thereof, or a functional fragment thereof. In certain embodiments, the wild type FATB1A coding sequence may comprise the wild type "Forrest" FATB1A coding sequence (SEQ ID NO: 23), or a sequence at least 95% identical thereto, or a full-length complement thereof, or a functional fragment thereof, and may further comprise one or more mutations of the wild type "Forrest" FATB1A coding sequence selected from the group consisting of: C52T, G382A, G539A, G668A, G850A, and G1111A.

The polypeptide having FAT activity may comprise the wild type "Forrest" FATB1A amino acid sequence (SEQ ID NO: 24), or a sequence at least 95% identical thereto, or a full-length complement thereof, or a functional fragment thereof, and may further comprise one or more mutations of the wild type "Forrest" FATB1A amino acid sequence selected from the group consisting of: P18L, G128R, G180D, G223E, D284N, and A371T.

The polynucleotide encoding a FAT related promoter may comprise any wild type FATB1B promoter sequence, or a sequence at least 95% identical thereto, or a full length complement thereof, or a functional fragment thereof. In certain embodiments, the wild type FATB1B promoter sequence can comprise the wild type "Forrest" FATB1B promoter sequence (SEQ ID NO: 25), or a sequence at least 95% identical thereto, or a full-length complement thereof, or a functional fragment thereof.

The polynucleotide encoding a polypeptide having FAT activity may comprise any wild type FATB1B genomic or coding sequence, or a sequence at least 95% identical thereto, or a full length complement thereof, or a functional fragment thereof. In certain embodiments, the wild type FATB1B genomic sequence may comprise the wild type "Forrest" FATB1B genomic sequence (SEQ ID NO: 26), or a sequence at least 95% identical thereto, or a full-length complement thereof, or a functional fragment thereof. In certain embodiments, the wild type FATB1B coding sequence may comprise the wild type "Forrest" FATB1B coding sequence (SEQ ID NO: 27), or a sequence at least 95% identical thereto, or a full-length complement thereof, or a functional fragment thereof, and may further comprise one or more mutations of the wild type "Forrest" FATB1B coding sequence selected from the group consisting of: C352T, T380*, G383A, G520A, and G1043A.

The polypeptide having FAT activity may comprise the wild type "Forrest" FATB1B amino acid sequence (SEQ ID NO: 28), or a sequence at least 95% identical thereto, or a full-length complement thereof, or a functional fragment thereof, and may further comprise one or more mutations of the wild type "Forrest" FATB1B amino acid sequence selected from the group consisting of: P118S, I127X, G128E, A174T, and R348K.

The polynucleotide encoding a FAT related promoter may comprise any wild type FATB2A promoter sequence, or a sequence at least 95% identical thereto, or a full length complement thereof, or a functional fragment thereof. In certain embodiments, the wild type FATB2A promoter sequence can comprise the wild type "Forrest" FATB2A promoter sequence (SEQ ID NO: 29), or a sequence at least 95% identical thereto, or a full-length complement thereof, or a functional fragment thereof.

The polynucleotide encoding a polypeptide having FAT activity may comprise any wild type FATB2A genomic or coding sequence, or a sequence at least 95% identical thereto, or a full length complement thereof, or a functional fragment thereof. In certain embodiments, the wild type FATB2A genomic sequence may comprise the wild type "Forrest" FATB2A genomic sequence (SEQ ID NO: 30), or a sequence at least 95% identical thereto, or a full-length complement thereof, or a functional fragment thereof. In certain embodiments, the wild type FATB2A coding sequence may comprise the wild type "Forrest" FATB2A coding sequence (SEQ ID NO: 31), or a sequence at least 95% identical thereto, or a full-length complement thereof, or a functional fragment thereof, and may further comprise one or more mutations of the wild type "Forrest" FATB2A coding sequence selected from the group consisting of: C47T, G1117A, G1154A, and G1184A.

The polypeptide having FAT activity may comprise the wild type "Forrest" FATB2A amino acid sequence (SEQ ID NO: 32), or a sequence at least 95% identical thereto, or a full-length complement thereof, or a functional fragment thereof, and may further comprise one or more mutations of the wild type "Forrest" FATB2A amino acid sequence selected from the group consisting of: P16L, A373T, R385Q, and G395D.

The polynucleotide encoding a FAT related promoter may comprise any wild type FATB2B promoter sequence, or a sequence at least 95% identical thereto, or a full length complement thereof, or a functional fragment thereof. In certain embodiments, the wild type FATB2B promoter sequence can comprise the wild type "Forrest" FATB2B promoter sequence (SEQ ID NO: 33), or a sequence at least 95% identical thereto, or a full-length complement thereof, or a functional fragment thereof.

The polynucleotide encoding a polypeptide having FAT activity may comprise any wild type FATB2B genomic or coding sequence, or a sequence at least 95% identical thereto, or a full length complement thereof, or a functional fragment thereof. In certain embodiments, the wild type FATB2B genomic sequence may comprise the wild type "Forrest" FATB2B genomic sequence (SEQ ID NO: 34), or a sequence at least 95% identical thereto, or a full-length complement thereof, or a functional fragment thereof. In certain embodiments, the wild type FATB2B coding sequence may comprise the wild type "Forrest" FATB2B coding sequence (SEQ ID NO: 35), or a sequence at least 95% identical thereto, or a full-length complement thereof, or a functional fragment thereof, and may further comprise one or more mutations of the wild type "Forrest" FATB2B coding sequence selected from the group consisting of: G136A, G763A, and C988T.

The polypeptide having FAT activity may comprise the wild type "Forrest" FATB2B amino acid sequence (SEQ ID NO: 36), or a sequence at least 95% identical thereto, or a full-length complement thereof, or a functional fragment thereof, and may further comprise one or more mutations of the wild type "Forrest" FATB2B amino acid sequence selected from the group consisting of: G46S, V255M, and Q330*.

The method of increasing oleic acid content of a soybean plant may comprise transforming the soybean plant with more than one polynucleotide encoding a FAT related promoter that functions in the soybean plant, provided that each polynucleotide encoding a FAT related promoter that functions in the soybean plant is operably linked to a polynucleotide encoding a polypeptide having FAT activity.

The more than one polynucleotide encoding a FAT related promoter may be selected from the group consisting of: (i) any wild type FATA1A promoter sequence, or a sequence at least 95% identical thereto, or a full length complement thereof, or a functional fragment thereof, wherein the polypeptide having FAT activity comprises the wild type "Forrest" FATA1A amino acid sequence (SEQ ID NO: 20), or a sequence at least 95% identical thereto, or a full-length complement thereof, or a functional fragment thereof, and further comprises one or more mutations of the wild type "Forrest" FATA1A amino acid sequence (SEQ ID NO: 20) selected from the group consisting of: S37F, A55T, T146I, A231V, G277E, and V310I; (ii) any wild type FATB1A promoter sequence, or a sequence at least 95% identical thereto, or a full length complement thereof, or a functional fragment thereof, wherein the polypeptide having FAT activity comprises the wild type "Forrest" FATB1A amino acid sequence (SEQ ID NO: 24), or a sequence at least 95% identical thereto, or a full-length complement thereof, or a functional fragment thereof, and further comprises one or more mutations of the wild type "Forrest" FATB1A amino acid sequence (SEQ ID NO: 24) selected from the group consisting of: P18L, G128R, G180D, G223E, D284N, and A371T; (iii) any wild type FATB1B promoter sequence, or a sequence at least 95% identical thereto, or a full length complement thereof, or a functional fragment thereof, wherein the polypeptide having FAT activity comprises the wild type "Forrest" FATB1B amino acid sequence (SEQ ID NO: 28), or a sequence at least 95% identical thereto, or a full-length complement thereof, or a functional fragment thereof, and further comprises one or more mutations of the wild type "Forrest" FATB1B amino acid sequence (SEQ ID NO: 28) selected from the group consisting of: P118S, I127X, G128E, A174T, and R348K; (iv) any wild type FATB2A promoter sequence, or a sequence at least 95% identical thereto, or a full length complement thereof, or a functional fragment thereof, wherein the polypeptide having FAT activity comprises the wild type "Forrest" FATB2A amino acid sequence (SEQ ID NO: 32), or a sequence at least 95% identical thereto, or a full-length complement thereof, or a functional fragment thereof, and further comprises one or more mutations of the wild type "Forrest" FATB2A amino acid sequence (SEQ ID NO: 32) selected from the group consisting of: P16L, A373T, R385Q, and G395D; and (v) any wild type FATB2B promoter sequence, or a sequence at least 95% identical thereto, or a full length complement thereof, or a functional fragment thereof, wherein the polypeptide having FAT activity comprises the wild type "Forrest" FATB2B amino acid sequence (SEQ ID NO: 36), or a sequence at least 95% identical thereto, or a full-length complement thereof, or a functional fragment thereof, and further comprises one or more mutations of the wild type "Forrest" FATB2B amino acid sequence (SEQ ID NO: 36) selected from the group consisting of: G46S, V255M, and Q330*.

The transformed soybean plant may have increased oleic acid content as compared to a control soybean plant lacking the polynucleotide encoding a polypeptide having FAT activity as described above. The increased oleic acid content may comprise an at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, at least about 60%, at least about 70%, at least about 80%, at least about 90%, or at least about 100% increase in oleic acid content as compared to a control soybean plant lacking the polynucleotide encoding a polypeptide having FAT activity as described above.

DNA Constructs

Another embodiment of the present invention is a DNA construct comprising a polynucleotide encoding a fatty acid thioesterase (FAT) related promoter that functions in a soybean plant operably linked to a polynucleotide encoding a polypeptide having FAT activity.

The polynucleotide encoding a FAT related promoter may comprise any wild type FAT promoter sequence, or a sequence at least 95% identical thereto, or a full length complement thereof, or a functional fragment thereof. In certain embodiments, the wild type FAT promoter sequence can be selected from the group consisting of a promoter sequence of FATA1A, FATA1B, FATB1A, FATB2A, FATB3A, FATB4A, FATB5A, FATB1B, FATB2B, FATB3B, FATB4B, and FATB5B. In certain embodiments, the wild type FAT promoter sequence can be selected from the group consisting of a promoter sequence of FATA1A, FATB1A, FATB1B, FATB2A, and FATB2B.

In some embodiments, the polynucleotide encoding a polypeptide having FAT activity may comprise any wild type FAT genomic or coding sequence, or a sequence at least 95% identical thereto, or a full length complement thereof, or a functional fragment thereof. In one embodiment, the wild type FAT genomic or coding sequence can be selected from the group consisting of a genomic or coding sequence of FATA1A, FATA1B, FATB1A, FATB2A, FATB3A, FATB4A, FATB5A, FATB1B, FATB2B, FATB3B, FATB4B, and FATB5B. In certain embodiments, the wild type FAT genomic or coding sequence can be selected from the group consisting of a genomic or coding sequence of FATA1A, FATB1A, FATB1B, FATB2A, and FATB2B.

The polypeptide having FAT activity may comprise any wild type FAT amino acid sequence, or a sequence at least 95% identical thereto, or a full-length complement thereof, or a functional fragment thereof. In one embodiment, the wild type FAT amino acid sequence can be selected from the group consisting of an amino acid sequence of FATA1A, FATA1B, FATB1A, FATB2A, FATB3A, FATB4A, FATB5A, FATB1B, FATB2B, FATB3B, FATB4B, and FATB5B. In certain embodiments, the wild type FAT amino acid sequence can be selected from the group consisting of an amino acid sequence of FATA1A, FATB1A, FATB1B, FATB2A, and FATB2B.

The polynucleotide encoding a FAT related promoter may comprise any wild type FATA1A promoter sequence, or a sequence at least 95% identical thereto, or a full length complement thereof, or a functional fragment thereof. In certain embodiments, the wild type FATA1A promoter sequence can comprise the wild type "Forrest" FATA1A promoter sequence (SEQ ID NO: 17), or a sequence at least 95% identical thereto, or a full-length complement thereof, or a functional fragment thereof.

The polynucleotide encoding a polypeptide having FAT activity may comprise any wild type FATA1A genomic or coding sequence, or a sequence at least 95% identical thereto, or a full length complement thereof, or a functional fragment thereof. In certain embodiments, the wild type FATA1A genomic sequence may comprise the wild type "Forrest" FATA1A genomic sequence (SEQ ID NO: 18), or a sequence at least 95% identical thereto, or a full-length complement thereof, or a functional fragment thereof. In certain embodiments, the wild type FATA1A coding sequence may comprise the wild type "Forrest" FATA1A coding sequence (SEQ ID NO: 19), or a sequence at least 95% identical thereto, or a full-length complement thereof, or a functional fragment thereof, and may further comprise one or more mutations of the wild type "Forrest" FATA1A coding sequence selected from the group consisting of: C110T, G163T, C437T, C692T, G830A, and G928A.

The polypeptide having FAT activity may comprise the wild type "Forrest" FATA1A amino acid sequence (SEQ ID NO: 20), or a sequence at least 95% identical thereto, or a full-length complement thereof, or a functional fragment thereof, and may further comprise one or more mutations of the wild type "Forrest" FATA1A amino acid sequence selected from the group consisting of: S37F, A55T, T146I, A231V, G277E, and V310I.

The polynucleotide encoding a FAT related promoter may comprise any wild type FATB1A promoter sequence, or a sequence at least 95% identical thereto, or a full length complement thereof, or a functional fragment thereof. In certain embodiments, the wild type FATB1A promoter sequence can comprise the wild type "Forrest" FATB1A promoter sequence (SEQ ID NO: 21), or a sequence at least 95% identical thereto, or a full-length complement thereof, or a functional fragment thereof.

The polynucleotide encoding a polypeptide having FAT activity may comprise any wild type FATB1A genomic or coding sequence, or a sequence at least 95% identical thereto, or a full length complement thereof, or a functional fragment thereof. In certain embodiments, the wild type FATB1A genomic sequence may comprise the wild type "Forrest" FATB1A genomic sequence (SEQ ID NO: 22), or a sequence at least 95% identical thereto, or a full-length complement thereof, or a functional fragment thereof. In certain embodiments, the wild type FATB1A coding sequence may comprise the wild type "Forrest" FATB1A coding sequence (SEQ ID NO: 23), or a sequence at least 95% identical thereto, or a full-length complement thereof, or a functional fragment thereof, and may further comprise one or more mutations of the wild type "Forrest" FATB1A coding sequence selected from the group consisting of: C52T, G382A, G539A, G668A, G850A, and G1111A.

The polypeptide having FAT activity may comprise the wild type "Forrest" FATB1A amino acid sequence (SEQ ID NO: 24), or a sequence at least 95% identical thereto, or a full-length complement thereof, or a functional fragment thereof, and may further comprise one or more mutations of the wild type "Forrest" FATB1A amino acid sequence selected from the group consisting of: P18L, G128R, G180D, G223E, D284N, and A371T.

The polynucleotide encoding a FAT related promoter may comprise any wild type FATB1B promoter sequence, or a sequence at least 95% identical thereto, or a full length complement thereof, or a functional fragment thereof. In certain embodiments, the wild type FATB1B promoter sequence can comprise the wild type "Forrest" FATB1B promoter sequence (SEQ ID NO: 25), or a sequence at least 95% identical thereto, or a full-length complement thereof, or a functional fragment thereof.

The polynucleotide encoding a polypeptide having FAT activity may comprise any wild type FATB1B genomic or coding sequence, or a sequence at least 95% identical thereto, or a full length complement thereof, or a functional fragment thereof. In certain embodiments, the wild type FATB1B genomic sequence may comprise the wild type "Forrest" FATB1B genomic sequence (SEQ ID NO: 26), or a sequence at least 95% identical thereto, or a full-length complement thereof, or a functional fragment thereof. In certain embodiments, the wild type FATB1B coding sequence may comprise the wild type "Forrest" FATB1B coding sequence (SEQ ID NO: 27), or a sequence at least 95% identical thereto, or a full-length complement thereof, or a functional fragment thereof, and may further comprise one or more mutations of the wild type "Forrest" FATB1B coding sequence selected from the group consisting of: C352T, T380*, G383A, G520A, and G1043A.

The polypeptide having FAT activity may comprise the wild type "Forrest" FATB1B amino acid sequence (SEQ ID NO: 28), or a sequence at least 95% identical thereto, or a full-length complement thereof, or a functional fragment thereof, and may further comprise one or more mutations of the wild type "Forrest" FATB1B amino acid sequence selected from the group consisting of: P118S, I127X, G128E, A174T, and R348K.

The polynucleotide encoding a FAT related promoter may comprise any wild type FATB2A promoter sequence, or a sequence at least 95% identical thereto, or a full length complement thereof, or a functional fragment thereof. In certain embodiments, the wild type FATB2A promoter sequence can comprise the wild type "Forrest" FATB2A promoter sequence (SEQ ID NO: 29), or a sequence at least 95% identical thereto, or a full-length complement thereof, or a functional fragment thereof.

The polynucleotide encoding a polypeptide having FAT activity may comprise any wild type FATB2A genomic or coding sequence, or a sequence at least 95% identical thereto, or a full length complement thereof, or a functional fragment thereof. In certain embodiments, the wild type FATB2A genomic sequence may comprise the wild type "Forrest" FATB2A genomic sequence (SEQ ID NO: 30), or a sequence at least 95% identical thereto, or a full-length complement thereof, or a functional fragment thereof. In certain embodiments, the wild type FATB2A coding sequence may comprise the wild type "Forrest" FATB2A coding sequence (SEQ ID NO: 31), or a sequence at least 95% identical thereto, or a full-length complement thereof, or a functional fragment thereof, and may further comprise one or more mutations of the wild type "Forrest" FATB2A coding sequence selected from the group consisting of: C47T, G1117A, G1154A, and G1184A.

The polypeptide having FAT activity may comprise the wild type "Forrest" FATB2A amino acid sequence (SEQ ID NO: 32), or a sequence at least 95% identical thereto, or a full-length complement thereof, or a functional fragment thereof, and may further comprise one or more mutations of the wild type "Forrest" FATB2A amino acid sequence selected from the group consisting of: P16L, A373T, R385Q, and G395D.

The polynucleotide encoding a FAT related promoter may comprise any wild type FATB2B promoter sequence, or a sequence at least 95% identical thereto, or a full length complement thereof, or a functional fragment thereof. In certain embodiments, the wild type FATB2B promoter sequence can comprise the wild type "Forrest" FATB2B promoter sequence (SEQ ID NO: 33), or a sequence at least 95% identical thereto, or a full-length complement thereof, or a functional fragment thereof.

The polynucleotide encoding a polypeptide having FAT activity may comprise any wild type FATB2B genomic or coding sequence, or a sequence at least 95% identical thereto, or a full length complement thereof, or a functional fragment thereof. In certain embodiments, the wild type FATB2B genomic sequence may comprise the wild type "Forrest" FATB2B genomic sequence (SEQ ID NO: 34), or a sequence at least 95% identical thereto, or a full-length complement thereof, or a functional fragment thereof. In certain embodiments, the wild type FATB2B coding sequence may comprise the wild type "Forrest" FATB2B coding sequence (SEQ ID NO: 35), or a sequence at least 95% identical thereto, or a full-length complement thereof, or a functional fragment thereof, and may further comprise one or more mutations of the wild type "Forrest" FATB2B coding sequence selected from the group consisting of: G136A, G763A, and C988T.

The polypeptide having FAT activity may comprise the wild type "Forrest" FATB2B amino acid sequence (SEQ ID NO: 36), or a sequence at least 95% identical thereto, or a full-length complement thereof, or a functional fragment thereof, and may further comprise one or more mutations of the wild type "Forrest" FATB2B amino acid sequence selected from the group consisting of: G46S, V255M, and Q330*.

The DNA construct may comprise more than one polynucleotide encoding a FAT related promoter that functions in a soybean plant, provided that each polynucleotide encoding a FAT related promoter that functions in a soybean plant is operably linked to a polynucleotide encoding a polypeptide having FAT activity.

The more than one polynucleotide encoding a FAT related promoter may be selected from the group consisting of: (i) any wild type FATA1A promoter sequence, or a sequence at least 95% identical thereto, or a full length complement thereof, or a functional fragment thereof, wherein the polypeptide having FAT activity comprises the wild type "Forrest" FATA1A amino acid sequence (SEQ ID NO: 20), or a sequence at least 95% identical thereto, or a full-length complement thereof, or a functional fragment thereof, and further comprises one or more mutations of the wild type "Forrest" FATA1A amino acid sequence (SEQ ID NO: 20)

selected from the group consisting of: S37F, A55T, T146I, A231V, G277E, and V310I; (ii) any wild type FATB1A promoter sequence, or a sequence at least 95% identical thereto, or a full length complement thereof, or a functional fragment thereof, wherein the polypeptide having FAT activity comprises the wild type "Forrest" FATB1A amino acid sequence (SEQ ID NO: 24), or a sequence at least 95% identical thereto, or a full-length complement thereof, or a functional fragment thereof, and further comprises one or more mutations of the wild type "Forrest" FATB1A amino acid sequence (SEQ ID NO: 24) selected from the group consisting of: P18L, G128R, G180D, G223E, D284N, and A371T; (iii) any wild type FATB1B promoter sequence, or a sequence at least 95% identical thereto, or a full length complement thereof, or a functional fragment thereof, wherein the polypeptide having FAT activity comprises the wild type "Forrest" FATB1B amino acid sequence (SEQ ID NO: 28), or a sequence at least 95% identical thereto, or a full-length complement thereof, or a functional fragment thereof, and further comprises one or more mutations of the wild type "Forrest" FATB1B amino acid sequence (SEQ ID NO: 28) selected from the group consisting of: P118S, I127X, G128E, A174T, and R348K; (iv) any wild type FATB2A promoter sequence, or a sequence at least 95% identical thereto, or a full length complement thereof, or a functional fragment thereof, wherein the polypeptide having FAT activity comprises the wild type "Forrest" FATB2A amino acid sequence (SEQ ID NO: 32), or a sequence at least 95% identical thereto, or a full-length complement thereof, or a functional fragment thereof, and further comprises one or more mutations of the wild type "Forrest" FATB2A amino acid sequence (SEQ ID NO: 32) selected from the group consisting of: P16L, A373T, R385Q, and G395D; and (v) any wild type FATB2B promoter sequence, or a sequence at least 95% identical thereto, or a full length complement thereof, or a functional fragment thereof, wherein the polypeptide having FAT activity comprises the wild type "Forrest" FATB2B amino acid sequence (SEQ ID NO: 36), or a sequence at least 95% identical thereto, or a full-length complement thereof, or a functional fragment thereof, and further comprises one or more mutations of the wild type "Forrest" FATB2B amino acid sequence (SEQ ID NO: 36) selected from the group consisting of: G46S, V255M, and Q330*.

Additional Mutations

The polynucleotide encoding a FAT related promoter may comprise any wild type FATA1B promoter sequence, or a sequence at least 95% identical thereto, or a full length complement thereof, or a functional fragment thereof. The polypeptide having FAT activity may comprise the wild type "Forrest" FATA1B sequence, or a sequence at least 95% identical thereto, or a full-length complement thereof, or a functional fragment thereof, and may further comprise one or more mutations of the wild type "Forrest" FATA1B sequence.

The polynucleotide encoding a FAT related promoter may comprise any wild type FATB3A promoter sequence, or a sequence at least 95% identical thereto, or a full length complement thereof, or a functional fragment thereof. The polypeptide having FAT activity may comprise the wild type "Forrest" FATB3A sequence, or a sequence at least 95% identical thereto, or a full-length complement thereof, or a functional fragment thereof, and may further comprise one or more mutations of the wild type "Forrest" FATB3A sequence.

The polynucleotide encoding a FAT related promoter may comprise any wild type FATB3B promoter sequence, or a sequence at least 95% identical thereto, or a full length complement thereof, or a functional fragment thereof. The polypeptide having FAT activity may comprise the wild type "Forrest" FATB3B sequence, or a sequence at least 95% identical thereto, or a full-length complement thereof, or a functional fragment thereof, and may further comprise one or more mutations of the wild type "Forrest" FATB3B sequence.

The polynucleotide encoding a FAT related promoter may comprise any wild type FATB4A promoter sequence, or a sequence at least 95% identical thereto, or a full length complement thereof, or a functional fragment thereof. The polypeptide having FAT activity may comprise the wild type "Forrest" FATB4A sequence, or a sequence at least 95% identical thereto, or a full-length complement thereof, or a functional fragment thereof, and may further comprise one or more mutations of the wild type "Forrest" FATB4A sequence.

The polynucleotide encoding a FAT related promoter may comprise any wild type FATB4B promoter sequence, or a sequence at least 95% identical thereto, or a full length complement thereof, or a functional fragment thereof. The polypeptide having FAT activity may comprise the wild type "Forrest" FATB4B sequence, or a sequence at least 95% identical thereto, or a full-length complement thereof, or a functional fragment thereof, and may further comprise one or more mutations of the wild type "Forrest" FATB4B sequence.

The polynucleotide encoding a FAT related promoter may comprise any wild type FATB5A promoter sequence, or a sequence at least 95% identical thereto, or a full length complement thereof, or a functional fragment thereof. The polypeptide having FAT activity may comprise the wild type "Forrest" FATB5A sequence, or a sequence at least 95% identical thereto, or a full-length complement thereof, or a functional fragment thereof, and may further comprise one or more mutations of the wild type "Forrest" FATB5A sequence.

The polynucleotide encoding a FAT related promoter may comprise any wild type FATB5B promoter sequence, or a sequence at least 95% identical thereto, or a full length complement thereof, or a functional fragment thereof. The polypeptide having FAT activity may comprise the wild type "Forrest" FATB5B sequence, or a sequence at least 95% identical thereto, or a full-length complement thereof, or a functional fragment thereof, and may further comprise one or more mutations of the wild type "Forrest" FATB5B.

The additional polypeptides having FAT activity described in this embodiment section may be incorporated into the present invention in the same manner as the polypeptides having FAT activity discussed in the other embodiments described in the above sections, and may be combined with those other embodiments.

Sequences and Mutations

The amino acid sequences and nucleic acid sequences described herein may contain various mutations. Mutations may include insertions, substitutions, and deletions. Insertions are written as follows: (+)(amino acid/nucleic acid sequence position number)(inserted amino acid/nucleic acid base). For example, +287A would mean an insertion of an alanine residue after position 287 in the corresponding amino acid sequence. Substitutions are written as follows: (amino acid/nucleic acid base to be replaced)(amino acid/nucleic acid sequence position number)(substituted amino acid/nucleic acid base). For example, C1082A would mean a substitution of an adenine base instead of a cytosine base at position 1082 in the corresponding nucleic acid sequence.

Deletions are written as follows: (amino acid/nucleic acid base to be deleted)(amino acid/nucleic acid sequence position number)(-). For example, C970—would mean a deletion of the cytosine base normally located at position 970 in the corresponding nucleic acid sequence. "*" can also be used to indicate a deletion or premature stop.

The amino acid sequences and nucleic acid sequences described herein may contain mutations at various sequence positions. Sequence positions may be written a variety of ways for convenience. More specifically, sequence positions may be written from either the beginning of the sequence as a positive position number, or from the end of the sequence as a negative number. Sequence positions may be converted easily between a positive notation and a negative notation by comparing to the sequence length and either adding or subtracting the sequence length. For example, a promoter containing 10 nucleic acid bases with a mutation from cytosine to adenine at the second position from the start of the sequence may be written as C2A. Alternatively, this mutation may be written as C(-9)A, -9C/A, or in a similar fashion denoting the negative position number.

Definitions and Alternate Embodiments

The following definitions and methods are provided to better define the present invention and to guide those of ordinary skill in the art in the practice of the present invention. Unless otherwise noted, terms are to be understood according to conventional usage by those of ordinary skill in the relevant art.

The term "agronomically elite" refers to a genotype that has a culmination of many distinguishable traits such as emergence, vigor, vegetative vigor, disease resistance, seed set, standability, and threshability, which allows a producer to harvest a product of commercial significance.

An "allele" refers to one of two or more alternative forms of a genomic sequence at a given locus on a chromosome.

The term "chimeric" is understood to refer to the product of the fusion of portions of two or more different polynucleotide molecules. "Chimeric promoter" is understood to refer to a promoter produced through the manipulation of known promoters or other polynucleotide molecules. Such chimeric promoters can combine enhancer domains that can confer or modulate gene expression from one or more promoters or regulatory elements, for example, by fusing a heterologous enhancer domain from a first promoter to a second promoter with its own partial or complete regulatory elements. Thus, the design, construction, and use of chimeric promoters according to the methods disclosed herein for modulating the expression of operably linked polynucleotide sequences are encompassed by the present invention.

Novel chimeric promoters can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A construct of the present invention can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule, which can play an important role in translation initiation and can also be a genetic component in an expression construct. These additional upstream and downstream regulatory nucleic acid molecules may be derived from a source that is native or heterologous with respect to the other elements present on the promoter construct.

"Expression vector", "vector", "expression construct", "vector construct", "plasmid", or "recombinant DNA construct" is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

The term "genotype" means the specific allelic makeup of a plant.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m = 81.5°$ C. $+ 16.6(\log_{10}[Na^{+1}]) + 0.41$ (fraction G/C content) $- 0.63$ (% formamide) $- (600/l)$. Furthermore, the $T_m$ of a DNA:DNA hybrid is decreased by 1-1.5° C. for every 1% decrease in nucleotide identity.

The term "introgressed," when used in reference to a genetic locus, refers to a genetic locus that has been introduced into a new genetic background. Introgression of a genetic locus can thus be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

The term "linked," when used in the context of nucleic acid markers and/or genomic regions, means that the markers and/or genomic regions are located on the same linkage group or chromosome.

A "marker" means a detectable characteristic that can be used to discriminate between organisms. Examples of such characteristics include, but are not limited to, genetic markers, biochemical markers, metabolites, morphological characteristics, and agronomic characteristics.

A "marker gene" refers to any transcribable nucleic acid molecule whose expression can be screened for or scored in some way.

Certain genetic markers useful in the present invention include "dominant" or "codominant" markers. "Codominant" markers reveal the presence of two or more alleles (two per diploid individual). "Dominant" markers reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

The term "phenotype" means the detectable characteristics of a cell or organism that can be influenced by gene expression.

The term "plant" can include plant cells, plant protoplasts, plant cells of tissue culture from which a plant can be regenerated, plant calli, plant clumps and plant cells that are intact in plants or parts of plants such as pollen, flowers, seeds, leaves, stems, and the like. Each of these terms can apply to a soybean "plant". Plant parts (e.g., soybean parts) include, but are not limited to, pollen, an ovule and a cell.

The term "population" means a genetically heterogeneous collection of plants that share a common parental derivation.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the transcription start site, such as, in the case of a polymerase II type promoter, a TATA element. A promoter can optionally include distal enhancer or repressor elements, which can be located as much as several thousand base pairs from the start site of transcription.

A "quantitative trait locus (QTL)" is a chromosomal location that encodes for alleles that affect the expressivity of a phenotype.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells may be used.

The "transcription start site" or "initiation site" is the position surrounding a nucleotide that is part of the transcribed sequence, which is also defined as position+1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) can be denominated as negative.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a plant into which a heterologous nucleic acid molecule has been introduced. The nucleic acid molecule can be stably integrated into the genome as generally known in the art. Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

The terms "variety" and "cultivar" mean a group of similar plants that by their genetic pedigrees and performance can be identified from other varieties within the same species.

"Wild-type" refers to a virus or organism found in nature without any known mutation.

In some embodiments, numbers expressing quantities of ingredients, properties such as molecular weight, reaction conditions, and so forth, used to describe and claim certain embodiments of the present invention are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present invention are approximations, the numerical values set forth in the specific examples are reported as precisely as practicable. The numerical values presented in some embodiments of the present invention may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

In some embodiments, the terms "a" and "an" and "the" and similar references used in the context of describing a particular embodiment (especially in the context of certain of the following claims) can be construed to cover both the singular and the plural, unless specifically noted otherwise. When used in conjunction with the word "comprising" or other open language in the claims, the words "a" and "an" denote "one or more," unless specifically noted.

In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present invention and does not pose a limitation on the scope of the present invention otherwise claimed. No language in the specification should be construed as indicating any non-claimed element essential to the practice of the present invention.

Groupings of alternative elements or embodiments of the present invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the present invention in detail, it will be apparent that all of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the present invention, and this can be considered to constitute examples of modes for its practice. However, those of skill in the art should, in light of the present disclosure, appreciate that many changes can be made in the specific embodiments that are disclosed and still obtain a like or similar result without departing from the spirit and scope of the present invention.

Example 1. Identification of FATA and FATB from Soybean and Other Plant Species

The putative soybean acyl-ACP thioesterase genes were identified by BLASTP searches against soybean reference genome (*Glycine max*, Wm82.a2.v1) at Phytozome (v12.1) using *Arbidopisis thaliana* acyl-ACP thioesterase protein sequences as queries (https://phytozome.jgi.doe.gov). Using the same approach, the putative acyl-ACP thioesterases were identified from reference genome of *Phaseolus vulgaris* (v2.1), *Medicago truncatula* (Mt4.0v1), *Brassica rapa* FPsc (v1.3), *Oryza sativa* (v7 JGI), *Lotus japonicas* genome assembly build 3.0 (http://www.kazusa.or.jp/lotus/), *Elaeis guineensis* assembly EG5 (https://www.ncbi.nlm.nih.gov/genome/2669), and *Cocos nucifera* assembly ASM812446v1 (https://www.ncbi.nlm.nih.gov/genome/?term=Cocos+nucifera). The total of 50 identified protein sequences with accession numbers are included herein.

Example 2. Phylogenetic Analysis

Multiple sequence alignments of the full-length acyl-ACP thioesterase protein sequences from nine plant species were performed by MUltiple Sequence Comparison by Log-Expectation (MUSCLE). An unrooted phylogenetic tree was then constructed by maximum likelihood (ML) method in MEGA X using Jones-Taylor-Thornton Gamma Distributed (JTT+G) model for all FAT genes and JTT+G+I model with Invariant Sites (I) for soybean FAT genes.

Example 3. Gene Structure, Expression Profiling and Conserved Domain Analysis

The genomic and coding sequences of soybean acyl-ACP thioesterase genes retrieved from Phytozome v12.1 were aligned to generate the gene exon-intron structure diagram using the Gene Structure Display Server. To analyze the tissue-specific expression of soybean acyl-ACP thioesterase genes, normalized transcript data in six different tissues were downloaded from Soybase (https://www.soybase.org/soyseq/). The expressions profiling was visualized through heatmap using Heatmapper. Followed by multiple sequence alignment between FATA and FATB in soybean and *A. thaliana*, the residues for substrate specifying have been proposed based on previously described criteria. Catalytic residues in conserved motifs of soybean acyl-ACP thioesterases were identified from NCBI Conserved Domain Database (CDD) (https://www.ncbi.nlm.nih.gov/cdd).

Example 4. Chromosomal Localization and Syntenic Analysis

The locations of soybean acyl-ACP thioesterase genes and their corresponding chromosomes were drawn based on soybean genome annotation a2.v1 on SoyBase. Syntenic analysis were performed using soybean acyl-ACP thioesterase genes as locus identifier in plant genome duplication database (PGDD). Nonsynonymous (Ka) versus synonymous substitution (Ks) rates were calculated based on their values retrieved from PGDD. For gene pairs whose information are not available at PGDD, PAL2NAL program was used to estimated Ka and Ks. Given the Ks values and a rate of $6.1 \times 10^{-9}$ substitutions per site per year, the divergence time (T) was equal to $Ks/(2 \; 6.1 \times 10^{-9}) \times 10-6$ Mya for each gene pair.

Example 5. Development of EMS Mutagenized Soybean Populations

EMS mutagenesis was performed as previously described in Meksem K, et al. TILLING: a reverse genetics and a functional genomics tool in soybean. The handbook of plant functional genomics: Concepts and protocols, (2008), pgs. 251-265. The soybean cv. Forrest and PI88788 seeds were used to generate M2 population in the greenhouse at SIUC Horticulture Research Center (HRC). A total of 4,032 M2 lines were advanced to M3 generations by single-seed descent in the field between 2012-2015. M3 seeds from each mutant line were harvested, thrashed, and stored at −20° C.

Example 6. Mutation Detection and Validation

The mutations in five soybean acyl-ACP thioesterase genes were detected using TILLING by Targeted Capture Sequencing (TbyTCS) method. A subset of mutations at GmFATA1A, GmFATB1A and GmFATB1B were confirmed by Sanger sequencing. PCR primers were designed to amplify the fragments covering the exons of three soybean acyl-ACP thioesterase genes using Primer3. The PCR program was set up with 30 cycles of amplification at 94° C. for 30s, 52° C. for 30s, and 72° C. for 1 min. The PCR products were then purified using QIAquick$^R$ Gel Extraction Kit (QIAGEN, Valencia, CA, USA). The purified samples were sent for sequencing at GENEWIZ (https://www.genewiz.com/). The putative mutations were identified by alignment sampled sequences to reference using Unipro UGENE.

Example 7. Fatty Acid Analysis of Seeds from GmFAT Mutants

Five major fatty acids content were measured from selected M2/M3 lines, according to the two-step methylation procedure. At least three seeds per line were crushed in 16 mm×200 mm tube with Teflon-lined screw cap individually. 2 mL sodium methoxide was added into tube followed by 50° C. incubation for 10 min. After cooling 5 min, the samples were mixed with 3 mL of 5% (v/v) methanolic HCl, incubated at 80° C. for 10 min, and cooled for 7 min. Each tube was then added with 7.5 mL of 6% (w/v) potassium carbonate and 1 mL of hexane and centrifuged at 1,200 g for 5 min. The upper layer was transferred to vials, from which the individual fatty acid content was determined as a percentage of the total fatty acids of soybean seed by gas chromatography. A Shimadzu GC-2010 (Columbia, MD) gas chromatograph fitted with a flame ionization detector was equipped with a Supelco 60-m SP-2560 fused silica capillary famewax column (0.25 mm i.d.×0.25 µm film thickness). The standard fatty acids were run first to create calibration reference.

Example 8. Identification of Plant Acyl-ACP Thioesterase Gene Family Members in Soybean Four FATB genes have previously been identified in soybean, from which GmFATB1A is associated with reducing palmitic acid content. To identify the putative members of TE family in soybean, a BLASTP search against the soybean genome database (Wm82.a2.v1) was performed by using *A. thaliana* TE protein sequences as queries. Combined with soybean TEs from Family TE14 in the ThYme database, a total of 12 TEs have been found in soybean genome, including ten GmFATB and two GmFATA. Based on nomenclature proposed previously, additional six GmFATB genes are denominated as GmFATB3A (Glyma.04G197400), GmFATB3B (Glyma.06G168100), GmFATB4A (Glyma.04G197500), GmFATB4B (Glyma06g17625), GmFATB5A (Glyma.10G268200), GmFATB5B (Glyma.20G122900) as well as two GmFATA genes, GmFATA1A (Glyma.18G167300) and GmFATA1B (Glyma.08G349200) (TABLE 1).

four times more than in *Arabidopsis* and doubled over the number of TEs in common bean, palm, and rice. Compared

TABLE 1

The list of soybean acyl-ACP thioesterase genes with their corresponding gene ID, nucleotide sequence characteristics, and protein sequence properties.

| Gene name | Gene ID | Gene length (bp) | CDS (bp) | Exons | Protein sequence (aa) | Mol.Wt. (kDa) | pI |
|---|---|---|---|---|---|---|---|
| FATB1A | Glyma.05G012300 | 4195 | 1251 | 6 | 416 | 45.9 | 6.48 |
| FATB1B | Glyma.17G120400 | 4382 | 1251 | 6 | 416 | 46.0 | 6.28 |
| FATB2A | Glyma.04G151600 | 7394 | 1269 | 6 | 422 | 46.1 | 8.12 |
| FATB2B | Glyma.06G211300 | 4959 | 1260 | 6 | 419 | 46.3 | 7.08 |
| FATB3A | Glyma.04G197400 | 2627 | 1149 | 6 | 382 | 43.9 | 9.30 |
| FATB3B | Glyma.06G168100 | 3108 | 1152 | 6 | 383 | 44.0 | 8.91 |
| FATB4A | Glyma.04G197500 | 3391 | 1158 | 6 | 385 | 44.8 | 9.27 |
| FATB4B | Glyma.06G168000 | 3838 | 1140 | 6 | 379 | 43.9 | 8.89 |
| FATB5A | Glyma.10G268200 | 2701 | 1203 | 6 | 400 | 45.6 | 8.41 |
| FATB5B | Glyma.20G122900 | 3197 | 1200 | 6 | 399 | 45.4 | 8.13 |
| FATA1A | Glyma.18G167300 | 6650 | 1125 | 7 | 374 | 42.0 | 8.11 |
| FATA1B | Glyma.08G349200 | 5070 | 1155 | 8 | 384 | 43.3 | 8.86 |

Amino acid sequence alignment has shown that two genes in each subfamily of GmFATB and GmFATA shared a highly identity, such as GmFATB1A/FmFATB1B (96%), GmFATB3A/GmFATB3B (94%), and GmFATA1A/ GmFATA1B (93%). The coding DNA sequence (CDS) lengths of the GmFATB ranged from 1140 bp to 1269 bp with an average of 1203 bp while that of GmFATA averaged 1140 bp. The sizes and predicted molecular weight of GmFATB1 and GmFATB2 subfamilies are larger than 400 amino acids and 45.8 kDa, respectively. GmFATB1A, GmFATB1B, and GmFATB2B, showed acidic isoelectric point (pI) values whereas the rest of soybean TEs presented basic pI values (TABLE 1).

Example 9. Phylogenetic Analysis of Plant Acyl-ACP Thioesterase Gene Family

13 FATA and 25 FATB proteins from other three legumes, two dicot species, and three monocot species have been identified through BLAST searches using *A. thaliana* TE protein sequences. A maximum likelihood (ML) tree was construct with 50 protein sequences to elucidate the phylogenetic relationships among TEs from nine plant species (FIG. 1). As expected, two distinct clusters were formed to separate 15 FATA members from 35 FATB ones. In FATB cluster, all 35 FATB members could be classified into four subgroups. In subgroup I, GmFATB1A, GmFATB1B, GmFATB2A and GmFATB2B were grouped together with AtFATB, BrFATB and eight FATB members from other three legume species. Subgroup II contains all FATB members from three monocot species except one OsFATB. There are seven FATB members in subgroup III, including GmFATB3A, GmFATB3B, GmFATB4A and GmFATB4B. And subgroup IV has GmFATB5A, GmFATB5B, and 3 FATB members from two legumes and one monocot species (FIG. 1). On the other hand, FATA members from all legume species were clustered apart from ones in monocot species. However, AtFATA were grouped with BrFATA in two different branches. The phylogenetic analysis also showed a close evolutionary relationship within each of six soybean TEs gene pairs with >88% reliability (FIG. 1).

Figure 2:
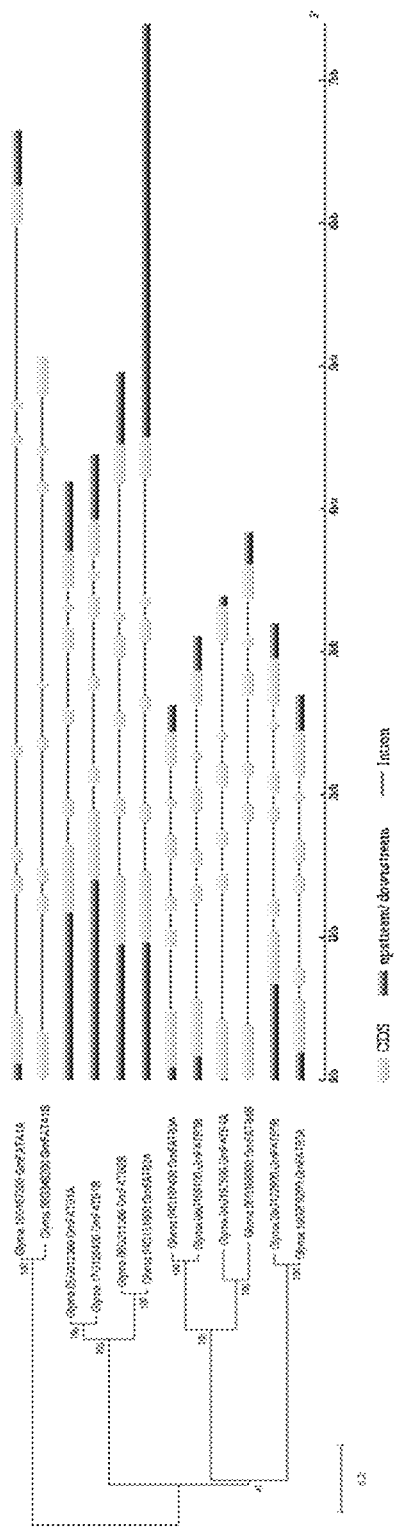
FIG. 2 is a schematic showing the phylogenetic relationships and gene structures of GmFATA and GmFATB. The protein sequences of all soybean acyl-ACP thioesterases were subjected to a MUSCLE alignment and phylogenetic tree was constructed using Mega X. The structures of 12 soybean acyl-ACP thioesterase genes were plotted with yellow boxes representing exons (coding DNA sequence, CDS), black lines illustrating introns, and blue boxes indicating 5'-UTR and 3'-UTR regions. The size of gene structures could be measured by the scale in the unit of base pair (bp) at the bottom. The gene structure was drawn using the Gene Structure Display Server.

Example 10. Gene Structure and Expression Profiling of Soybean Acyl-ACP Thioesterase Genes Given the two whole-genome duplication events, the soybean TE gene family consisted of 12 members, which is to an average of 5860 bp for GmFATA, the gene lengths of GmFATB1 and GmFATB2 subfamilies are more than 4195 bp while that of GmFATB3, GmFATB4, and GmFATB5 subfamilies are 3143 bp on average (TABLE 1). The GmFATB2A has the largest gene length among soybean TEs due to its extended 3'-UTR region. The gene structures of GmFATB are highly conserved with six exons for all ten members; on the contrary, GmFATA1A and GmFATA1B have seven and eight exons respectively (FIG. 2).

Figure 3:
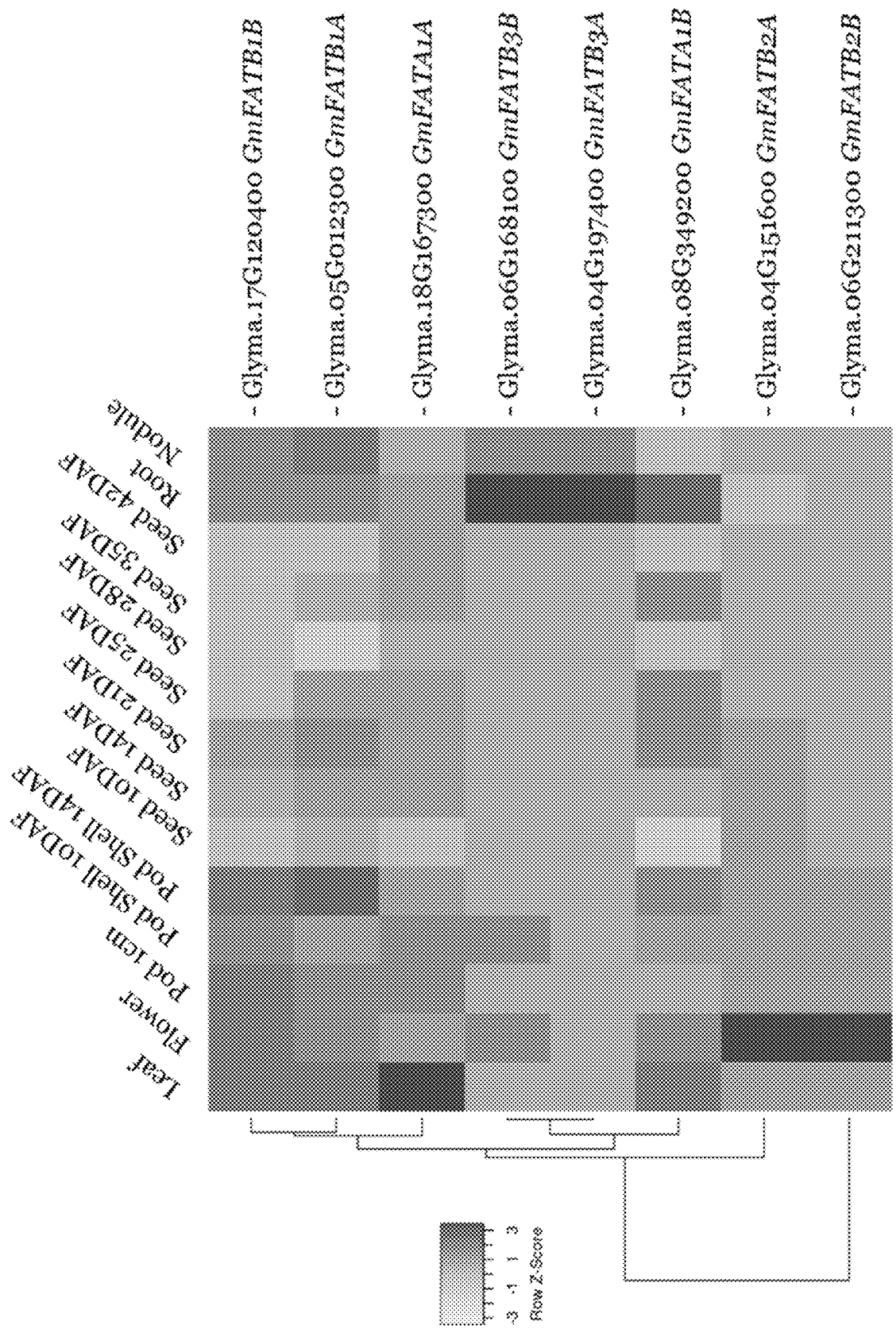
FIG. 3 is a graph showing the tissue-specific expression profiles of GmFATA and GmFATB genes. Color key represents the relative transcript abundance from low (yellow) to high (Red). No expression was detected for GmFAT5A gene in all tissues, and the expression profiles are not available for GmFAT4A/B and GmFAT5B genes in RNA-Seq Atlas database.

GmFATB1A, GmFATB1B, and GmFATB2A have relatively high expression in soybean seeds while the transcripts of two GmFATB2 genes were abundant in soybean flower. GmFATA1A and GmFATA1B were also highly expressed in soybean seeds. Two GmFATB1 genes were expressed relatively high levels in soybean root and nodule. Additionally, the expression of GmFATB1, GmFATB2, and GmFATA exhibited similar patterns in leaves and pod. The expression of GmFATB3A, GmFATB3B, and GmFATB5A were recorded as 0 in most of tested tissues and no RNA-seq data is available for GmFATB4A, GmFATB4B, and GmFATB5B in Soybase (FIG. 3).

Example 11. Chromosomal Distribution and Gene Duplication

Figure 4:
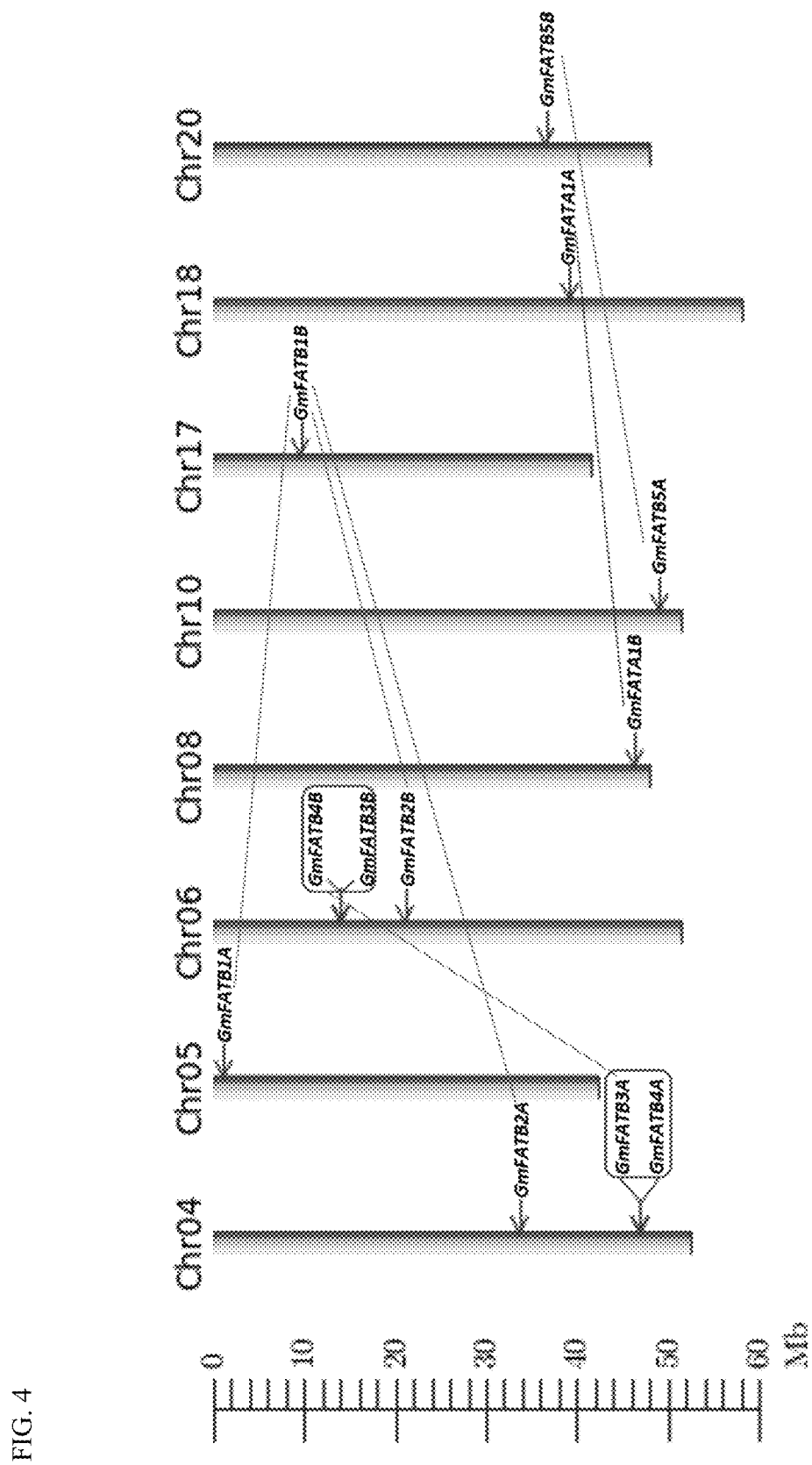
FIG. 4 is a schematic showing the chromosomal locations and duplications of soybean acyl-ACP thioesterase genes. Each chromosome number is indicated above bar by Roman number and the scale (on the left) is in mega base (Mb). The size of chromosome and gene locations are based on soybean genome annotation a2.v1 on SoyBase. Each pair of segmental duplication in GmFATA and GmFATB subfamilies are connected by red and blue lines, respectively. The tandem duplicated genes are shown in rectangle box.

Based on the physical locations, 12 soybean TE genes were unevenly distributed on eight soybean chromosomes (FIG. 4). Chromosome 4 and 6 contains three GmFATB genes each while only one GmFATB gene each is present on chromosome 5, 10, 17, and 20. Two GmFATA genes are located at chromosome 8 and 18, respectively. Among the GmFATB subfamilies, GmFATB1 and GmFATB5 are evenly distributed on four chromosomes. Nevertheless, the other three subfamilies, GmFATB2, GmFATB3, and GmFATB4, are concentrated on two chromosomes with three on each (FIG. 4).

Figure 5A:
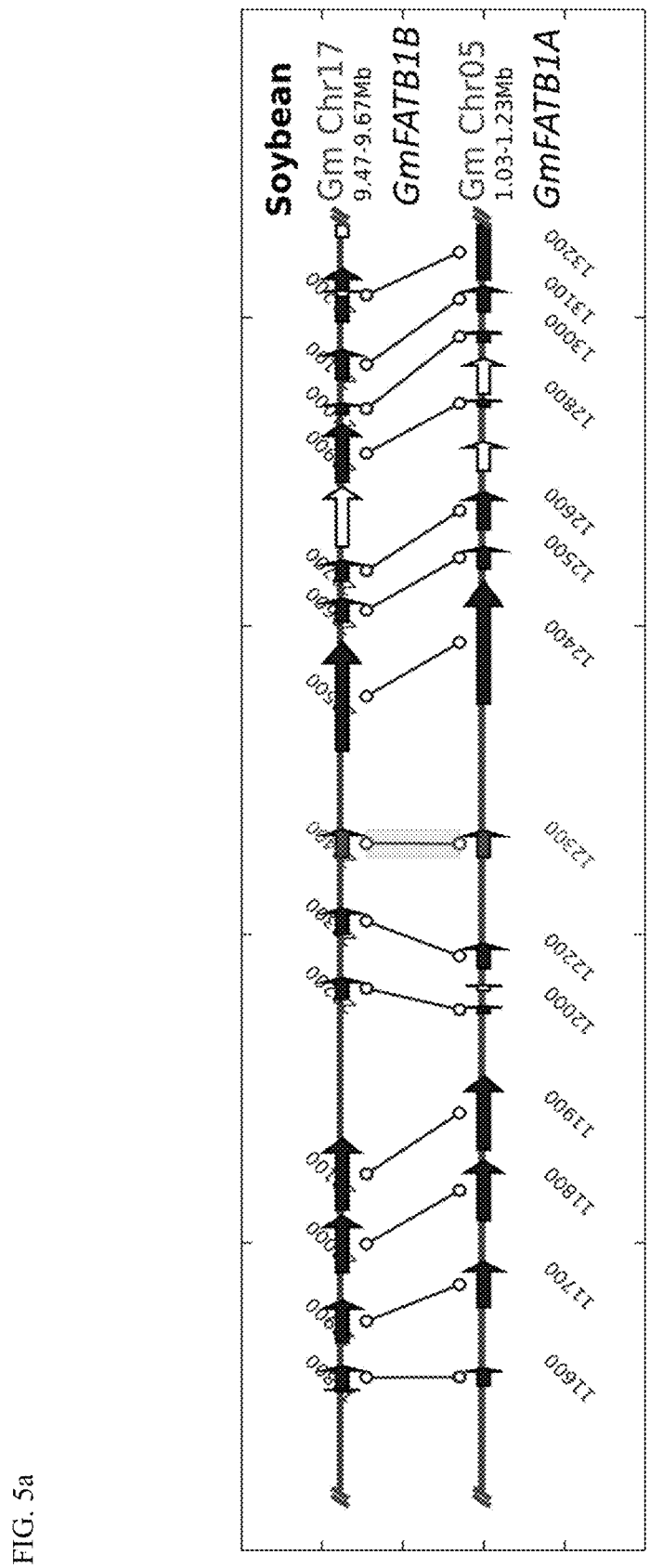
FIGS. 5a-5c are a series of diagrams illustrating the syntenic regions containing acyl-ACP thioesterase genes in soybean genome. Top, Region containing GmFATB1A/GmFATB1B gene pair; Middle, Region containing GmFATB3A/GmFATB4B gene pair; Bottom, Region containing GmFATB5A/GmFATB5B gene pair. Graphs represent ±500 kb duplicated region centered in the soybean acyl-ACP thioesterase genes.
Figure 5B:
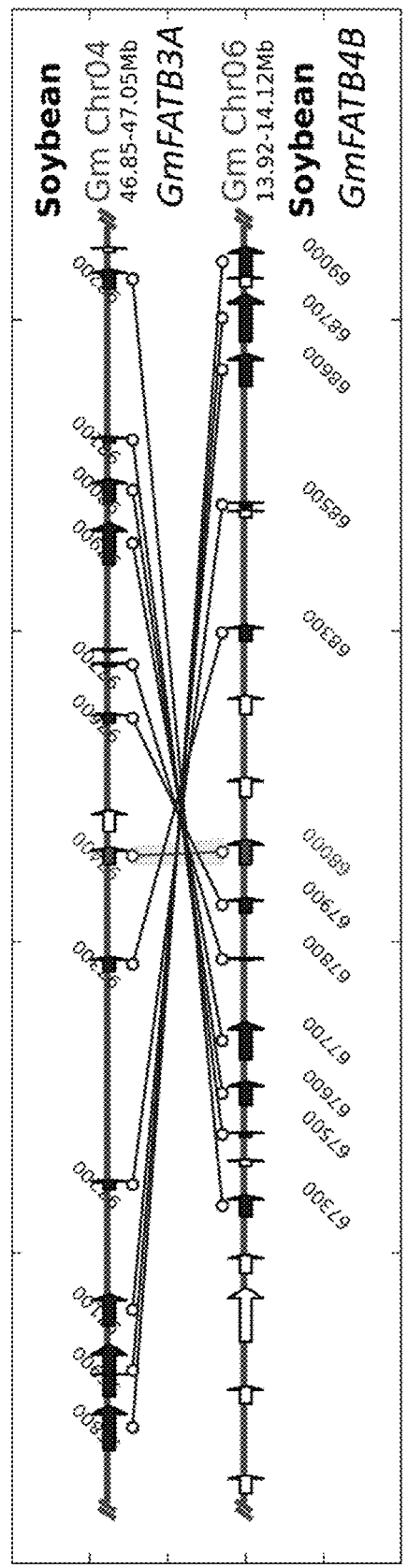
Figure 5C:
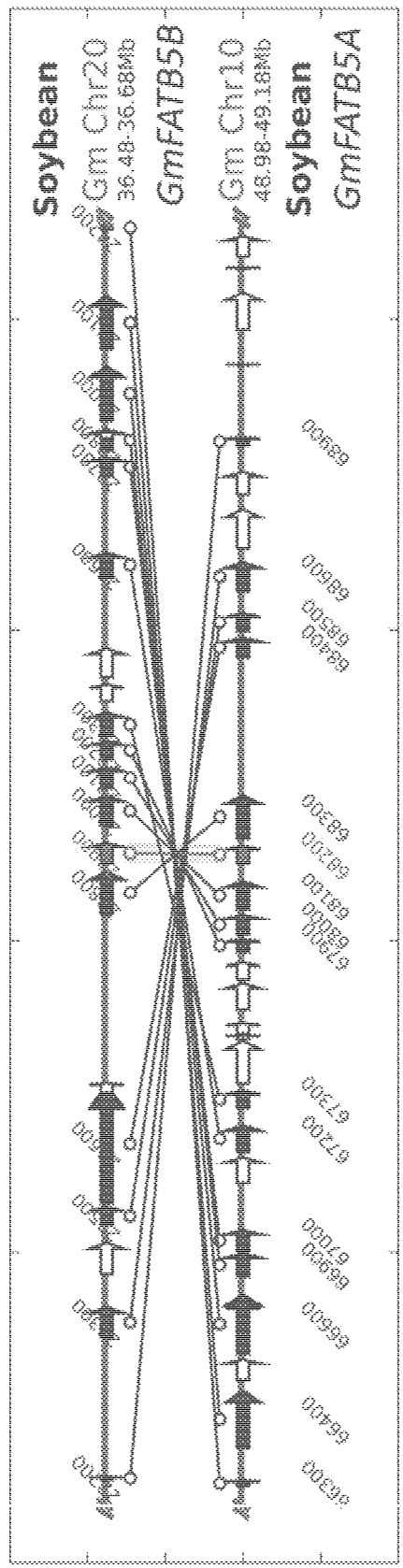

The duplication analyses have shown that all soybean TE genes are located within eight duplicated blocks (TABLE 2). The gene pair, GmFATB1A and GmFATB1B, belongs to a large duplicated segment containing 62 anchor genes, while GmFATB3A/GmFATB4B and GmFATB5A/GmFAT5B are presented in huge syntenic regions with 711 and 884 anchor genes, respectively (FIGS. 5a-5c). Two gene pairs, GmFATB3A/GmFATB4A and GmFATB3B/GmFATB4B, are regarded as outcome of tandem duplication events due to their tight physical distance of less than 7 kb (without any gene in between). The ratio of nonsynonymous to synonymous substitutions (Ka/Ks) were calculated for each gene pair to determine the types of natural selection acting on coding sequences. The Ka/Ks of soybean TEs gene pairs are less than 0.5, which suggested that the evolution of soybean TEs is under purifying selection. The duplication of eight gene pairs was estimated to have occurred between 7.38 and 76.23 Mya based on 6.161029 synonymous mutations per synonymous site per year for soybean (TABLE 2).

base changes with 45.7% in G to A and 37.1% in C to T while the other types of mutations only took up 17.1% (FIG. 8). In the coding regions of these five GmFAT genes, a total of 118 amino acid changes were detected, from which 71.2% was missense mutations, 26.3% was silent mutations, and 2.5% was nonsense mutations. Nonsense mutations were found in GmFATA1A, and GmFATB2A/2B genes whereas no nonsense mutations presented in GmFATB1A/1B genes (FIG. 8).

TABLE 2

Divergence and duplication of acyl-ACP thioesterase gene pairs in soybean.

| Acyl-ACP thioesterase gene pairs | Ka | Ks | Ka/Ks | Duplication time (Mya) | Duplication type |
|---|---|---|---|---|---|
| GmFATB1A-GmFATB1B | 0.02 | 0.09 | 0.222 | 7.38 | Segmental |
| GmFATB1B-GmFATB2A | 0.16 | 0.86 | 0.186 | 70.49 | Segmental |
| GmFATB1B-GmFATB2B | 0.17 | 0.93 | 0.183 | 76.23 | Segmental |
| GmFATB3A-GmFATB4A | 0.28 | 0.71 | 0.392 | 58.20 | Tandem |
| GmFATB3A-GmFATB4B | 0.22 | 0.56 | 0.393 | 45.90 | Segmental |
| GmFATB3B-GmFATB4B | 0.27 | 0.65 | 0.414 | 53.28 | Tandem |
| GmFATB5A-GmFATB5B | 0.02 | 0.1 | 0.2 | 8.20 | Segmental |
| GmFATA1A-GmFATA1B | 0.04 | 0.1 | 0.457 | 8.20 | Segmental |

Example 12. Conserved Domain Variations Among Plant TEs

Figure 7:
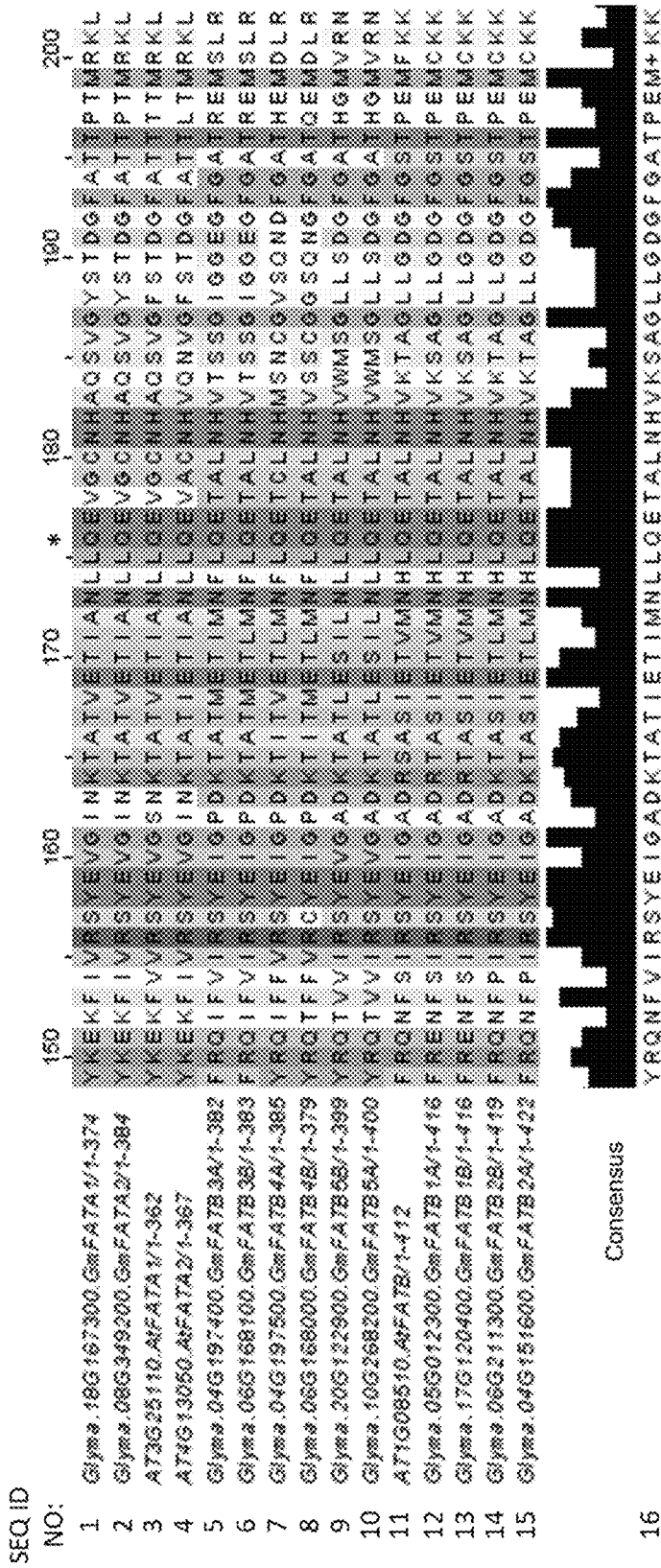
FIG. 7 is a schematic showing the multiple sequence alignment of the conserved hotdog domain of soybean and *Arabidopsis* acyl-ACP thioesterases (SEQ ID NOs: 1-16). The alignment was constructed with MUSCLE using Mega X and viewed using Jalview multiple alignment editor program. The seven active sites of plant acyl-ACP thioesterases were marked with * on top. Two active sites overlapping with predicted substrate specificity sites were highlighted in red.

The protein sequences of 15 soybean and *Arabidopsis thaliana* TEs, four FATA and eleven FATB, were aligned to compare residues within two conserved hotdog domains. A residue that is conserved within one plant TE class but differs between FATA and FATB classes may contribute to the difference in substrate specifying. Based on these criteria, a total of 13 residues were selected, from which A194G, T208V, and D276E have previously been reported as specificity determining positions. Additional 7 residues were found completely different between FATA and FATB classes in hotdog domain I, including K150R, N163D, V178T, H212Q, I213V, R236K, and K246R. In hotdog domain II, another three residues, T347K, D362E, and D372E, met the same criteria (FIG. 6). Among the ten newly identified residues, three residues, V178T, H212Q, and T347K, presented non-conservative difference in amino acid between FATA and FATB, while the rest of seven residues contain conservative changes. In addition, three conserved catalytic residues, N340, H342, and C377, may form a papain-like catalytic triad across the FATA and FATB classes. From Conserved Domain Database (CDD) at National Center for Biotechnology Information (NCBI), seven active sites of plant TEs have been revealed in hotdog domain I. Among them, two residues, T208V and R236K, overlapped with ones identified as substrate specifying residues, while the rest were highly conserved between FATA and FATB classes except two mismatches at positions 237 and 238 (FIG. 7).

Example 13. Identification of New Alleles of GmFAT to Alter Fatty Scid Composition in Soybean Seed Five soybean acyl-ACP thioesterase genes, GmFATA1A, GmFATB1A/1B, and GmFATB2A/2B, have been included in screening mutations through TbyS. The estimated mutation density of these five genes was 1/232 kb using the formula as the total number of mutations divided by the total number of base pairs (amplicon size×individuals screened) (FIG. 8). Among the 280 identified mutations in these five GmFAT genes, the typical EMS-type mutations were the majority of A subset of GmFAT mutants, including GmFATA1A, GmFATB1A, and GmFATB/B, have been confirmed by Sanger sequencing, and their novel alleles have been associated with altered fatty acid profiles. Six missense mutations (S37F, A55T, T146I, A231V, G277E, and V310I) were identified from four GmFATA/A mutants, in which two mutants, F243 and F393, presented >32% high oleic acid content. The other four mutants, F740, F636, F996, and F1305, have moderate high oleic acid content (25.3% to 28.6) compared to Forrest wild type (20.0%) (FIG. 9). Six GmFATB1A mutants (F1040, F1129, F236, F1200, F1108, and F1166) carried missense mutations, P18L, G128R, G180D, G223E, D284N, and A371T, respectively. The palmitic acid content of these six mutants ranged from 7.5% to 10.5%, but an increase in oleic acid content (22.2%-34%) were also found in GmFATB1A mutants (FIG. 9). In addition, the F1166 mutant presented increase stearic acid content up to 7.1%, which is about two times the content contained in the Wild type Forrest. Likewise, five missense mutations (P118S, I127X, G128E, A174T, and R348K) were detected at GmFATB1B from which the F359 mutant presented a high stearic acid content (7.6%), which is more than two times the content contained in the Wild type Forrest. All five mutations presented an elevated oleic acid content up to 34.4% (FIG. 9). Four mutants at the GmFATB-2A were identified (P16L, A373T, R385Q, and G395D). All four mutations presented increase oleic acid content between 24.6% and 36.5%. Stearic acid content was up to 6.1% in the F1220 mutant. Three GmFATB-2B mutants were identified (Q330*, G46S, and V255M). The F317 mutant presented a high seed oleic acid content (up to 34.8%) in addition to containing the highest seed stearic acid content (10%), which is about three times the content contained in the Wild type Forrest.

Example 14. Application of Acyl-ACP Thioesterase Gene Family Findings

Among type II fatty acid synthases (FAS), the plant TE is a major contributing factor in determining the carbon chain length of fatty acids through their substrate specificity. The large number of soybean TE genes implied genome expansion of the soybean compared to counterparts in other plant species. Previous study has identified four unique GmFATB genes, from which mutations at GmFATB1A resulted in low palmitic acid content in soybean seed [Cardinal et al., 2007]. In this study, we performed a genome-wide search for soybean TE genes with the aid of Phytozome and ThYme databases. Additional six GmFATB genes have been identified and named according to previously proposed nomenclature as well as two GmFATA genes (TABLE 1). The total number of TE genes was 4 times higher in soybean compared to *A. thaliana*. Here we conducted an overall phylogenetic analysis of plant TEs gene families from nine plant species using Maximum Likelihood (ML) method (FIG. 1). Interestingly, GmFATB1 and GmFATB2, GmFATB3 and GmFATB4, and GmFATB5 subfamilies were in three different subgroups under FATB cluster, respectively. For plant species with high palmitic acid levels, such as coconut and palm, their FATBs appear to evolve independently from dicot species. Although two FATA and one FATB genes are presented in *Arabidopsis* genome, members from FATA class are generally much less than ones from FATB class in other higher plants. Two GmFATA were grouped with FATAs in other three legume species but apart from ones in other dicot species (FIG. 1).

The gene structures are similar within GmFATB1/GmFATB2 subfamilies, GmFATB3/GmFATB4/GmFATB5 subfamilies, and GmFATA. Although the GmFATA have the larger gene lengths due to the extended intron length, the coding sequence lengths of GmFATA is generally smaller than that of GmFATB. The gene lengths of GmFATB1 and GmFATB2 subfamilies are larger than that of GmFATB3, GmFATB4, and GmFATB5 subfamilies, so does the coding sequences (TABLE 1). With the advent of intron gain/loss events, all GmFATB lost at least one intron when they evolved divergently from GmFATA (FIG. 2). The expression profiling data revealed various expression patterns of eight soybean TE genes in six soybean tissues. The similar expression patterns pointed to functional redundancy during soybean evolution, which could lead to neofunctionalization and subfunctionalization within soybean TE gene family (FIG. 3). As expected, the high transcript levels of GmFATB1 subfamilies, GmFATB2A, and GmFATA have been detected in soybean seeds, which indicated that these genes play a major role in releasing free fatty acids to cytosol. Thus, they should be the main targets to genetically modify fatty acids composition in soybean seed. For the newly identified GmFATB members, the very low expression levels of GmFATB3A, GmFATB3B, and GmFATB5A in all six tissues suggested that their functions need to be explored further (FIG. 3).

The distribution of 12 soybean TE genes have been shown on eight chromosomes (FIG. 4). Chromosome 4 and 6 contain the highest number of TE genes (3), whereas chromosome 5, 8, 10, 17, 18 and 20 only have one TE gene on each. The majority of soybean TE genes are found towards the chromosome ends, suggesting potential inter-chromosomal crossovers due to the high genetic recombination rates. Plant species acquired novel traits and adapted to various environments through gene duplication. There are three main gene duplication patterns, including segmental duplication, tandem duplication, and transposition. Our syntenic analysis showed that soybean TE gene family expanded through both segmental and tandem duplications (TABLE 2). It is also well known that two whole-genome duplication events have occurred in soybean genome, including one shared by legume species 59 million years ago and another glycine-specific one around 13 million year ago. The duplication time of soybean TE gene pairs were estimated to match with either of these two time periods. GmFATB1B/GmFATB2A, GmFATB1B/GmFATB2B, GmFATB3A/GmFATB4A, GmFATB3A/GmFATB4B, and GmFATB3B/GmFATB4B were formed between 45.90 and 76.23 Mya while the duplication of GmFATB1A/GmFATB1B, GmFATB5A/GmFATB5B, and GmFATA1A/GmFATA1B have occurred between 7.38 and 8.20 Mya (TABLE 2).

Within two hotdog domains, 10 newly identified residues that were completely different between GmFATA and GmFATB could be the candidate positions to determine the difference in substrate specifying of TEs in soybean. Compare to other seven residues, three residues (V178T, H212Q, and T347K) may play more important roles in substrate specifying due to their non-conservative difference in amino acid (FIG. 6). In current study, one GmFATA1A mutant (F740), has been identified to possess a non-conservative amino acid changes at a previously reported specificity determining position (T208V) and confer an increased level of oleic acid in soybean seed as (FIGS. 6 and 9).

The mutations at GmFATB1A have been repeatedly associated with low palmitic acid phenotype in soybean. The expression levels of GmFATA and GmFATB may have significant impact on soybean seed fatty acid composition, however, future studies were needed to elucidate the role of soybean acyl-ACP thioesterases in controlling seed oleic acid content. This is the first time to discover that the novel alleles of GmFATA1A conferred an elevated oleic acid content in soybean seeds. The increases of oleic acid content in GmFATA1A mutants, F243 and F393, are comparable to the high oleic acid content in either GmFAD2-1A or GmFAD2-1B mutants with the same genetic background (FIG. 9). Meanwhile, the novel alleles of GmFATB1A and GmFATB1B were identified to confer low palmitic acid content in soybean seeds. Interestingly, these GmFATB1A/1B mutants also presented an elevated oleic acid content, which is consistent with significantly increase in oleic acid content from other previously reported GmFATB1A mutants (FIG. 9). It has been previously indicated that a negative correlation was existed between palmitic acid and oleic contents in both natural and mutagenized soybean populations. The identified GmFAT mutants are the new sources of seed high oleic acid and low palmitic acid contents for soybean breeding.

The invention claimed is:

1. A transgenic soybean plant having increased oleic acid content transformed with a polynucleotide encoding a fatty acid thioesterase (FAT) related promoter that functions in the soybean plant operably linked to a polynucleotide encoding a polypeptide having FAT activity,
wherein the polypeptide having FAT activity comprises a sequence at least 95% identical to wild type "Forrest"

FATB2A amino acid sequence (SEQ ID NO: 32) and further comprises one or more mutations selected from the group consisting of: P16L, A373T, R385Q, and G395D, and wherein the FAT related promoter comprises a sequence selected from the group consisting of wild type "Forrest" FATA1A (SEQ ID NO: 17), wild type "Forrest" FATB1A (SEQ ID NO: 21), wild type "Forrest" FATB1B (SEQ ID NO: 25), wild type "Forrest" FATB2A (SEQ ID NO: 29), and wild type "Forrest" FATB2B (SEQ ID NO: 33) nucleotide sequence.

2. The plant of claim 1, wherein the increased oleic acid content represents an at least about 1% increase in oleic acid content as compared to a control soybean plant lacking the polynucleotide encoding a polypeptide having FAT activity.

3. The plant of claim 1, wherein the plant has been transformed with two or more polynucleotides each encoding a FAT related promoter that functions in the soybean plant, provided that each polynucleotide encoding a FAT related promoter that functions in the soybean plant is operably linked to a polynucleotide encoding a polypeptide having FAT activity, wherein at least one polypeptide having FAT activity comprises a sequence at least 95% identical to wild type "Forrest" FATB2A amino acid sequence (SEQ ID NO: 32), and further comprises one or more mutations selected from the group consisting of: P16L, A373T, R385Q, and G395D, and wherein at least one FAT related promoter comprises a sequence selected from the group consisting of wild type "Forrest" FATA1A (SEQ ID NO: 17), wild type "Forrest" FATB1A (SEQ ID NO: 21), wild type "Forrest" FATB1B (SEQ ID NO: 25), wild type "Forrest" FATB2A (SEQ ID NO: 29), and wild type "Forrest" FATB2B (SEQ ID NO: 33) nucleotide sequence.

4. A method of increasing oleic acid content of a soybean plant, the method comprising:

transforming a soybean plant with a polynucleotide encoding a fatty acid thioesterase (FAT) related promoter that functions in the soybean plant operably linked to a polynucleotide encoding a polypeptide having FAT activity, wherein the polypeptide having FAT activity comprises a sequence at least 95% identical to wild type "Forrest" FATB2A amino acid sequence (SEQ ID NO: 32) and further comprises one or more mutations selected from the group consisting of: P16L, A373T, R385Q, and G395D, and wherein the FAT related promoter comprises a sequence selected from the group consisting of wild type "Forrest" FATA1A (SEQ ID NO: 17), wild type "Forrest" FATB1A (SEQ ID NO: 21), wild type "Forrest" FATB1B (SEQ ID NO: 25), wild type "Forrest" FATB2A (SEQ ID NO: 29), and wild type "Forrest" FATB2B (SEQ ID NO: 33) nucleotide sequence.

5. The method of claim 4, wherein the increased oleic acid content represents an at least about 1% increase in oleic acid as content compared to a control soybean plant that is not transformed with a polynucleotide encoding a polypeptide having FAT activity.

* * * * *